US009464288B2

(12) United States Patent
Soll et al.

(10) Patent No.: US 9,464,288 B2
(45) Date of Patent: Oct. 11, 2016

(54) COMPOSITIONS AND METHODS FOR MAKING SELENOCYSTEINE CONTAINING POLYPEPTIDES

(75) Inventors: Dieter Soll, Guilford, CT (US); Caroline Aldag, New Haven, CT (US); Michael Hohn, Scotch Plains, NJ (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/131,382

(22) PCT Filed: Jul. 11, 2012

(86) PCT No.: PCT/US2012/046252
§ 371 (c)(1),
(2), (4) Date: Jan. 7, 2014

(87) PCT Pub. No.: WO2013/009868
PCT Pub. Date: Jan. 17, 2013

(65) Prior Publication Data
US 2014/0154744 A1 Jun. 5, 2014

Related U.S. Application Data

(60) Provisional application No. 61/506,338, filed on Jul. 11, 2011.

(51) Int. Cl.
| C12N 15/113 | (2010.01) |
| C07K 14/47 | (2006.01) |
| C12P 21/02 | (2006.01) |
| C12N 15/11 | (2006.01) |
| A61K 47/48 | (2006.01) |
| C12N 9/02 | (2006.01) |
| C12N 9/10 | (2006.01) |

(52) U.S. Cl.
CPC ....... *C12N 15/113* (2013.01); *A61K 47/48338* (2013.01); *C07K 14/47* (2013.01); *C12N 9/0004* (2013.01); *C12N 9/0008* (2013.01); *C12N 9/1007* (2013.01); *C12N 15/11* (2013.01); *C12P 21/02* (2013.01)

(58) Field of Classification Search
CPC combination set(s) only.
See application file for complete search history.

(56) References Cited

U.S. PATENT DOCUMENTS

| 5,700,660 A * | 12/1997 | Leonard et al. ............. 435/69.1 |
| 6,503,729 B1 | 1/2003 | Bult |
| 7,723,069 B2 | 5/2010 | Soll |
| 9,090,928 B2 | 7/2015 | Park |
| 2003/0082575 A1 | 5/2003 | Schultz |
| 2014/0154744 A1 | 6/2014 | Soll |

FOREIGN PATENT DOCUMENTS

| EP | 2246428 | 11/2010 |
| JP | 2008061538 | 3/2008 |
| WO | 0044906 | 8/2000 |
| WO | 2006107813 | 10/2006 |

OTHER PUBLICATIONS

Caroline Aldag Rewiring Translation for Elongation Factor Tu-Dependent Selenocysteine Incorporation. Angew. Chem. Int. Ed. 2013, 52, 1441-1445.*
Bradley A. Carlson Transfer RNAs That Insert Selenocysteine Methods in Enzymolozy, vol. 347. p. 24-39.*
Boyington, et al., "Crystal structure of formate dehydrogenase H: catalysis involving Mo, molybdopterin, selenocysteine, and an Fe4S4 cluster", Science, 275:1305-08 (1997).
Carlson, et al., "Transfer RNAs that insert selenocysteine", Methods Enzymol, 347:24-39 (2002).
Diamond, et al., "Dietary selenium affects methylation of the wobble nucleoside in the anticodon of selenocysteine tRNA([Ser]Sec).", J. Biol. Chem., 268:14215-23 (1993).
Fukunaga and Yokoyama, "Structural insights into the first step of RNA-dependent cysteine biosynthesis in archaea", Nat Struct Mol Biol., 14:272-9 (2007).
Hofer, et al., "An engineered selenocysteine defines a unique class of antibody derivatives",PNAS, 105(34)12451-6 (2008).
Hohsaka, et al., "Five-base codons for incorporation of nonnatural amino acids into proteins", Nucleic Acids Res., 29:3646-51 (2001).
Jacob, et al., "Sulfur and selenium: the role of oxidation state in protein structure and function", Angew. Chem. Int. Ed. Engl., 42:4742-58 (2003).
Johansson, et al., "Selenocysteine in proteins-properties and biotechnological use", Biochim Biophys Acta., 1726:1-13 (2005).
Kryukov, et al, "Characterization of mammalian selenoproteomes", Science, 300:1439-43 (2003).
Lee, et al., "The discriminator base influences tRNA structure at the end of the acceptor stem and possibly its interaction with proteins", PNAS, 90(15):7149-52 (1993).
Liu, et al., "Catalytic mechanism of Sep-tRNA:Cys-tRNA synthase: sulfur transfer is mediated by disulfide and persulfide", J. Biol. Chem., 287:5426-33 (2012).
Palioura, et al., "The human SepSecS-tRNASec complex reveals the mechanism of selenocysteine formation", Science, 325:321-5 (2009).
Raffa, "Diselenium, instead of disulfide, bonded analogs of conotoxins: novel synthesis and pharmacotherapeutic potential", Life Sci., 87(15-16):451-6 (2010).
Riaz and Mehmood, "Selenium in Human Health and Disease: A Review", JPMI, 26(02):120-33 (2012).

(Continued)

*Primary Examiner* — Kagnew H Gebreyesus
(74) *Attorney, Agent, or Firm* — Pabst Patent Group LLP

(57) ABSTRACT

Non-naturally occurring tRNA$^{Sec}$ and methods of using them for recombinant expression of proteins engineered to include one or more selenocysteine residues are disclosed. The non-naturally occurring tRNA$^{Sec}$ can be used for recombinant manufacture of selenocysteine containing polypeptides encoded by mRNA without the requirement of an SECIS element. In some embodiments, selenocysteine containing polypeptides are manufactured by co-expressing a non-naturally occurring tRNA$^{Sec}$ a recombinant expression system, such as *E. coli*, with SerRS, EF-Tu, SelA, or PSTK and SepSecS, and an mRNA with at least one codon that recognizes the anticodon of the non-naturally occurring tRNA$^{Sec}$.

19 Claims, 11 Drawing Sheets

(56) References Cited

OTHER PUBLICATIONS

Rudinger, et al., "Antideterminants present in minihelix(Sec) hinder its recognition by prokaryotic elongation factor Tu", EMBO J., 15(3):650-57 (1996).
Schon, et al., "The selenocysteine-inserting opal suppressor serine tRNA from *E. coli* is highly unusual in structure and modification", Nucleic Acids Res., 17 (18):7159-65 (1989).
Shchedrina, et al., "Identification and characterization of a selenoprotein family containing a diselenide bond in a redox motif", PNAS, 104(35):13919-24 (2007).
Sherrer, et al., "Characterization and evolutionary history of an archaeal kinase involved in selenocysteinyl-tRNA formation", Nucleic Acids Res., 36(4): 1247-59 (2008b).
Sherrer, et al., "Divergence of selenocysteine tRNA recognition by archaeal and eukaryotic O-phosphoseryl-tRNASec kinase", Nucleic Acids Res, 36:1871-80 (2008a).
Tapiero, et al., "The antioxidant role of selenium and selenocompounds", Biomed Pharmacother., 57:134-44 (2003).
Wu and Gross, "The length and the secondary structure of the D-stem of human selenocysteine tRNA are the major identity determinants for serine phosphorylation", EMBO J., 13:241-8 (1994).
Xu, et al., "New developments in selenium biochemistry: selenocysteine biosynthesis in eukaryotes and archaea", Biol TraceElem Res., 119(3):234-41 (2007).
Yoshizawa and Böck, "The many levels of control on bacterial selenoprotein synthesis", Biochim Biophys Acta., 1790:1404-14 (2009).
Yuan, et al., "Distinct genetic code expansion strategies for selenocysteine and pyrrolysine are reflected in different aminoacyl-tRNA formation systems", FEBS Lett., 584(2):342-9 (2010).
Yuan, et al., "RNA-dependent conversion of phosphoserine forms selenocysteine in eukaryotes and archaea", PNAS, 103:18923-7 (2006).
Alessi, et al., "dentification of the sites in MAP kinase kinase-1 phosphorylated by p74raf-1", EMBO J., 13:1610-9 (1994).
Altschul et al., "Basic local alignment search tool", J. Mol. Biol., 215 (3):403-410 (1990).
Ambrogelly, et al., "Cys-tRNACys formation and cysteine biosynthesis in methanogenic archaea: two faces of the same problem?", Cell. Mol. LifeSci., 61:2437-45 (2004).
Arslan, et al., "Structurally modified firefly luciferase. Effects of amino acid substitution at position 286", Journal of the American Chemical Society, 119(45):10877-10887 (1997).
Bajaj, et al., "Mutagenesis-based definitions and probes of residue burial in proteins", PNAS, 102(45):16221-6 (2005).
Balch, et al., "Transport of coenzyme M (2-mercaptoethanesulfonic acid) in Methanobacterium ruminantium", J. Bacteriol., 137:264 (1979).
Basurko, et al., Phosphoserine aminotransferase, the second step-catalyzing enzyme for serine biosynthesis\, IUBMB Life, 48:525-9 (1999).
Bentin, et al., "Photoreactive bicyclic amino acids as substrates for mutant *Escherichia coli* phenylalanyl-tRNA synthetases", J. Biol. Chem. 279:19839-45 (2004).
Bernard, et al., "Positive-selection vectors using the F plasmid ccdB killer gene", Gene, 148:71-4 (1994).
Bilokapic, et al., "The unusual methanogenic seryl-tRNA synthetase recognizes tRNASer species from all three kingdoms of life", Eur. Journ. Biochemistry, 271(4):694-702 (2004).
Blight, et al., "Direct charging of tRNA(CUA) with pyrrolysine in vitro and in vivo", Nature, 431(7006):333-5 (2004).
Buchner, et al., "A method for increasing the yield of properly folded recombinant fusion proteins: single-chain immunotoxins from renaturation of bacterial inclusion bodies", Anal. Biochem., 205: 263-270 (1992).
Bunjun, et al., "A dual-specificity aminoacyl-tRNA synthetase in the deep-rooted eukaryote Giardia lamblia", PNAS, 97:12997-13002 (2000).

Calendar and Berg, "Purification and physical characterization of tyrosyl ribonucleic acid synthetases from *Escherichia coli* and Bacillus subtilis", Biochemistry, 5(5):1681-90 (1966a).
Calendar and Berg, "The catalytic properties of tyrosyl ribonucleic acid synthetases from *Escherichia coli* and Bacillus subtilis", Biochemistry, 5(5):1690-5 (1966b).
Chatterji and Pachter, "Large multiple organism gene finding by collapsed Gibbs sampling", J Comput Biol., 12(6):599-608 (2005).
Dale, et al., "The affinity of elongation factor Tu for an aminoacyl-tRNA is modulated by the esterified amino acid", Biochemistry 43:6159-66 (2004).
Daly and Hearn, "Expression of heterologous proteins in Pichia pastoris: a useful experimental tool in protein engineering and production", J. Mol. Recognit., 18(2):119-38 (2005).
Das and Vothknecht, "Phenylalanyl-tRNA synthetase from the archaeon Methanobacterium thermoautotrophicum is an (alphabeta)2 heterotetrameric protein", Biochimie, 81(11):1037-9 (1999).
Datsenko, et al., "One-step inactivation of chromosomal genes in *Escherichia coli* K-12 using PCR products", PNAS, 97:6640-5 (2000).
Debinski, et al., "A wide range of human cancers express interleukin 4 (IL4) receptors that can be targeted with chimeric toxin composed of IL4 and Pseudomonas exotoxin", J. Biol. Chem., 268: 14065-14070 (1993).
Eargle, et al., "Dynamics of Recognition between tRNA and elongation factor Tu", J Mol Biol., 377(5):1382-1405 (2008).
Ellman, et al., "Biosynthetic method for introducing unnatural amino acids site-specifically specifically into proteins", Methods Enzymol., 202:301-36 (1991).
Engelhard, et al., "The insect tracheal system: a conduit for the systemic spread of Autographa californica M nuclear polyhedrosis virus", Proc. Natl. Acad. Sci. USA, 91:3224-3227 (1994).
Fabrega, et al., "An aminoacyl tRNA synthetase whose sequence fits into neither of the two known classes", Nature, 411:110-4 (2001).
Fleer, et al., "High-level secretion of correctly processed recombinant human interleukin-1 beta in Kluyveromyces lactis", Gene, 107:285-95 (1991).
Florens, et al., A proteomic view of the Plasmodium falciparum life cycle Nature, 419, 520-6 (2002).
Fromm, et al., "Expression of genes transferred into monocot and dicot plant cells by electroporation" Proc. Natl. Acad. Sci. USA, 82, 5824-8 (1985).
Giometti, et al., "Global analysis of a "simple" proteome: Methanococcus jannaschii", J. Chromatogr. B Anal. Technol. Biomed. Life Sci., 782(1-2):227-43 (2002).
Harrington, et al., "Formation of de novo centromeres and construction of first-generation human artificial microchromosomes", Nat Genet., 15:345-355 (1997).
Hitzeman, et al., "Isolation and characterization of the yeast 3-phosphoglycerokinase gene (PGK) by an immunological screening technique", J. Biol. Chem., 255:12073-80 (1980).
Hohn, et al., "Emergence of the universal genetic code imprinted in an RNA record", PNAS,103(48):18095-100 (2006).
Holland and Holland, "Isolation and identification of yeast messenger ribonucleic acids coding for enolase, glyceraldehyde-3-phosphate dehydrogenase, and phosphoglycerate kinase", Biochem., 17:4900-7 (1978).
Ibba, et al., "The adaptor hypothesis revisited", Trends Biochem. Sci., 25:311-6 (2000).
Jansen, et al., "Drag&Drop cloning in yeast", Gene, 344:43-51 (2005).
Kamtekar, et al., "Toward understanding phosphoseryl-tRNACys formation: the crystal structure of Methanococcus maripaludis phosphoseryl-tRNA synthetase", PNAS, 104(8):2620-5 (2007).
Karlin and Altschul, "Applications and statistics for multiple high-scoring segments in molecular sequences", Proc. Nat'l. Acad. Sci. USA, 90:5873-5787 (1993).
Kim, et al., "Sequence Divergence of Seryl-tRNA Synthetases in Archaea", J. Bacteriol., 180:6446-49 (1998).
Klein, et al., "High velocity microprojectiles for delivering nucleic acids into living cells", Nature, 327:70-73 (1987).

(56) References Cited

OTHER PUBLICATIONS

Kreitman and Pastan, "Purification and characterization of IL6-PE4E, a recombinant fusion of interleukin 6 with Pseudomonas exotoxin", Bioconjug. Chem., 4:581-585 (1993).
LaRiviere, et al., "Uniform binding of aminoacyl-tRNAs to elongation factor Tu by thermodynamic compensation", Science, 294(5540):165-8 (2001).
Li, et al., "Cysteinyl-tRNA formation: the last puzzle of aminoacyl-tRNA synthesis", FEBS Lett., 462:302 (1999).
Li, et al., "Usage of an intronic promoter for stable gene expression in *Saccharomyces cerevisiae*", Lett Appl Microbiol., 40(5):347-52 (2005).
Ling, et al., "Pathogenic mechanism of a human mitochondrial tRNAPhe mutation associated with myoclonic epilepsy with ragged red fibers syndrome", PNAS, 104(39):15299-304 (2007a).
Ling, et al., "Phenylalanyl-tRNA synthetase editing defects result in efficient mistranslation of phenylalanine codons as tyrosine", RNA., 13(11):1881-6 (2007b).
Lipman, et al., "Synthesis of cysteinyl-tRNA(Cys) by a genome that lacks the normal cysteine-tRNA synthetase" Biochemistry 39:7792-8 (2000).
Logan and Shenk, "Adenovirus tripartite leader sequence enhances translation of mRNAs late after infection" Proc. Natl. Acad. Sci. USA, 81:3655-3659 (1984).
Maccoss, et al., "Probability-based validation of protein identifications using a modified SEQUEST algorithm", Anal. Chem., 74:5593-9 (2002).
Margelevicius and Venclovas, "PSI-BLAST-ISS: an intermediate sequence search tool for estimation of the position-specific alignment reliability", BMC Bioinformatics, 6:185 (2005).
Min, et al., "Transfer RNA-dependent amino acid biosynthesis: an essential route to asparagine formation", Proc. Natl. Acad. Sci. U.S.A., 99:2678 (2002).
Mino and Ishikawa, "A novel O-phospho-L-serine sulfhydrylation reaction catalyzed by O-acetylserine sulfhydrylase from Aeropyrum pernix K1", FEBS Lett., 551:133-8 (2003).
Mizutani, et al., "Possible incorporation of phosphoserine into globin readthrough protein via bovine opal suppressor phosphoseryl-tRNA", FEBS Lett., 207(1):162-6 (1986).
Moore, "On the Determination of Cystine as Cysteic Acid", J. Biol. Chem., 238:235-7 (1963).
Needleman and Wunsch, "A general method applicable to the search for similarities in the amino acid sequence of two proteins", J. Mol. Biol., 4(3):443-53 (1970).
Nissen, et al., "Crystal structure of the ternary complex of Phe-tRNAPhe, EF-Tu, and a GTP analog", Science, 270(5241)1464-72 (1995).
Normanly, et al., "Changing the identity of a transfer RNA", Nature, 321:213-9 (1986).
Park, et al., "Design and evolution of new catalytic activity with an existing protein scaffold", Science 311(5760):535-8 (2006).
Park, et al., "Expanding the genetic code of *Escherichia coli* with phosphoserine", Science, 33(6046):1151-4 (2011).
Pearson and Lipman, "Improved tools for biological sequence comparison", Proc. Nat'l. Acad. Sci. USA, 85:2444-8 (1988).
Polycarpo, et al., "Activation of the pyrrolysine suppressor tRNA requires formation of a ternary complex with class I and class II lysyl-tRNA synthetases", Mol.Cell, 12:287-94 (2003).
Polycarpo, et al., "An aminoacyl-tRNA synthetase that specifically activates pyrrolysine", Proc. Natl. Acad. Sci. U.S.A., 101;12450 (2004).
Rothman, et al., "Caged phosphoproteins", J Am Chem Soc., 127(3):846-7 (2005).
Ruan, et al., "Cysteinyl-tRNA(Cys) formation in Methanocaldococcus jannaschii: the mechanism is still unknown", J. Bacteriol. 186, 8-14 (2004).
Sadygov and Yates, A hypergeometric probability model for protein identification and validation using tandem mass spectral data and protein sequence databases\, Anal. Chem., 75:3792-8 (2003).
Sandig, et al., "Gene transfer into hepatocytes and human liver tissue by baculovirus vectors", Hum. Gene Ther., 7:1937-1945 (1996).
Sauerwald, et al., "RNA-dependent cysteine biosynthesis in archaea", Science, 307(5717):1969-72 (2005).
Schrader, et al. "Understanding the sequence of tRNA binding to EF-TU using tRNA mutagenesis", J Mol Biol, 386(5):1255-64 (2009).
Sebolt-Leopold, et al., "Targeting the mitogen-activated protein kinase cascade to treat cancer", Nat Rev Cancer, 4:937-47 (2004).
Smith and Waterman, "Comparison of Biosequences", Adv. Appl. Math., 2:482-89 (1981).
Stathopoulos, et al., "Cysteinyl-tRNA synthetase is not essential for viability of the archaeon Methanococcus maripaludis", Proc. Natl. Acad. Sci. U.S.A., 98:14292-7 (2001).
Stathopoulos, et al., "One polypeptide with two aminoacyl-tRNA synthetase activities", Science, 287(5452):479-82 (2000).
Studier, "Protein production by auto-induction in high density shaking cultures", Protein Expr Purif.,41(1):207-34 (2005).
Tabb, et al., "DTASelect and Contrast: tools for assembling and comparing protein identifications from shotgun proteomics", J. Proteome Res., 1:21-6 (2002).
Takamatsu, et al., "Expression of bacterial chloramphenicol acetyltransferase gene in tobacco plants mediated by TMV-RNA", EMBO J., 6:307-311 (1987).
Tomari, et al., "The role of tightly bound ATP in *Escherichia coli* tRNA nucleotidyltransferase", Genes Cells, 5:68998 (2000).
Tumbula, et al., "Transformation of Methanococcus maripaludis and identification of a PstI-like restriction system", FEMS Microbiol. Lett., 121:309-14 (1994).
Van Heeke and Schuster, "Expression of human asparagine synthetase in *Escherichia coli*", J. Biol. Chem., 264:5503-5509 (1989).
Varshney, et al., "Direct analysis of aminoacylation levels of tRNAs in vivo. Application to studying recognition of *Escherichia coli* initiator tRNA mutants by glutaminyl-tRNA synthetase", J. Biol. Chem. 266:24712 (1991).
Wang, et al., "Expanding the genetic code of *Escherichia coli*", Science, 292(5516):498-500 (2001).
Wanner, "Molecular genetic studies of a 10.9-kb operon in *Escherichia coli* for phosphonate uptake and biodegradation", FEMS Microbiol Lett., 79(1-):133-9 (1992).
White, "The biosynthesis of cysteine and homocysteine in Methanococcus jannaschii", Biochim. Biophys. Acta, 1624:46-53 (2003).
Whitman, et al., "Isolation and characterization of 22 mesophillic methanococci", Syst. Appl. Microbiol. 7:235-40 (1986).
Wolfson and Uhlenbeck, "Modulation of tRNAAla identity by inorganic pyrophosphatase", Proc. Natl. Acad. Sci. U.S.A., 99:5965-70 (2002).
Zhang, et al., "Aminoacylation of tRNA with phosphoserine for synthesis of cysteinyl-tRNA(Cys", Nat. Struct Mol. Biol., 15(5):507-14 (2008).
Zhang and Hou, "Synthesis of cysteinyl-tRNACys by a prolyl-tRNA synthetase", RNA Biol., 1:35-41 (2004).
Zhu, et al., Shotgun Proteomics of Methanococcus jannaschii and insights into methanogenesis\, J. Proteome Res., 3:538 (2004).

* cited by examiner

SEQUENCE LISTING

<160> NUMBER OF SEQ ID NOS: 58

<210> SEQ ID NO 1
<211> LENGTH: 95
<212> TYPE: RNA
<213> ORGANISM: Escherichia coli

<400> SEQUENCE: 1
ggaagaucgu cgucuccggu gaggcggcug gacuucaaau ccaguugggg ccgccagcgg    60
ucccgggcag guucgacucc ugugaucuuc cgcca                              95

<210> SEQ ID NO 2
<211> LENGTH: 93
<212> TYPE: RNA
<213> ORGANISM: Methanococcus maripaludis

<400> SEQUENCE: 2
ggcacggggu gcuuaucuug guagaugagg gcggacuuca gauccgucga guuccguugg    60

-continued

```
aauucggggu ucgauucccc cccugcgccg cca                              93

<210> SEQ ID NO 3
<211> LENGTH: 90
<212> TYPE: RNA
<213> ORGANISM: Homo sapiens

<400> SEQUENCE: 3
gcccggauga uccucagugg ucuggggugc aggcuucaaa ccuguagcug ucuagggaca  60 gaguguuca auuccaccuu ucgggcgcca                                   90

<210> SEQ ID NO 4
<211> LENGTH: 88
<212> TYPE: RNA
<213> ORGANISM: Escherichia coli

<400> SEQUENCE: 4
ggaagugugg ccgagcgguu gaaggcaccg gucuugaaaa ccggcgaccc gaaaggguuc  60
cagaguucga aucucugcgc uuccgcca                                    88

<210> SEQ ID NO 5
<211> LENGTH: 90
<212> TYPE: RNA
<213> ORGANISM: Methanococcus maripaludis

<400> SEQUENCE: 5
gcagaggugg uugagcuugg ccaaaggcgc cggacuugaa auccgguucu ccacugggga  60
gcggggguuc aaaucccucc cucugcgcca                                  90

<210> SEQ ID NO 6
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 6
ggaagaugug gccgagcggu ugaaggcacc ggucuucaaa accggcgacc cgaaaggguu  60
ccagaguucg aaucucugca ucuuccgcca                                  90

<210> SEQ ID NO 7
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 7
ggaagaugug gccgagcggu ugaaggcacc ggucucuaaa accggcgacc cgaaagggu   60 ccagaguucg aaucucugca ucuuccgcca                                  90

<210> SEQ ID NO 8
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 8
ggaagaugug gccgagcggu ugaaggcacc ggucuuuaaa accggcgacc cgaaagggu   60
```

```
ccagaguucg aaucucugca ucuuccgcca                                    90
```

<210> SEQ ID NO 9
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 9

```
ggcacugugg ccgagcgguu gaaggcaccg gucuucaaaa ccggcgaccc gaaaggguuc   60
cagaguucga aucucugcgg ugccgcca                                     88
```

<210> SEQ ID NO 10
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 10

```
ggcacugugg ccgagcgguu gaaggcaccg gucucuaaaa ccggcgaccc gaaaggguuc   60
cagaguucga aucucugcgg ugccgcca                                     88
```

<210> SEQ ID NO 11
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 11

```
ggcacugugg ccgagcgguu gaaggcaccg gucuuuaaaa ccggcgaccc gaaaggguuc   60
cagaguucga aucucugcgg ugccgcca                                     88
```

<210> SEQ ID NO 12
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 12

```
gggcacugug gccgagcggu ugaaggcacc ggucuucaaa accggcgacc cgaaaggguu   60
ccagaguucg aaucucugcg gugcccgcca                                   90
```

<210> SEQ ID NO 13
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 13

```
ggcacuggug gccgagcggu ugaaggcacc ggucuucaaa accggcgacc cgaaaggguu   60
ccagaguucg aaucucugcc ggugccgcca                                   90
```

<210> SEQ ID NO 14
<211> LENGTH: 88
<212> TYPE: RNA
<213> ORGANISM: Artificial Sequence
<220> FEATURE:
<223> OTHER INFORMATION: Synthetic tRNA -continued

<400> SEQUENCE: 14
ggcacugugg ccgagcgguu gaaggcaccg gucuucaaaa ccggcgaccc gaaaggguuc    60
cugaguucga aucucagcgg ugccgcca                                      88

<210> SEQ ID NO 15
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 15
gggcacuggu ggccgagcgg uugaaggcac cggucuucaa aaccggcgac ccgaaagggu    60
uccagaguuc gaaucucugc cggugcccgc ca                                 92

<210> SEQ ID NO 16
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 16
gggcacugug gccgagcggu ugaaggcacc ggucuucaaa accggcgacc cgaaaggguu    60
ccugaguucg aaucucagcg gugcccgcca                                    90

<210> SEQ ID NO 17
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 17
ggcacuggug gccgagcggu ugaaggcacc ggucuucaaa accggcgacc cgaaaggguu    60
ccugaguucg aaucucagcc ggugccgcca                                    90

<210> SEQ ID NO 18
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 18
gggcacuggu ggccgagcgg uugaaggcac cggucuucaa aaccggcgac ccgaaagggu    60
uccugaguuc gaaucucagc cggugcccgc ca                                 92

<210> SEQ ID NO 19
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 19
gggcacugug gccgagcggu ugaaggcacc ggucucuaaa accggcgacc cgaaaggguu    60
ccagaguucg aaucucugcg gugcccgcca                                    90

<210> SEQ ID NO 20

```
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 20
ggcacuggug gccgagcggu ugaaggcacc ggucucuaaa accggcgacc cgaaaggguu      60
ccagaguucg aaucucugcc ggugccgcca                                      90

<210> SEQ ID NO 21
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 21
ggcacugugg ccgagcgguu gaaggcaccg gucucuaaaa ccggcgaccc gaaagggguuc     60 cugaguucga aucucagcgg ugccgcca                                        88

<210> SEQ ID NO 22
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 22
gggcacuggu ggccgagcgg uugaaggcac cggucucuaa aaccggcgac ccgaaagggu     60
uccagaguuc gaaucucugc cggugcccgc ca                                  92

<210> SEQ ID NO 23
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 23
gggcacugug gccgagcggu ugaaggcacc ggucucuaaa accggcgacc cgaaagggu u    60 ccugaguucg aaucucagcg gugcccgcca                                     90

<210> SEQ ID NO 24
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 24
ggcacuggug gccgagcggu ugaaggcacc ggucucuaaa accggcgacc cgaaaggguu     60
ccugaguucg aaucucagcc ggugccgcca                                     90

<210> SEQ ID NO 25
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 25
gggcacuggu ggccgagcgg uugaaggcac cggucucuaa aaccggcgac ccgaaagggu     60
```
uccugaguuc gaaucucagc cggugcccgc ca        92

<210> SEQ ID NO 26
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 26
gggcacugug gccgagcggu ugaaggcacc ggucuuuaaa accggcgacc cgaaagggu        60 ccagaguucg aaucucugcg gugcccgcca        90

<210> SEQ ID NO 27
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 27
ggcacuggug gccgagcggu ugaaggcacc ggucuuuaaa accggcgacc cgaaagggu        60 ccagaguucg aaucucugcc ggugccgcca        90

<210> SEQ ID NO 28
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 28
ggcacugugg ccgagcgguu gaaggcaccg gucuuuaaaa ccggcgaccc gaaaggguuc        60
cugaguucga aucucagcgg ugccgcca        88

<210> SEQ ID NO 29
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 29
gggcacuggu ggccgagcgg uugaaggcac cggucuuuaa aaccggcgac ccgaaagggu        60
uccagaguuc gaaucucugc cggugcccgc ca        92

<210> SEQ ID NO 30
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 30
gggcacugug gccgagcggu ugaaggcacc ggucuuuaaa accggcgacc cgaaagggu        60 ccugaguucg aaucucagcg gugcccgcca        90

<210> SEQ ID NO 31
<211> LENGTH: 90
<212> TYPE: RNA
<213> ORGANISM: Artificial Sequence
<220> FEATURE:

<223> OTHER INFORMATION: Synthetic tRNA

<400> SEQUENCE: 31
ggcacuggug gccgagcggu ugaaggcacc ggucuuuaaa accggcgacc cgaaagggu  60 ccugaguucg aaucucagcc ggugccgcca                                  90

<210> SEQ ID NO 32
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 32
gggcacuggu ggccgagcgg uugaaggcac cggucuuuaa aaccggcgac ccgaaagggu  60
uccugaguuc gaaucucagc cggugcccgc ca                                92

<210> SEQ ID NO 33
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 33
ggcgcggugg uugagcuugg ccaaaggcgc cggacuucaa auccgguucu ccacugggga  60
gcggggguuc aaaucccucc cgcgccgcca                                  90

<210> SEQ ID NO 34
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 34
ggcgcggugg uugagcuugg ccaaaggcgc cggacucuaa auccgguucu ccacugggga  60
gcggggguuc aaaucccucc cgcgccgcca                                  90

<210> SEQ ID NO 35
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 35
ggcgcggugg uugagcuugg ccaaaggcgc cggacuuuaa auccgguucu ccacugggga  60
gcggggguuc aaaucccucc cgcgccgcca                                  90

<210> SEQ ID NO 36
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 36
gggcgcggug guugagcuug gccaaaggcg ccggacuuca aauccgguuc uccacugggg  60 agcgggguu caaaucccuc ccgcgcccgc ca                                 92

<210> SEQ ID NO 37
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 37
ggcgcgggug guugagcuug gccaaaggcg ccggacuuca aauccgguuc uccacugggg    60
agcggggguu caaaucccuc cccgcgccgc ca    92

<210> SEQ ID NO 38
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 38
ggcgcggugg uugagcuugg ccaaaggcgc cggacuucaa auccgguucu ccacugggga    60
gcguggguuc aaaucccacc cgcgccgcca    90

<210> SEQ ID NO 39
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 39
gggcgcgggu gguugagcuu ggccaaaggc gccggacuuc aaauccgguu cuccacuggg    60 gagcggggu ucaaauccu ccccgcgccc gcca    94

<210> SEQ ID NO 40
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 40
gggcgcggug guugagcuug gccaaaggcg ccggacuuca aauccgguuc uccacugggg    60
agcgugdguu caaaucccac ccgcgcccgc ca    92

<210> SEQ ID NO 41
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 41
ggcgcgggug guugagcuug gccaaaggcg ccggacuuca aauccgguuc uccacugggg    60
agcgugdguu caaaucccac ccgcgccgc ca    92

<210> SEQ ID NO 42
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 42

```
gggcgcgggu gguugagcuu ggccaaaggc gccggacuuc aaauccgguu cuccacuggg    60
gagcgugggu ucaaauccca ccccgcgccc gcca                                94
```

<210> SEQ ID NO 43
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 43

```
gggcgcggug guugagcuug gccaaaggcg ccggacucua aauccgguuc uccacugggg    60
agcggggguu caaaucccuc ccgcgcccgc ca                                  92
```

<210> SEQ ID NO 44
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 44

```
ggcgcgggug guugagcuug gccaaaggcg ccggacucua aauccgguuc uccacugggg    60
agcggggguu caaaucccuc cccgcgccgc ca                                  92
```

<210> SEQ ID NO 45
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 45

```
ggcgcggugg uugagcuugg ccaaaggcgc cggacucuaa auccgguucu ccacugggga    60
gcgugggbuc aaaucccacc cgcgccgcca                                     90
```

<210> SEQ ID NO 46
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 46

```
gggcgcgggu gguugagcuu ggccaaaggc gccggacucu aaauccgguu cuccacuggg    60 gagcggggu ucaaaucccu ccccgcgccc gcca                                 94
```

<210> SEQ ID NO 47
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 47

```
gggcgcggug guugagcuug gccaaaggcg ccggacucua aauccgguuc uccacugggg    60 agcgugggu caaaucccac ccgcgcccgc ca                                   92
```

<210> SEQ ID NO 48
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 48
ggcgcgggug guugagcuug gccaaaggcg ccggacucua aauccgguuc uccacugggg    60
agcguggguu caaaucccac cccgcgccgc ca    92

<210> SEQ ID NO 49
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 49
gggcgcgggu gguugagcuu ggccaaaggc gccggacucu aaauccgguu cuccacuggg    60 gagcguggu ucaaauccca cccgcgccc gcca    94

<210> SEQ ID NO 50
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 50
gggcgcggug guugagcuug gccaaaggcg ccggacuuua aauccgguuc uccacugggg    60
agcggggguu caaaucccuc ccgcgccgc ca    92

<210> SEQ ID NO 51
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 51
ggcgcgggug guugagcuug gccaaaggcg ccggacuuua aauccgguuc uccacugggg    60
agcggggguu caaaucccuc cccgcgccgc ca    92

<210> SEQ ID NO 52
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 52
ggcgcggugg uugagcuugg ccaaaggcgc cggacuuuaa auccgguucu ccacugggga    60
gcgugggguc aaaucccacc cgcgccgcca    90

<210> SEQ ID NO 53
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 53
gggcgcgggu gguugagcuu ggccaaaggc gccggacuuu aaauccgguu cuccacuggg    60
gagcgggggu ucaaaucccu cccgcgccc gcca    94

```
<210> SEQ ID NO 54
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 54
gggcgcggug guugagcuug gccaaaggcg ccggacuuua aauccgguuc uccacugggg      60 agcgugggu  caaaucccac ccgcgcccgc ca                                   92

<210> SEQ ID NO 55
<211> LENGTH: 92
<212> TYPE: RNA
<213> ORGANISM: Artificial Sequence
<220> FEATURE:
<223> OTHER INFORMATION: Synthetic tRNA

<400> SEQUENCE: 55
ggcgcgggug guugagcuug gccaaaggcg ccggacuuua aauccgguuc uccacugggg      60 agcgugggu  caaaucccac cccgcgccgc ca                                   92

<210> SEQ ID NO 56
<211> LENGTH: 94
<212> TYPE: RNA
<213> ORGANISM: Artificial Sequence
<220> FEATURE:
<223> OTHER INFORMATION: Synthetic tRNA

<400> SEQUENCE: 56
gggcgcgggu gguugagcuu ggccaaaggc gccggacuuu aaauccgguu cuccacuggg      60 gagcguggu  ucaaauccca ccccgcgccc gcca                                 94

<210> SEQ ID NO 57
<211> LENGTH: 90
<212> TYPE: RNA
<213> ORGANISM: Artificial Sequence
<220> FEATURE:
<223> OTHER INFORMATION: Synthetic tRNA

<400> SEQUENCE: 57
ggcgcggugg uugagcuugg ccaaaggcgc cggacuugaa auccgguucu ccacugggga      60
gcggggguuc aaaucccucc cgcgccgcca                                      90

<210> SEQ ID NO 58
<211> LENGTH: 88
<212> TYPE: RNA
<213> ORGANISM: Artificial Sequence
<220> FEATURE:
<223> OTHER INFORMATION: Synthetic tRNA

<400> SEQUENCE: 58
ggcacugugg ccgagcgguu gaaggcaccg gucuugaaaa ccggcgaccc gaaagggguuc     60 cagaguucga aucucugcgg ugccgcca                                        88
```

COMPOSITIONS AND METHODS FOR MAKING SELENOCYSTEINE CONTAINING POLYPEPTIDES

CROSS-REFERENCE TO RELATED APPLICATIONS

This application is a 371 application of the International Application No. PCT/US2012/046252 entitled "Compositions and Methods for Making Selenocysteine Containing Polypeptides", filed in the United States Receiving Office for the PCT on Jul. 11, 2012, which claims the benefit of and priority to U.S. Provisional Application No. 61/506,338 filed Jul. 11, 2011, which are hereby incorporated herein by reference in their entirety.

STATEMENT REGARDING FEDERALLY SPONSORED RESEARCH OR DEVELOPMENT

This invention was made with government support under Agreement Nos. GM022854 awarded-by the National Institutes of Health, DE-FG02-98ER20311 awarded the Department of Energy and 0950474 awarded by the National Science Foundation. The government has certain rights in the invention.

REFERENCE TO SEQUENCE LISTING

The Sequence Listing submitted Jan. 7, 2014 as a text file named "YU_5714_ST25.txt," created on Dec. 30, 2013, and having a size of 15,578 bytes is hereby incorporated by reference pursuant to 37 C.F.R. §1.52(e)(5).

FIELD OF THE INVENTION

The field of the invention generally relates to compositions including recombinant tRNAs and methods of using them to manufacture recombinant selenocysteine containing polypeptides.

BACKGROUND OF THE INVENTION

Selenocysteine, commonly referred to as the twenty-first amino acid, is incorporated into at least 25 human proteins. Natural co-translational incorporation of selenocysteine (Sec) into proteins proceeds by a recoding process so that upon encountering the UGA codon in the messenger RNA the ribosome knows to recognize it as Sec instead of Stop. This process requires three components: (i) the aminoacyl-tRNA carrying selenocysteine, Sec-tRNA$^{Sec}$; (ii) the specialized elongation factor, SelB, carrying Sec-tRNA$^{Sec}$ to the ribosome, and (iii) the SECIS element, an RNA secondary structure of the mRNA just downstream of the UGA codon, that interacts with the SelB●Ser-tRNA$^{Sec}$ complex (Böck, A, Thanbichler, M, Rother, M & Resch, A (2005), eds Ibba M, Franklyn C S, & Cusack S (Landes Bioscience, Georgetown, Tex.), pp 320-327; Yoshizawa, S & Böck, A (2009) Biochim Biophys Acta 1790:1404-1414). Additionally, in order to protect the integrity of this recoding process, Sec-tRNA$^{Sec}$ is not recognized by the general elongation factor EF-Tu because of the presence of three base pairs that act as antideterminants (Rudinger, J, Hillenbrandt, R, Sprinzl, M & Giegé, R (1996) EMBO J 15:650-657. Sec-tRNA$^{Sec}$ cannot be accommodated during normal translation because it is not an acceptable substrate for EF-Tu, and the SelB●Sec-tRNA$^{Sec}$ complex will not decode in-frame UGA codons in absence of the SECIS.

Insertion of selenocysteine into a recombinant protein, for example, substitution of a naturally occurring cysteine residue for selenocysteine, can alter the function of the protein. Substituting one or more naturally occurring Cys residues in the active site of an enzyme with a Sec can increase the activity of this enzyme. Diselenide bonds have very low redox potential. Therefore, replacing disulfide bonds with diselenide or selenocysteine-cysteine bonds can lower dosage, increase half-life, increase stability, reduce toxicity, alter pharmacokinetics, change folding properties, or combinations thereof of the recombinant selenocysteine containing protein relative to a reference protein without selenocysteines, such as a naturally occurring counterpart.

However, due the presence the SECIS element as an integral part of the open reading frame (within the mRNA) encoding the protein that harbors Sec in its sequence, it is not possible to insert Sec into proteins by a standard mutational scheme or in the construction of random mutagenic libraries, and production of Sec proteins is limited to costly and inefficient methods of protein synthesis. Accordingly, there is a need for alternative methods of manufacturing selenocysteine containing polypeptides.

It is an object of the invention to provide compositions and methods for recombinant expression of proteins engineered to include one or more selenocysteine residues without the requirement of a SECIS in the mRNA encoding the protein.

It is a further object of the invention to provide non-naturally occurring proteins including one or more selenocysteine residues.

SUMMARY OF THE INVENTION

Non-naturally occurring tRNA$^{Sec}$ and methods of using them for recombinant expression of proteins engineered to include one or more selenocysteine residues are disclosed. Typically, the non-naturally occurring tRNA$^{Sec}$ (1) can be recognized by SerRS and by EF-Tu, or variants thereof; and is characterized by one or more of the following elements: (2) when aminoacylated with serine, the non-naturally occurring Ser-tRNA$^{Sec}$ can be converted to non-naturally occurring Sec-tRNA$^{Sec}$ by SelA, or variant thereof; (3) when aminoacylated with serine, the non-naturally occurring Ser-tRNA$^{Sec}$ can be phosphorylated by PSTK or variant thereof; (4) when aminoacylated with phosphorylated serine, the non-naturally occurring Sep-tRNA$^{Sec}$ can serve as a substrate for SepSecS or variant thereof; and combinations thereof. In some embodiments, the non-naturally occurring Ser-tRNA$^{Sec}$ is characterized by elements (1) and (2). In some embodiments, the non-naturally occurring Ser-tRNA$^{Sec}$ is characterized by elements (1), (3), and (4). In some embodiments, the non-naturally occurring Ser-tRNA$^{Sec}$ is characterized by elements (1), (2), (3), and (4). In some embodiments, the non-naturally occurring Ser-tRNA$^{Sec}$ is characterized by elements (1), (2), and (3).

The non-naturally occurring tRNA$^{Sec}$ do not require a SECIS element in an mRNA to be incorporated into a growing polypeptide chain during translation. Typically the anticodon of the non-naturally occurring tRNA$^{Sec}$ is recognized or hybridizes to a stop codon.

Methods of manufacturing selenocysteine containing polypeptides are also disclosed. The non-naturally occurring tRNA$^{Sec}$ can be used for recombinant manufacture of selenocysteine containing polypeptides encoded by mRNA without the requirement of an SECIS element. In some embodiments, the non-naturally occurring tRNA$^{Sec}$ is co-expressed in a recombinant expression system, such as *E.* coli, with SerRS, EF-Tu, SelA, or PSTK and SepSecS, or a combination of SelA, PSTK and SepSecS, and an mRNA with at least one codon that recognizes the anticodon of the non-naturally occurring tRNA$^{Sec}$ to manufacture a selenocyteine containing polypeptide encoded by the mRNA.

Nucleic acids encoding selenocysteine containing polypeptides are also disclosed. The nucleic acids encode a polypeptide of interest and include a non-natural tRNA$^{Sec}$ recognition codon, for example a "stop" codon, that hybridizes with the anticodon of the non-naturally occurring tRNA$^{Sec}$, such that a selenocyteine is transferred onto the growing polypeptide chain during translation. The selenocysteine containing polypeptides can be polypeptides that contain selenocysteine in nature, or polypeptides that do not contain selenocysteine in nature. For example, a non-naturally occurring tRNA recognition codon can be substituted for a cysteine codon in the naturally occurring mRNA, which changes the cysteine to a selenocysteine when the nucleic acid encoding the polypeptide is expressed recombinantly with the non-naturally occurring tRNA$^{Sec}$. Substituting one or more naturally occurring Cys residues with a Sec can increase activity, lower dosage, reduce toxicity, improve stability, increase efficacy, increase half-life or combinations thereof of a selenocysteine containing protein relative to its cysteine containing counterpart.

Methods of treating subjects in need thereof with recombinant selenocysteine containing polypeptides prepared using the disclosed compositions and methods are also disclosed. Particularly preferred proteins containing selenocystein include antibodies and enzymes having altered binding affinity and/or pharmacokinetics.

DETAILED DESCRIPTION OF THE INVENTION

I. Definitions

Figure 1B:
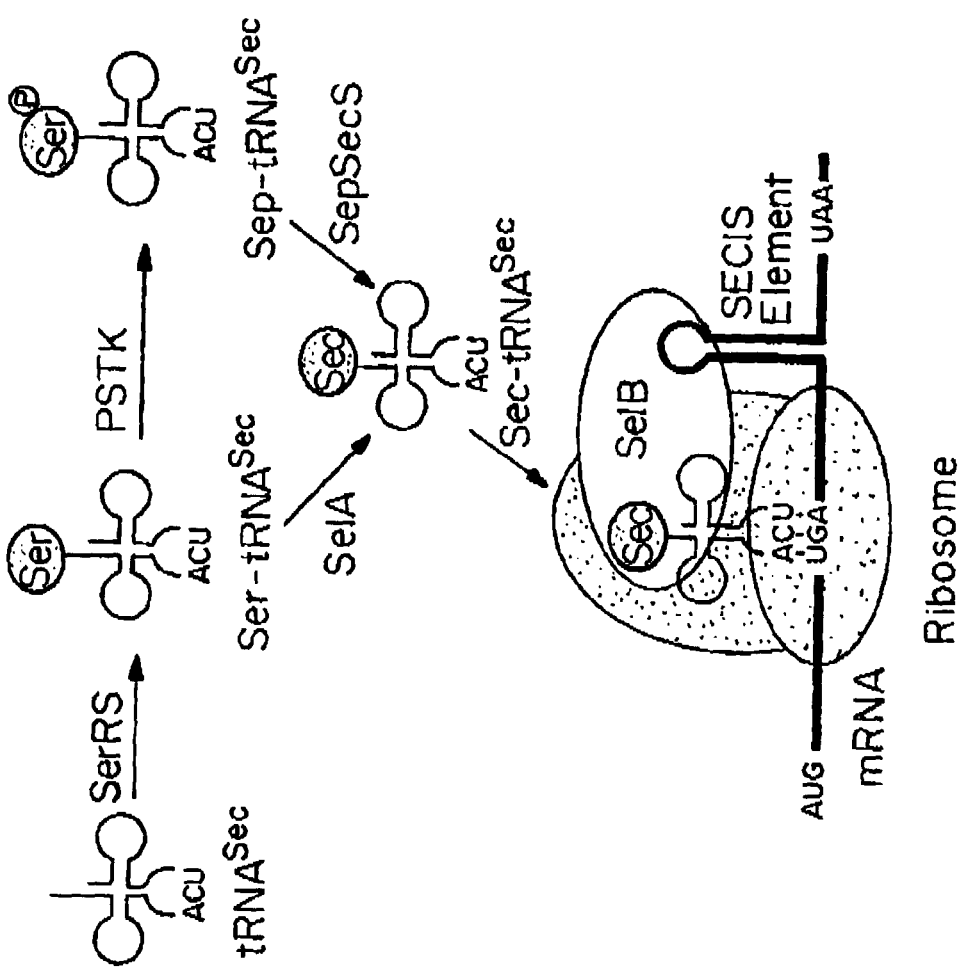
FIG. 1 is an illustration showing the Sec translation apparatus. The canonical amino acids are charged onto their respective tRNA by their cognate aminoacyl-tRNA synthetase. The aminoacyl-tRNA is then delivered by EF-Tu to the ribosome (FIG. 1A). In contrast, the Sec pathway requires several biosynthetic steps. First, tRNA$^{Sec}$ is misacylated to Ser-tRNA$^{Sec}$ by SerRS. While in bacteria Ser-tRNA$^{Sec}$ is directly converted by SelA to Sec-tRNA$^{Sec}$, archaea and eukaryotes employ an additional phosphorylation step by PSTK to form Sep-tRNA$^{Sec}$, which is then converted by SepSecS to the final product Sec-tRNA$^{Sec}$ (FIG. 1B). Sec-tRNA$^{Sec}$ is bound by elongation factor SelB and delivered to the ribosome. However, reassignment of the opal codon UGA to a Sec codon is only achieved if SelB also binds to the mRNA SECIS hairpin structure.

Transfer RNA or tRNA refers to a set of genetically encoded RNAs that act during protein synthesis as adaptor molecules, matching individual amino acids to their corresponding codon on a messenger RNA (mRNA). In higher eukaryotes such as mammals, there is at least one tRNA for each of the 20 naturally occurring amino acids. In eukaryotes, including mammals, tRNAs are encoded by families of genes that are 73 to 150 base pairs long. tRNAs assume a secondary structure with four base paired stems known as the cloverleaf structure. The tRNA contains a stem and an anticodon. The anticodon is complementary to the codon specifying the tRNA's corresponding amino acid. The anticodon is in the loop that is opposite of the stem containing the terminal nucleotides. The 3' end of a tRNA is aminoacylated by a tRNA synthetase so that an amino acid is attached to the 3'end of the tRNA. This amino acid is delivered to a growing polypeptide chain as the anticodon sequence of the tRNA reads a codon triplet in an mRNA.

As used herein "suppressor tRNA" refers to a tRNA that alters the reading of a messenger RNA (mRNA) in a given translation system. For example, a suppressor tRNA can read through a stop codon.

As used herein, an "anticodon" is any combination of 2, 3, 4, and 5 bases (G or A or U or C) that are complementary to a "stop codon" of equivalent and complementary base composition. Known "stop codons" include, but are not limited to, the three codon bases, UAA known as ochre, UAG known as amber and UGA known as opal that do not code for an amino acid but act as signals for the termination of protein synthesis. Generally the anticodon loop consists of seven nucleotides. In the 5' to 3' direction the first two positions 32 and 33 precede the anticodon positions 34 to 36 followed by two nucleotides in positions 37 and 38 (Alberts, B., et al. in *The Molecular Biology of the Cell*, 4$^{th}$ ed, Garland Science, New York, N.Y. (2002)). The size and nucleotide composition of the anticodon is generally the same as the size of the codon with complementary nucleotide composition. A four base pair codon consists of four bases such as 5'-AUGC-3' and an anticodon for such a codon would complement the codon such that the tRNA contained 5'-GCAU-3' with the anticodon starting at position 34 of the tRNA. A 5 base codon 5'-CGGUA-3' codon is recognized by the 5'-UACCG-3' anticodon (Hohsaka T., et al, *Nucleic Acids Res.* 29:3646-3651 (2001)). The composition of any such anticodon for 2 (16=any possible combination of 4 nucleotides), 3 (64), 4 (256), and 5 (1024) base codons would follow the same logical composition. The "anticodon" typically starts at position 34 of a canonical tRNA, but may also reside in any position of the "anti-codon stem-loop" such that the resulting tRNA is complementary to the "stop codon" of equivalent and complementary base composition.

As used herein, "tRNA$^{Sec}$" refers to an unaminoacylated tRNA suitable for carrying selenocysteine. Typically the anticodon sequence of the tRNA$^{Sec}$ can recognize or hybridize with an mRNA codon specific for, or designed to encode, a selenocysteine amino acid, for example UGA. In *E. coli*, the endogenous tRNA$^{Sec}$ is encoded by the selC gene.

As used herein, "tRNA$^{Ser}$" refers to an unaminoacylated tRNA suitable for carrying serine. Typically the anticodon sequence of the tRNA$^{Ser}$ can recognize or hybridize with an mRNA codon specific for, or designed to encode, a serine amino acid, for example UCU, UCC, UCA, UCG, AGU, or AGC.

As used herein, "tRNA$^{UTu}$" refers to a non-naturally occurring, unaminoacylated tRNA$^{Sec}$ suitable for carrying selenocysteine. Typically the anticodon sequence of the tRNA$^{UTu}$ can recognize or hybridize with an mRNA codon specific for, or designed to encode, a selenocysteine amino acid.

As used herein, "Sec-tRNA$^{Sec}$" refers to aminoacylated tRNA$^{Sec}$ carrying a selenocysteine amino acid.

As used herein, "Ser-tRNA$^{Sec}$" refers to aminoacylated tRNA$^{Sec}$ carrying a serine amino acid.

As used herein, "Ser-tRNA$^{Ser}$" refers to aminoacylated tRNA$^{Ser}$ carrying a serine amino acid.

As used herein, "Sep-tRNA$^{Ser}$" refers to a phosphorylated Ser-tRNA$^{Sec}$.

As used herein, "EF-Tu" refers to Elongation Factor Thermo Unstable, a prokaryotic elongation factor mediates the entry of the aminoacyl-tRNA into a free site of the ribosome.

As used herein, "SerRS" refers to Seryl-tRNA synthetase (also known as Serine—tRNA ligase) which is a prokaryotic factor that catalyzes the attachment of serine to tRNA$^{Ser}$.

As used herein "SECIS" refers to a SElenoCysteine Insertion Sequence, is an RNA element around 60 nucleotides in length that adopts a stem-loop structure which directs the cell to translate UGA codons as selenocysteines. In bacteria the SECIS can be soon after the UGA codon it affects, while in archaea and eukaryotes, it can be in the 3' or 5' UTR of an mRNA, and can cause multiple UGA codons within the mRNA to code for selenocysteine.

As used herein "SelA" refers to selenocysteine synthase, a prokaryotic pyridoxal 5-phosphate-containing enzyme which catalyzes the conversion of Ser-tRNA$^{Sec}$ into a Sec-tRNA$^{Sec}$.

As used herein "SelB" refers to selenocysteine-specific elongation factor, a prokaryotic elongation factor for delivery of Sec-tRNA$^{Sec}$ to the ribosome.

As used herein "PSTK" refers to phosphoseryl-tRNA kinase (also known as O-phosphoseryl-tRNA$^{Sec}$ kinase and L-seryl-tRNA$^{Sec}$ kinase), a kinase that phosphorylates Ser-tRNA$^{Sec}$ to O-phosphoseryl-tRNA$^{Sec}$, an activated intermediate for selenocysteine biosynthesis.

As used herein "SepSecS" refers to Sep (O-phosphoserine) tRNA:Sec (selenocysteine) tRNA synthase (also known as O-phosphoseryl-tRNA(Sec) selenium transferase and Sep-tRNA:Sec-tRNA synthase), an eukaryotic and archaeal enzyme that converts O-phosphoseryl-tRNA$^{Sec}$ to selenocysteinyl-tRNA$^{Sec}$ in the presence of a selenium donor.

As used herein SepCysS refers to Sep-tRNA:Cys-tRNA synthase, an archaeal/eukaryotic enzyme that converts O-phosphoseryl-tRNA (Sep-tRNA$^{Cys}$) into Cys-tRNA$^{Cys}$ in the presence of a sulfur donor.

As used herein "G-C content" (or guanine-cytosine content) refers to the percentage of nitrogenous bases on a nucleic acid molecule, or fragment, section, or region thereof, that are either guanine or cytosine.

Aminoacyl-tRNA Synthetases ("AARS") are enzymes that charge (acylate) tRNAs with amino acids. These charged aminoacyl-tRNAs then participate in mRNA translation and protein synthesis. The AARS show high specificity for charging a specific tRNA with the appropriate amino acid, for example, tRNA$^{Val}$ with valine by valyl-tRNA synthetase or tRNA$^{Trp}$ with tryptophan by tryptophanyl-tRNA synthetase. In general, there is at least one AARS for each of the twenty amino acids.

As used herein "translation system" refers to the components necessary to incorporate a naturally occurring amino acid into a growing polypeptide chain (protein). Components of a translation system can include, e.g., ribosomes, tRNAs, synthetases, mRNA and the like. The components described herein can be added to a translation system, in vivo or in vitro. A translation system can be either prokaryotic, e.g., an *E. coli* cell, or eukaryotic, e.g., a yeast, mammal, plant, or insect or cells thereof.

A "transgenic organism" as used herein, is any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation. Techniques for transferring DNA into such organisms are widely known and provided in references such as Sambrook, et al. (2000) Molecular Cloning: A Laboratory Manual, 3$^{rd}$ ed., vol. 1-3, Cold Spring Harbor Press, Plainview N.Y.

As used herein, the term "eukaryote" or "eukaryotic" refers to organisms or cells or tissues derived therefrom belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "non-eukaryotic organism" refers to organisms including, but not limited to, organisms of the Eubacteria phylogenetic domain, such as *Escherichia coli, Thermus thermophilus*, and *Bacillus stearothermophilus*, or organisms of the Archaea phylogenetic domain such as, *Methanocaldococcus jannaschii, Methanothermobacter thermautotrophicus, Halobacterium* such as *Haloferax volcanii* and *Halobacterium* species NRC-1, *Archaeoglobus fulgidus, Pyrococcus furiosus, Pyrococcus horikoshii*, and *Aeuropyrum pernix.*

The term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "orthologous genes" or "orthologs" refer to genes that have a similar nucleic acid sequence because they were separated by a speciation event.

The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Cofactor", as used herein, refers to a substance, such as a metallic ion or a coenzyme that must be associated with an enzyme for the enzyme to function. Cofactors work by changing the shape of an enzyme or by actually participating in the enzymatic reaction.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide May be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5);

methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Set), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences The term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

"Transformed," "transgenic," "transfected" and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

The term "endogenous" with regard to a nucleic acid refers to nucleic acids normally present in the host.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods. For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

The term "stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Third Edition, Cold Spring Harbor, N.Y. (2000).

As used herein, the term "low stringency" refers to conditions that permit a polynucleotide or polypeptide to bind to another substance with little or no sequence specificity.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

Unless otherwise indicated, the disclosure encompasses conventional techniques of molecular biology, microbiology, cell biology and recombinant DNA, which are within the skill of the art. See, e.g., Sambrook and Russell, Molecular Cloning: A Laboratory Manual, 3rd edition (2001); Current Protocols In Molecular Biology [(F. M. Ausubel, et al. eds., (1987)]; Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)].

Unless otherwise noted, technical terms are used according to conventional usage. Definitions of common terms in molecular biology may be found in Lewin, Genes VII, published by Oxford University Press, 2000; Kendrew et al. (eds.), The Encyclopedia of Molecular Biology, published by Wiley-Interscience., 1999; and Robert A. Meyers (ed.), Molecular Biology and Biotechnology, a Comprehensive Desk Reference, published by VCH Publishers, Inc., 1995; Sambrook and Russell. (2001) Molecular Cloning: A Laboratory Manual 3rd. edition, Cold Spring Harbor Laboratory Press.

II. Compositions

A. tRNA

Non-naturally occurring tRNA$^{Sec}$ suitable for carrying selenocysteine and facilitating synthesis of selenopeptides without requiring a SECIS in the mRNA encoding the peptide are disclosed. Also disclosed are aminoacylated non-naturally occurring tRNA$^{Sec}$. Using the methods discussed in more detail below, the tRNA$^{Sec}$ disclosed herein are capable of being aminoacylated to form a Sec-tRNA$^{Sec}$ which can facilitate insertion of selenocysteine into nascent polypeptide chains. Typically, the non-naturally occurring tRNA$^{Sec}$ (1) can be recognized by SerRS and by EF-Tu, or variants thereof; and is characterized by one or more of the following elements: (2) when aminoacylated with serine the non-naturally occurring Ser-tRNA$^{Sec}$ can be converted to non-naturally occurring Sec-tRNA$^{Sec}$ by SelA, or variant thereof; (3) when aminoacylated with serine the non-naturally occurring Ser-tRNA$^{Sec}$ can be phosphorylated by PSTK or variant thereof; (4) when aminoacylated with phosphorylated serine the non-naturally occurring Sep-tRNA$^{Sec}$ can serve as a substrate for SepSecS or variant thereof; and combinations thereof. In some embodiments, the non-naturally occurring tRNA$^{Sec}$ is characterized by elements (1) and (2). In some embodiments, the non-naturally occurring tRNA$^{Sec}$ is characterized by elements (1), (3), and (4). In some embodiments, the non-naturally occurring tRNA$^{Sec}$ is characterized by elements (1), (2), (3), and (4). Typically, the non-naturally occurring Sec-tRNA$^{Sec}$ can be bound by EF-Tu. The Sec can be incorporated into a growing peptide chain at a codon of the mRNA that recognizes the anticodon of the tRNA$^{Sec}$. Preferably, EF-Tu does not bind Sep-tRNA$^{Sec}$. In some embodiments, EF-Tu is less efficient at incorporating Ser-tRNA$^{Sec}$ than Sec-tRNA$^{Sec}$ into the growing peptide chain.

The non-naturally occurring tRNA$^{Sec}$ do not require a SECIS element in an mRNA to be incorporated into a growing polypeptide chain during translation. Typically the anticodon of the non-naturally occurring tRNA$^{Sec}$ is recognized or hybridizes to a stop codon. Typically the non-naturally occurring tRNA$^{Sec}$ can facilitate incorporation of a Sec into a growing peptide chain without the activity of SelB.

1. Substrates for EF-Tu

EF-Tu is a prokaryotic elongation factor that mediates the entry of the aminoacyl-tRNA into a free site of the ribosome. Endogenous prokaryotic tRNAs, typically include an antideterminant element, which prevents recognition of a Sec-tRNA$^{Sec}$ by the elongation factor EF-Tu. In some embodiments, the disclosed tRNA can be a substrate for EF-Tu. Therefore, in some embodiments, the disclosed tRNA is a variant of an endogenous tRNA$^{Sec}$ that has been modified to inactivate the antideterminant element. The antideterminant element can be modified, mutated, or deleted so that tRNA is an acceptable substrate for EF-Tu. For example the antideterminant element in *E. coli* tRNA$^{Sec}$ is located in the 8th, 9th and 10th bp in the acceptor branch of tRNA$^{Sec}$ (encoded by selC), corresponding to the last base pair in the amino acid acceptor stem and the two first pairs in the T-stem (Rudinger, et al., *EMBO J.*, 15(3):650-57 (1996), and can be referred to as C7●G66/G49●U65/C50●G64 according the numbering in Schon, et al., *Nucleic Acids Res.*, 17(18):7159-7165 (1989). Accordingly, in some embodiments, the non-naturally occurring tRNA$^{Sec}$ is a naturally occurring tRNA$^{Sec}$ where the corresponding antideterminant sequence is mutated or deleted such that the non-naturally occurring tRNA$^{Sec}$ is a substrate for EF-Tu.

2. Substrates for PSTK

PSTK is a kinase in archaeal and eukaryotic systems that phosphorylates Ser-tRNA$^{Sec}$ to O-phosphoseryl-tRNA$^{Sec}$, an activated intermediate for selenocysteine biosynthesis. Accordingly, in some embodiments, once aminoacylated with serine, the non-naturally occurring tRNA can serve as a substrate for a PSTK, or variant thereof. The enzyme activity of PSTK is strictly tRNA$^{Sec}$-dependent. PSTK does not hydrolyze ATP in the absence of tRNA nor in the presence of Ser-tRNA$^{Ser}$. The binding of tRNA$^{Ser}$, however, promotes ATP hydrolysis (R. Lynn Sherrer, et al., *Nucleic Acids Res.*, 36(4): 1247-1259 (2008)). This indicates that tRNA$^{Sec}$ might play an essential role in positioning the Ser moiety for initiating phosphoryl transfer. Compared to aminoacyl-tRNA synthetases, PSTK has approximately 20-fold higher affinity toward its substrate, Ser-tRNA$^{Sec}$ (Km=40 nM) (R. Lynn Sherrer, et al., *Nucleic Acids Res.,* 36(4): 1247-1259 (2008)), which may compensate for the low abundance of tRNA$^{Sec}$ in vivo. The concentration of tRNA$^{Sec}$ in vivo is at least 10-fold lower than tRNA$^{Ser}$ in tRNA$^{Sec}$-rich tissues such as liver, kidney and testes in rat (Diamond, et al., *J. Biol. Chem.,* 268:14215-14223 (1993)).

The crystal structure of *Methanocaldococcus jannaschii* PSTK (MjPSTK) places archaeal PSTK identity elements (G2:C71 and the C3:G70) (Sherrer, et al., *Nucleic Acids Res,* 36:1871-1880 (2008)). within contact of the protein dimer interface. The second base pair in the acceptor stem is highly conserved as C2:G71 in eukaryotic tRNA$^{Sec}$, and mutation of G2:C71 to C2:G71 in archaeal tRNA$^{Sec}$ resulted in a Ser-tRNA$^{Sec}$ variant that is phosphorylated inefficiently (Sherrer, et al., *Nucleic Acids Res,* 36:1871-1880 (2008). The A54.368 base pair in *Methanococcus maripaludis* tRNA$^{Ser}$ has some antideterminant properties for PSTK (Sherrer, et al., *NAR,* 36(6):1871-1880 (2008)). Moreover, the eukaryotic PSTK has been reported to recognize the unusual D-arm of tRNA$^{Sec}$ as the major identity element for phosphorylation (Wu and Gross *EMBO J.,* 13:241-248 (1994)). Accordingly, in some embodiments, the disclosed tRNAs include residues in the acceptor stem, the D-arm, or combinations thereof that are necessary for the tRNA to serve as a substrate for a PSTK.

3. Substrate for SepSecS

The conversion of phosphoseryl-tRNA$^{Sec}$ (Sep-tRNA$^{Sec}$) to selenocysteinyl-tRNA$^{Sec}$ (Sec-tRNA$^{Sec}$) is the last step of Sec biosynthesis in both archaea and eukaryotes, and it is catalyzed by tetratmeric O-phosphoseryl-tRNA:selenocysteinyl-tRNA synthase (SepSecS). It is believed that one SepSecS homodimer interacts with the sugar-phosphate backbone of both the acceptor-TΨC and the variable arms of tRNA$^{Sec}$, while the other homodimer interacts specifically with the tip of the acceptor arm through interaction between the conserved Arg398 and the discriminator base G73 of human tRNA$^{Sec}$.

The co-crystal structure of SepSecS and tRNA$^{Sec}$ also suggests that the 9 by acceptor stem of tRNA$^{Sec}$ is probably important for recognition by the enzyme (Palioura, S, Sherrer, R L, Steitz, T A, Söll, D & Simonovic, M (2009) *Science* 325:321-325). According to structural analysis, the acceptor-T-variable arm elbow region of tRNA$^{Sec}$ (including bases G50, G51, C64, C65 in the human tRNA$^{Sec}$ that are recognized by SepSecS) may be critical for recognition by SepSecS. Accordingly, in some embodiments, the disclosed tRNAs include residues in the acceptor-TΨC, the variable arms of tRNA$^{Sec}$, the tip of the acceptor arm, or combinations thereof necessary for the tRNA to serve as a substrate for SepSecS. In some embodiments, the G50, G51, C64, C65 elements of human tRNA$^{Sec}$ are present in the non-naturally occurring tRNA$^{Sec}$.

The SepSecS enzyme itself can also be mutated to engineer enzyme variants that accept a substrate somewhat less ideal than naturally occurring tRNA$^{Sec}$. It is believed that His30, Arg33, Lys38 in SepSecS form key interactions with the protomer and G50, U51, C64 and C65 of the tRNA. Therefore, mutation of some of these residues could result in a SepSecS variant that is better able to recognize one of the non-naturally occuring tRNA$^{Sec}$. The formed Sec-tRNA$^{Sec}$ can be screened in the formate dehydrogenase-benzyl viologen assay [e.g., (Yuan, J, Palioura, S, Salazar, J C, Su, D, O'Donoghue, P, Hohn, M J, Cardoso, A M, Whitman, W B & Söll, D (2006), *Proc Natl Acad Sci USA* 103:18923-18927; Palioura, S, Sherrer, R L, Steitz, T A, Söll, D & Simonovic, M (2009) *Science* 325:321-325)]. Other assays include standard Wolfson assay [e.g., (Yuan, J, Palioura, S, Salazar, J C, Su, D, O'Donoghue, P, Hohn, M J, Cardoso, A M, Whitman, W B & Söll, D (2006) *Proc Natl Acad Sci USA* 103:18923-18927; Palioura, S, Sherrer, R L, Steitz, T A, Söll, D & Simonovic, M (2009) *Science* 325:321-325)], labeling with [75Se]selenite in the presence of selenophosphate synthase (SelD) [e.g., (Yuan, J, Palioura, S, Salazar, J C, Su, D, O'Donoghue, P, Hohn, M J, Cardoso, A M, Whitman, W B & Söll, D (2006) *Proc Natl Acad Sci USA* 103:18923-18927)], and using [14C] or [3H]serine in the initial charging reaction.

Figure 2:
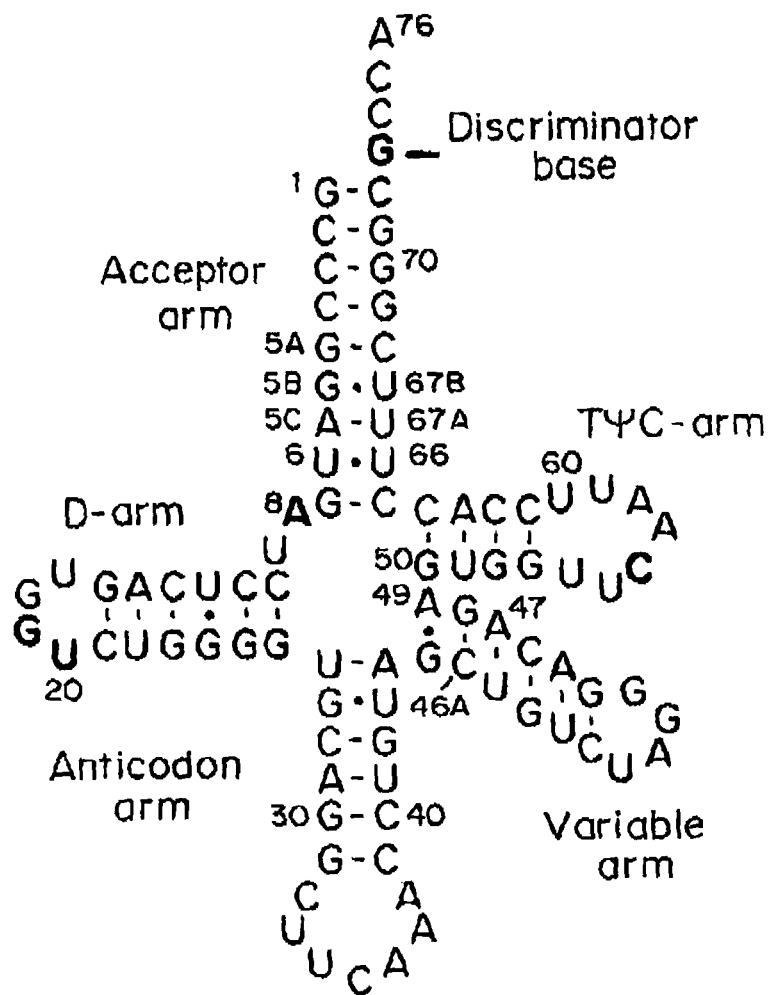
FIG. 2 is a depiction of the primary and secondary structures of human tRNA$^{Sec}$ (SEQ ID NO:3) adapted from Yuan, et al., *FEBS Lett.*, 584(2):342-349 (2010).

In some embodiments, a SepCysS is used instead of SepSecS. SepCysS is a key PLP-dependent enzyme in Cys-tRNA formation in methanogens. It converts Sep-tRNA$^{Cys}$ into Cys-tRNA$^{Cys}$ using thiophosphate as sulfur donor. The enzyme's crystal structure is established (Fukunaga, R & Yokoyama, S (2007) *Nat Struct Mol Biol* 14:272-279.) and its mechanism (Liu, Y., Dos Santos, P. C., Zhu, X., Orlando, R., Dean, D. R., Söll, D. and Yuan, J. (2012) *J. Biol. Chem.* 287, 5426-5433) is different from that of SepSecS (Palioura, S, Sherrer, R L, Steitz, T A, Söll, D & Simonovic, M (2009) *Science* 325:321-325.). The length of the acceptor stem of its tRNA substrates is not critical and acceptor helices between 7-9 bp are acceptable. Therefore, this enzyme's active site can be engineered to allow selenophosphate (instead of thiophosphate) to participate in the reaction. 4. Primary Structure tRNAs can be described according to their primary structure (i.e., the sequence from 5' to 3') as well as their secondary structure. The secondary structure of tRNA is typically referred to as a "cloverleaf", which assumes a 3D L-shaped tertiary structure through coaxial stacking of the helices. FIG. 2 illustrates a typical human tRNA$^{Sec}$, which includes an acceptor arm, a D-arm, an anticodon arm, a variable arm, and a TΨC-arm.

In some embodiments the non-naturally occurring tRNA$^{Sec}$ shares sequence identity or sequence homology with a naturally occurring tRNA, for example a naturally occurring tRNA$^{Sec}$, or a naturally occurring tRNA$^{Ser}$.

a. Variants of Naturally Occurring tRNA$^{Sec}$

The non-naturally occurring tRNA$^{Sec}$ disclosed herein can be a variant of a naturally occurring tRNA$^{Sec}$. The naturally occurring tRNA$^{Sec}$ can be from a prokaryote, including but not limited to *E. coli*, an archaea, including, but not limited to, *M. maripaludis* and *M. jannaschii*, or a eukaryote including, but not limited to human.

Figure 3:
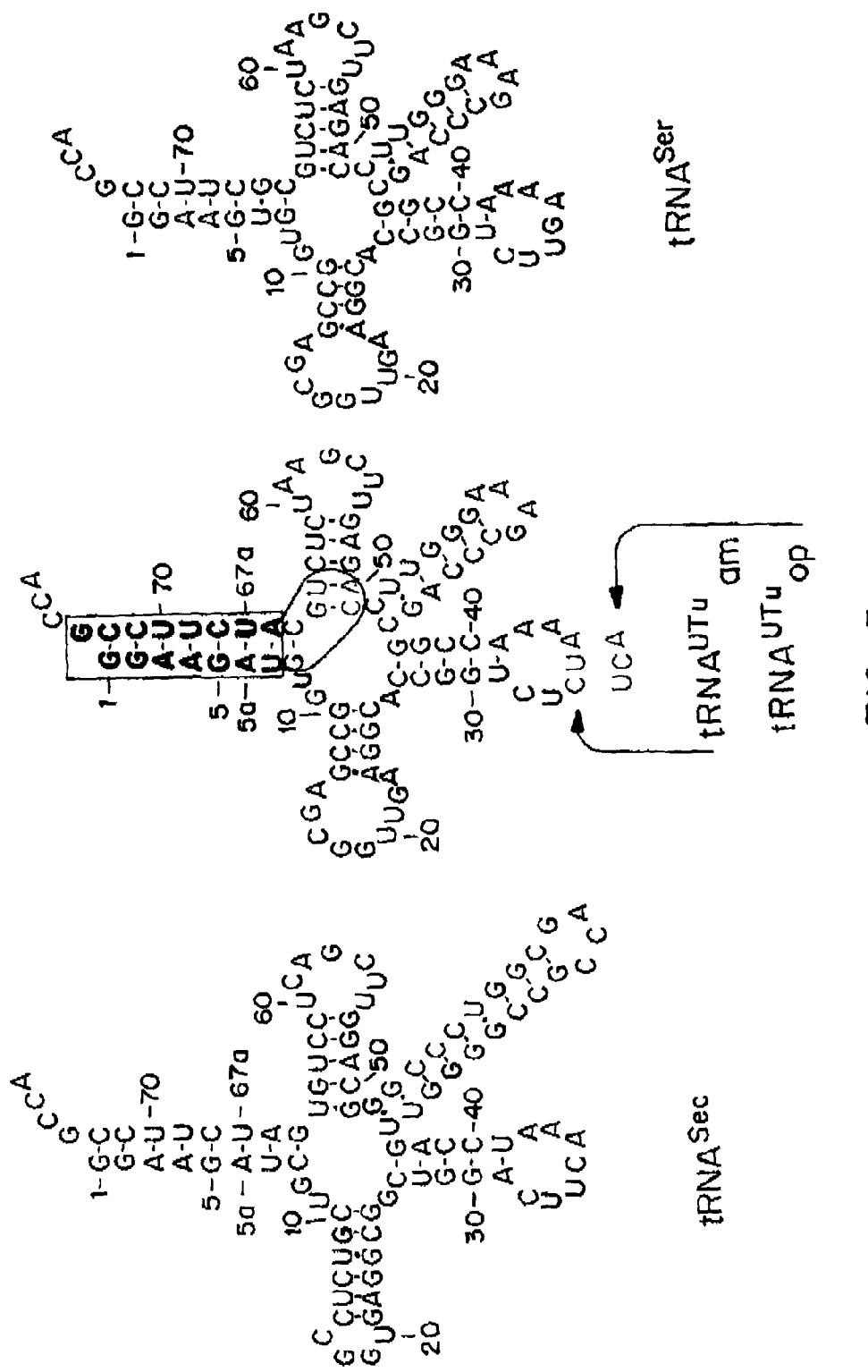
FIG. 3 is a depiction of the primary and secondary structures of *E. coli* tRNA$^{Sec}$ (left, SEQ ID NO:1), a non-naturally occurring tRNA$^{UTu}$ with an *E. coli* body (center, (tRNA$^{UTu}_{op}$, SEQ ID NO:6; tRNA$^{UTu}_{am}$, SEQ ID NO:7), and *E. coli* tRNA$^{Ser}$ (right. SEQ ID NO:4). *E. coli* tRNA$^{Ser}$ (right) serves as a major scaffold for tRNA$^{UTu}$ (center) with the exception of the acceptor stem that originates from *E. coli* tRNA$^{Sec}$ (boxed sequence elements). Major EF-Tu recognition elements were retained from tRNA$^{Ser}$ as well (circled sequence elements). Substitution of the amber anti-codon CUA (tRNA$^{UTu}_{am}$) for the opal anti-codon UCA (tRNA$^{UTu}_{op}$) are depicted with arrows and labeling.

In some embodiments, the non-naturally occurring tRNA$^{Sec}$ is a variant of an *E. coli* tRNA$^{Sec}$, for example, GGAAGAUCGUCGUCUCCGGUGAGGCGGCUGGAC-UUCAAAUCCA GUUGGGGCCGCCAGCGGUC-CCGGGCAGGUUCGACUCCUGUGAUC UUCCGCCA (SEQ ID NO:1), which is depicted in FIG. 3 (left panel).

In some embodiments, the non-naturally occurring tRNA$^{Sec}$ is a variant of an *M. maripaludis* tRNA$^{Sec}$, for example, GGCACGGGGUGCUUAUCUUGGUA-GAUGAGGGCGGACUUCAGAU CCGUCGAGUUC-CGUUGGAAUUCGGGGUUCGAUUCCCCCCCUGCG CCGCCA (SEQ ID NO:2).

In some embodiments, the non-naturally occurring tRNA$^{Sec}$ is a variant of a human tRNA$^{Sec}$, for example, GCCCGGAUGAUCCUCAGUGGUCUGGGGUGCAG-GCUUCAAACCU GUAGCUGUCUAGGGACAGAGUG-GUUCAAUUCCACCUUUCGGGC GCCA (SEQ ID NO:3), which is depicted in FIG. 2, A non-naturally occurring tRNA$^{Sec}$ that is a variant of a naturally occurring tRNA$^{Sec}$ can have a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO:1, 2, or 3. Preferably the non-naturally occurring tRNA$^{Sec}$ that is a variant of a naturally occurring tRNA$^{Sec}$ is characterized by one or more of the following elements: (1) the non-naturally occurring tRNA$^{Sec}$ can be recognized by SerRS and by EF-Tu, or variants thereof; (2) when aminoacylated with serine the non-naturally occurring Ser-tRNA$^{Sec}$ can be converted to non-naturally occurring Sec-tRNA$^{Sec}$ by SelA or variant thereof; (3) when aminoacylated with serine the non-naturally occurring Ser-tRNA$^{Sec}$ can be phosphorylated by PSTK or variant thereof; (4) when aminoacylated with phosphorylated serine the non-naturally occurring Sep-tRNA$^{Sec}$ can serve as a substrate for SepSecS or variant thereof.

b. Variants of Naturally Occurring tRNA$^{Sec}$

The non-naturally occurring tRNASec disclosed herein can be a variant of a naturally occurring tRNA$^{Ser}$. The naturally occurring tRNA$^{Ser}$ can be from a prokaryote, including but not limited to E. coli, an archaea, including, but not limited to, M. maripaludis and M. jannaschii, or a eukaryote including, but not limited to human.

In some embodiments, the non-naturally occurring tRNA$^{Sec}$ is a variant of an E. coli tRNA$^{Ser}$, for example, GGAAGUGUGGCCGAGCGGUUGAAGGCACCGGUC-UUGAAAACCG GCGACCCGAAAGGGUUCCA-GAGUUCGAAUCUCUGCGCUUCCGCC A (SEQ ID NO:4), depicted in FIG. 3 (right panel).

In some embodiments, the non-naturally occurring tRNA$^{Sec}$ is a variant of an M. maripaludis tRNA$^{Ser}$, for example, GCAGAGGUGGUUGAGCUUGGC-CAAAGGCGCCGGACUUGAAAUC CGGUUCUCCA-CUGGGGAGCGGGGGUUCAAAUCCCUCCCUCUGCG CCA (SEQ ID NO:5).

A non-naturally occurring tRNA$^{Sec}$ that is a variant of a naturally occurring tRNA$^{Ser}$ can have a nucleic acid sequence at least 65%, 70%, 71%, 72%, 73%, 74%, 75%, 76%, 77%, 78%, 79%, 80%, 81%, 82%, 83%, 84%, 85%©, 86%, 87%, 88%, 89%, 90%, 91%, 92%, 93%, 94%, 95%, 96%, 97%, 98%, 99%, or more identical to SEQ ID NO:4 or 5. Preferably the non-naturally occurring tRNA$^{Sec}$ that is a variant of an E. coli tRNA$^{Ser}$ is characterized by one or more of the following elements: (1) the non-naturally occurring tRNA$^{Sec}$ can be recognized by SerRS and by EF-Tu, or variants thereof; (2) when aminoacylated with serine the non-naturally occurring Ser-tRNA$^{Sec}$ can be converted to non-naturally occurring Sec-tRNA$^{Sec}$ by SelA; (3) when aminoacylated with serine the non-naturally occurring Ser-tRNA$^{Sec}$ can be phosphorylated by PSTK or variant thereof; (4) when aminoacylated with phosphorylated serine the non-naturally occurring Sep-tRNA$^{Sec}$ can serve as a substrate for SepSecS or variant thereof.

c. Chimeric tRNA$^{Sec}$

The non-naturally occurring tRNA$^{Sec}$ disclosed herein can also be a chimeric tRNA including sequences from two or more naturally occurring tRNAs. Some embodiments, the non-naturally occurring tRNA includes sequences from a naturally occurring tRNA$^{Sec}$ and a naturally occurring tRNA$^{Ser}$. The chimeric tRNA can include nucleic acid sequences or features, for example an antideterminant element, from a prokaryote, including but not limited to E. coli, an archaea, including, but not limited to, M. maripaludis and M. jannaschii, or a eukaryote including, but not limited to, human.

i. E. coli Chimeras

Examples of non-naturally occurring tRNA$^{Sec}$ that are chimeric tRNAs including sequence elements from E. coli include, but are not limited to
GGAAGAUGUGGCCGAGCGGUUGAAGGCACCGGU-CUUCAAAACC GGCGACCCGAAAGGGUUCCA-GAGUUCGAAUCUCUGCAUCUUCC GCCA (SEQ ID NO:6; E. coli tRNA$^{UTu}$-opal), as depicted in FIG. 3 (center panel);
GGAAGAUGUGGCCGAGCGGUUGAAGGCACCGGU-CUCUAAAACC GGCGACCCGAAAGGGUUCCA-GAGUUCGAAUCUCUGCAUCUUCC GCCA (SEQ ID NO:7; E. coli tRNA$^{UTu}$-amber), as depicted in FIG. 3 (center panel); and
GGAAGAUGUGGCCGAGCGGUUGAAGGCACCGGU-CUUUAAAACC GGCGACCCGAAAGGGUUCCA-GAGUUCGAAUCUCUGCAUCUUCC GCCA (SEQ ID NO:8; E. coli tRNA$^{UTu}$-ochre).

Other examples of non-naturally occurring tRNA$^{Sec}$ that are chimeric tRNAs including sequence elements from E. coli include, but are not limited to
GGCACUGUGGCCGAGCGGUUGAAGGCACCGGUC-UUCAAAACCG GCGACCCGAAAGGGUUCCA-GAGUUCGAAUCUCUGCGGUGCCGCC A (SEQ ID NO:9; E. coli tRNA$^{UTu}$-opal), as depicted in FIG. 4B;
GGCACUGUGGCCGAGCGGUUGAAGGCACCGGU-CUCUAAAACCG GCGACCCGAAAGGGUUCCA-GAGUUCGAAUCUCUGCGGUGCCGCC A (SEQ ID NO:10; E. coli tRNA$^{UTu}$-amber), as depicted in FIG. 4B; and
GGCACUGUGGCCGAGCGGUUGAAGGCACCGGUC-UUUAAAACCG GCGACCCGAAAGGGUUCCA-GAGUUCGAAUCUCUGCGGUGCCGCC A (SEQ ID NO:11; E. coli tRNA$^{UTu}$-ochre), which are non-naturally occurring chimeras of E. coli tRNA$^{Ser}$ with PSTK identity elements.

In some embodiments, the non-naturally occurring tRNA$^{Sec}$ is a variant of SEQ ID NO:9 such as

```
(SEQ ID NO: 12; E. coli tRNAUTu-opal - variant 1)
GGGCACUGUGGCCGAGCGGUUGAAGGCACCGGUCUUCAAAACC
GGCGACCCGAAAGGGUUCCAGAGUUCGAAUCUCUGCGGUGCCC
GCCA;

(SEQ ID NO: 13; E. coli tRNAUTu-opal - variant 2)
GGCACUGGUGGCCGAGCGGUUGAAGGCACCGGUCUUCAAAACC
GGCGACCCGAAAGGGUUCCAGAGUUCGAAUCUCUGCCGGUGCC
GCCA;

(SEQ ID NO: 14; E. coli tRNAUTu-opal - variant 3)
GGCACUGUGGCCGAGCGGUUGAAGGCACCGGUCUUCAAAACCG
GCGACCCGAAAGGGUUCCUGAGUUCGAAUCUCAGCGGUGCCGCC
A;

(SEQ ID NO: 15; E. coli tRNAUTu-opal - variant 4)
GGGCACUGGUGGCCGAGCGGUUGAAGGCACCGGUCUUCAAAAC
CGGCGACCCGAAAGGGUUCCAGAGUUCGAAUCUCUGCCGGUGCC
CGCCA;

(SEQ ID NO: 16; E. coli tRNAUTu-opal - variant 5)
GGGCACUGUGGCCGAGCGGUUGAAGGCACCGGUCUUCAAAACC
GGCGACCCGAAAGGGUUCCUGAGUUCGAAUCUCAGCGGUGCCC
GCCA;

(SEQ ID NO: 17; E. coli tRNAUTu-opal - variant 6)
GGCACUGGUGGCCGAGCGGUUGAAGGCACCGGUCUUCAAAACC
GGCGACCCGAAAGGGUUCCUGAGUUCGAAUCUCAGCCGGUGCC
GCCA;
```

-continued or (SEQ ID NO: 18; E. coli tRNA$^{UTu}$-opal - variant 7)
GGGCACUGGUGGCCGAGCGGUUGAAGGCACCGGUCUUCAAAAC
CGGCGACCCGAAAGGGUUCCUGAGUUCGAAUCUCAGCCGGUGCC
CGCCA In some embodiments, the non-naturally occurring tRNA$^{Sec}$ is a variant of SEQ ID NO:10 such as (SEQ ID NO: 19; E. coli tRNA$^{UTu}$-amber - variant 1)
GGGCACUGUGGCCGAGCGGUUGAAGGCACCGGUCUCUAAAACC
GGCGACCCGAAAGGGUUCCAGAGUUCGAAUCUCUGCGGUGCCC
GCCA;

(SEQ ID NO: 20; E. coli tRNA$^{UTu}$-amber - variant 2)
GGCACUGGUGGCCGAGCGGUUGAAGGCACCGGUCUCUAAAACC
GGCGACCCGAAAGGGUUCCAGAGUUCGAAUCUCUGCCGGUGCC
GCCA;

(SEQ ID NO: 21; E. coli tRNA$^{UTu}$-amber - variant 3)
GGCACUGUGGCCGAGCGGUUGAAGGCACCGGUCUCUAAAACCG
GCGACCCGAAAGGGUUCCUGAGUUCGAAUCUCAGCGGUGCCGCC
A;

(SEQ ID NO: 22; E. coli tRNA$^{UTu}$-amber - variant 4)
GGGCACUGGUGGCCGAGCGGUUGAAGGCACCGGUCUCUAAAAC
CGGCGACCCGAAAGGGUUCCAGAGUUCGAAUCUCUGCCGGUGCC
CGCCA;

(SEQ ID NO: 23; E. coli tRNA$^{UTu}$-amber - variant 5)
GGGCACUGUGGCCGAGCGGUUGAAGGCACCGGUCUCUAAAACC
GGCGACCCGAAAGGGUUCCUGAGUUCGAAUCUCAGCGGUGCCC
GCCA;

(SEQ ID NO: 24; E. coli tRNA$^{UTu}$-amber - variant 6)
GGCACUGGUGGCCGAGCGGUUGAAGGCACCGGUCUCUAAAACC
GGCGACCCGAAAGGGUUCCUGAGUUCGAAUCUCAGCCGGUGCC
GCCA;

(SEQ ID NO: 25; E. coli tRNA$^{UTu}$-amber - variant 7)
GGGCACUGGUGGCCGAGCGGUUGAAGGCACCGGUCUCUAAAAC
CGGCGACCCGAAAGGGUUCCUGAGUUCGAAUCUCAGCCGGUGCC
CGCCA;

In some embodiments, the non-naturally occurring tRNA$^{Sec}$ is a variant of SEQ ID NO:11 such as (SEQ ID NO: 26; E. coli tRNA$^{UTu}$-ochre - variant 1)
GGGCACUGUGGCCGAGCGGUUGAAGGCACCGGUCUUUAAAACC
GGCGACCCGAAAGGGUUCCAGAGUUCGAAUCUCUGCGGUGCCC
GCCA;

(SEQ ID NO: 27; E. coli tRNA$^{UTu}$-ochre - variant 2)
GGCACUGGUGGCCGAGCGGUUGAAGGCACCGGUCUUUAAAACC
GGCGACCCGAAAGGGUUCCAGAGUUCGAAUCUCUGCCGGUGCC
GCCA;

(SEQ ID NO: 28; E. coli tRNA$^{UTu}$-ochre - variant 3)
GGCACUGUGGCCGAGCGGUUGAAGGCACCGGUCUUUAAAACCG
GCGACCCGAAAGGGUUCCUGAGUUCGAAUCUCAGCGGUGCCGCC
A;

(SEQ ID NO: 29; E. coli tRNA$^{UTu}$-ochre - variant 4)
GGGCACUGGUGGCCGAGCGGUUGAAGGCACCGGUCUUUAAAAC
CGGCGACCCGAAAGGGUUCCAGAGUUCGAAUCUCUGCCGGUGCC
CGCCA;

(SEQ ID NO: 30; E. coli tRNA$^{UTu}$-ochre - variant 5)
GGGCACUGUGGCCGAGCGGUUGAAGGCACCGGUCUUUAAAACC
GGCGACCCGAAAGGGUUCCUGAGUUCGAAUCUCAGCGGUGCCC
GCCA;

(SEQ ID NO: 31; E. coli tRNA$^{UTu}$-ochre - variant 6)
GGCACUGGUGGCCGAGCGGUUGAAGGCACCGGUCUUUAAAACC
GGCGACCCGAAAGGGUUCCUGAGUUCGAAUCUCAGCCGGUGCC
GCCA;

or (SEQ ID NO: 32; E. coli tRNA$^{UTu}$-ochre - variant 7)
GGGCACUGGUGGCCGAGCGGUUGAAGGCACCGGUCUUUAAAAC
CGGCGACCCGAAAGGGUUCCUGAGUUCGAAUCUCAGCCGGUGCC
CGCCA A non-naturally occurring tRNA$^{Sec}$ that is a chimeric E. coli tRNA can have a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more identical to SEQ ID NO:6, 7, 8, 9, 10, 11, 12, 13, 14, 15, 16, 17, 18, 19, 20, 21, 22, 23, 24, 25, 26, 27, 28, 29, 30, 31, or 32. Preferably the non-naturally occurring tRNA$^{Sec}$ that is a chimeric E. coli tRNA$^{Sec}$ is characterized by one or more of the following elements: (1) the non-naturally occurring tRNA$^{Sec}$ can be recognized by SerRS and by EF-Tu, or variants thereof; (2) when aminoacylated with serine the non-naturally occurring Ser-tRNA$^{Sec}$ can be converted to non-naturally occurring Sec-tRNA$^{Sec}$ by SelA or variant thereof; (3) when aminoacylated with serine the non-naturally occurring Ser-tRNA$^{Sec}$ can be phosphorylated by PSTK or variant thereof; (4) when aminoacylated with phosphorylated serine the non-naturally occurring Sep-tRNA$^{Sec}$ can serve as a substrate for SepSecS or variant thereof.

ii. M. maripaludis Chimeras

Examples of non-naturally occurring tRNA$^{Sec}$ that are chimeric tRNAs including sequences elements from M. maripaludis include, but are not limited to, GGCGCGGUGGUUGAGCUUGGCCAAAGGCGCCG-GACUUCAAAUC CGGUUCUCCA-CUGGGGAGCGGGGGUUCAAAUCCCUC-CCGCGCCG CCA (SEQ ID NO:33; M. maripaludis tRNA$^{UTu}$-opal), as depicted in FIG. 4A;

GGCGCGGUGGUUGAGCUUGGCCAAAGGCGCCG-GACUCUAAAUC CGGUUCUCCA-CUGGGGAGCGGGGGUUCAAAUCCCUC-CCGCGCCG CCA (SEQ ID NO:34; M. maripaludis tRNA$^{UTu}$-amber), as depicted in FIG. 4A;

GGCGCGGUGGUUGAGCUUGGCCAAAGGCGCCG-GACUUUAAAUC CGGUUCUCCA-CUGGGGAGCGGGGGUUCAAAUCCCUC-CCGCGCCG CCA (SEQ ID NO:35; M. maripaludis tRNA$^{UTu}$-ochre).

In some embodiments, the non-naturally occurring tRNA$^{Sec}$ is a variant of SEQ ID NO:33 such as (SEQ ID NO: 36; M. maripaludis tRNA$^{UTu}$-opal - variant 1)
GGGCGCGGUGGUUGAGCUUGGCCAAAGGCGCCGGACUUCAAAU
CCGGUUCUCCACUGGGGAGCGGGGGUUCAAAUCCCUCCCGCGCC
CGCCA;

(SEQ ID NO: 37; M. maripaludis tRNA$^{UTu}$-opal - variant 2)
GGCGCGGUGGUUGAGCUUGGCCAAAGGCGCCGGACUUCAAAU
CCGGUUCUCCACUGGGGAGCGGGGGUUCAAAUCCCUCCCCGCGC
CGCCA;

(SEQ ID NO: 38; M. maripaludis tRNA$^{UTu}$-opal - variant 3)
GGCGCGGUGGUUGAGCUUGGCCAAAGGCGCCGGACUUCAAAUC
CGGUUCUCCACUGGGGAGCGUGGGUUCAAAUCCCACCCGCGCCG
CCA;

-continued (SEQ ID NO: 39; M. maripaludis tRNA$^{UTu}$-opal - variant 4)
GGGCGCGGGUGGUUGAGCUUGGCCAAAGGCGCCGGACUUCAAA
UCCGGUUCUCCACUGGGGAGCGGGGGUUCAAAUCCCUCCCCGCG
CCCGCCA;

(SEQ ID NO: 40; M. maripaludis tRNA$^{UTu}$-opal - variant 5)
GGGCGCGGGUGGUUGAGCUUGGCCAAAGGCGCCGGACUUCAAAU
CCGGUUCUCCACUGGGGAGCGUGGGUUCAAAUCCCACCCGCGCC
CGCCA;

(SEQ ID NO: 41; M. maripaludis tRNA$^{UTu}$-opal - variant 6)
GGCGCGGGUGGUUGAGCUUGGCCAAAGGCGCCGGACUUCAAAU
CCGGUUCUCCACUGGGGAGCGUGGGUUCAAAUCCCACCCCGCGC
CGCCA;
or (SEQ ID NO: 42; M. maripaludis tRNA$^{UTu}$-opal - variant 7)
GGGCGCGGGUGGUUGAGCUUGGCCAAAGGCGCCGGACUUCAAA
UCCGGUUCUCCACUGGGGAGCGUGGGUUCAAAUCCCACCCCGCG
CCCGCCA.

In some embodiments, the non-naturally occurring tRNA$^{Sec}$ is a variant of SEQ ID NO:34 such as (SEQ ID NO: 43; M. maripaludis tRNA$^{UTu}$-amber - variant 1)
GGGCGCGGUGGUUGAGCUUGGCCAAAGGCGCCGGACUCUAAAU
CCGGUUCUCCACUGGGGAGCGGGGGUUCAAAUCCCUCCCGCGCC
CGCCA;

(SEQ ID NO: 44; M. maripaludis tRNA$^{UTu}$-amber - variant 2)
GGCGCGGGUGGUUGAGCUUGGCCAAAGGCGCCGGACUCUAAAU
CCGGUUCUCCACUGGGGAGCGGGGGUUCAAAUCCCUCCCCGCGC
CGCCA;

(SEQ ID NO: 45; M. maripaludis tRNA$^{UTu}$-amber - variant 3)
GGCGCGGUGGUUGAGCUUGGCCAAAGGCGCCGGACUCUAAAUC
CGGUUCUCCACUGGGGAGCGUGGGUUCAAAUCCCACCCGCGCCG
CCA;

(SEQ ID NO: 46; M. maripaludis tRNA$^{UTu}$-amber - variant 4)
GGGCGCGGGUGGUUGAGCUUGGCCAAAGGCGCCGGACUCUAAA
UCCGGUUCUCCACUGGGGAGCGGGGGUUCAAAUCCCUCCCCGCG
CCCGCCA;

(SEQ ID NO: 47; M. maripaludis tRNA$^{UTu}$-amber - variant 5)
GGGCGCGGUGGUUGAGCUUGGCCAAAGGCGCCGGACUCUAAAU
CCGGUUCUCCACUGGGGAGCGUGGGUUCAAAUCCCACCCGCGCC
CGCCA;

(SEQ ID NO: 48; M. maripaludis tRNA$^{UTu}$-amber - variant 6)
GGCGCGGGUGGUUGAGCUUGGCCAAAGGCGCCGGACUCUAAAU
CCGGUUCUCCACUGGGGAGCGUGGGUUCAAAUCCCACCCCGCGC
CGCCA;
or (SEQ ID NO: 49; M. maripaludis tRNA$^{UTu}$-amber - variant 7)
GGGCGCGGGUGGUUGAGCUUGGCCAAAGGCGCCGGACUCUAAA
UCCGGUUCUCCACUGGGGAGCGUGGGUUCAAAUCCCACCCCGCG
CCCGCCA.

In some embodiments, the non-naturally occurring tRNA$^{Sec}$ is a variant of SEQ ID NO:35 such as (SEQ ID NO: 50; M. maripaludis tRNA$^{UTu}$-ochre - variant 1)
GGGCGCGGUGGUUGAGCUUGGCCAAAGGCGCCGGACUUUAAAU
CCGGUUCUCCACUGGGGAGCGGGGGUUCAAAUCCCUCCCGCGCC
CGCCA;

(SEQ ID NO: 51; M. maripaludis tRNA$^{UTu}$-ochre - variant 2)
GGCGCGGGUGGUUGAGCUUGGCCAAAGGCGCCGGACUUUAAAU
CCGGUUCUCCACUGGGGAGCGGGGGUUCAAAUCCCUCCCCGCGC
CGCCA;

(SEQ ID NO: 52; M. maripaludis tRNA$^{UTu}$-ochre - variant 3)
GGCGCGGUGGUUGAGCUUGGCCAAAGGCGCCGGACUUUAAAUC
CGGUUCUCCACUGGGGAGCGUGGGUUCAAAUCCCACCCGCGCCG
CCA;

(SEQ ID NO: 53; M. maripaludis tRNA$^{UTu}$-ochre - variant 4)
GGGCGCGGGUGGUUGAGCUUGGCCAAAGGCGCCGGACUUUAAA
UCCGGUUCUCCACUGGGGAGCGGGGGUUCAAAUCCCUCCCCGCG
CCCGCCA;

(SEQ ID NO: 54; M. maripaludis tRNA$^{UTu}$-ochre - variant 5)
GGGCGCGGUGGUUGAGCUUGGCCAAAGGCGCCGGACUUUAAAU
CCGGUUCUCCACUGGGGAGCGUGGGUUCAAAUCCCACCCGCGCC
CGCCA;

(SEQ ID NO: 55; M. maripaludis tRNA$^{UTu}$-ochre - variant 6)
GGCGCGGGUGGUUGAGCUUGGCCAAAGGCGCCGGACUUUAAAU
CCGGUUCUCCACUGGGGAGCGUGGGUUCAAAUCCCACCCCGCGC
CGCCA;
or (SEQ ID NO: 56; M. maripaludis tRNA$^{UTu}$-ochre - variant 7)
GGGCGCGGGUGGUUGAGCUUGGCCAAAGGCGCCGGACUUUAAA
UCCGGUUCUCCACUGGGGAGCGUGGGUUCAAAUCCCACCCCGCG
CCCGCCA.

A non-naturally occurring tRNA$^{Sec}$ that is a chimeric M. maripaludis tRNA can have a nucleic acid sequence at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more identical to SEQ ID NO:33, 34, 35, 36, 37, 38, 39, 40, 41, 42, 43, 44, 45, 46, 47, 48, 49, 50, 51, 52, 53, 54, 55, or 56. Preferably the non-naturally occurring tRNA$^{Sec}$ that is a chimeric M. maripaludis tRNA$^{Sec}$ is characterized by one or more of the following elements: (1) the non-naturally occurring tRNA$^{Sec}$ can be recognized by SerRS and by EF-Tu, or variants thereof; (2) when aminoacylated with serine the non-naturally occurring Ser-tRNA$^{Sec}$ can be converted to non-naturally occurring Sec-tRNA$^{Sec}$ by SelA or variant thereof; (3) when aminoacylated with serine the non-naturally occurring Ser-tRNA$^{Sec}$ can be phosphorylated by PSTK or variant thereof; (4) when aminoacylated with phosphorylated serine the non-naturally occurring Sep-tRNA$^{Sec}$ can serve as a substrate for SepSecS or variant thereof.

5. Secondary Structure

The tRNAs disclosed herein typically include an acceptor arm, a D-arm, an anticodon arm, a variable arm, and a TΨC-arm, as described in more detail below.

a. Acceptor Arm

The non-naturally occurring tRNA$^{Sec}$ disclosed herein includes an acceptor arm. The acceptor arm is the end of a tRNA molecule to which an amino acid becomes bound. It contains both the 5' and 3' ends of the tRNA. The 3'-terminal sequence of cytidine-cytidine-adenosine (CCA) overhangs the end, and the terminal A is the site of 'acceptance' of the amino acid.

The acceptor stem refers to the 5' and 3' sequences to the acceptor arm that form duplex RNA. The acceptor stem can be separate from the CCA overhang by one or more nucleotides, for example one or more guanine. In some embodiments, one or more nucleotides that separate the acceptor stem and the overhang are referred to as the discriminator base(s). For some tRNAs, the discriminator base preceding the CCA sequence at the 3' end is important for aminoacylation. The discriminator base can influence the stability of the base pair of the acceptor arm onto which it is stacked which can affect the energetic cost of opening the base pair and modulate the structure of the tRNA near the site of aminoacylation. For some aminoacyl-tRNA synthetases and other proteins that interact with tRNA, these factors could be important for specific recognition and/or formation of the transition state during catalysis (Lee et al., PNAS, 90(15): 7149-52 (1993)). In some embodiments, the acceptor stem and the CCA sequence are separated by a single guanine discriminator base.

The acceptor stem of the non-naturally occurring tRNA$^{Sec}$ disclosed herein typically include 4 to 12, preferably 5 to 11, more preferably 6 to 10, most preferably 7 to 9 base pairs of duplex RNA. In some embodiments, the acceptor stem is 7, 8, or 9 base pairs of duplex RNA.

The acceptor stem can be high in G-C content. For example, in some embodiments, the G-C content is 50%, 60%, 70%, 75%, 80%, 85%, 90%, 95%, or 100% of the nucleotides of the acceptor stem.

The 5' and 3' sequences of the tRNA that form the acceptor stem typically form a RNA duplex by Waston-Crick base pairing. The 5' and 3' sequences of the tRNA that form the acceptor stem are typically substantially complementary. Preferably, the 5' and 3' sequences of the tRNA that form the acceptor stem bind to or hybridize to each other under conditions of high stringency and specificity. In some embodiments, 5' sequence of the tRNA that forms the acceptor stem is 50%, 60%, 70%, 80%, 85%, 90%, 95%, or more complementary to the 3' sequence of the tRNA that forms the acceptor stem. In some embodiments the 5' and 3' sequences of the tRNA that form the acceptor stem are 100% complementary.

b. D-Arm

The non-naturally occurring tRNA$^{Sec}$ disclosed herein include a D-arm. The D-arm is typically composed of a D stem of duplex RNA and a D loop of non-duplex RNA. The D stem refers to the two segments of the tRNA primary sequence in the D-arm that form duplex RNA. The D stem of the non-naturally occurring tRNA$^{Sec}$ typically include 2 to 8, preferably 3 to 7, more preferably 4 to 6, base pairs of duplex RNA. In some embodiments, the D stem is 4, 5, or 6 base pairs of duplex RNA.

The D stem can be high in G-C content. For example, in some embodiments, the G-C content is 50%, 60%, 70%, 75%, 80%, 85%, 90%, 95%, or 100% of the nucleotides of the D stem.

The two segments of the tRNA that form the D stem typically fowl a RNA duplex by Waston-Crick base pairing. The two segments of the tRNA that form the D stem are typically substantially complementary. Preferably, the 5' and 3' sequences of the tRNA that form the acceptor stem bind to or hybridize to each other under conditions of high stringency and specificity. In some embodiments, 5' segment of the tRNA that forms the D stem is between 25% and 50% complementary to the 3' segment of the tRNA that forms the D stem. In some embodiments the 5' segment of the tRNA that forms the D stem is 50%, 60%, 70%, 80%, 85%, 90%, 95%, or more complementary to the 3' sequence of the tRNA that forms the D stem. In some embodiments the 5' and 3' sequences of the tRNA that fowl the D stem are 100% complementary.

The D loop refers to the part of the D-arm that does not form duplex RNA. The D loop's main function is that of recognition. The D loop can contain the base dihydrouracil. It is widely believed that it will act as a recognition site for aminoacyl-tRNA synthetase, which is an enzyme involved in the aminoacylation of the tRNA molecule. The D-loop can have between 3 and 15 nucleotides inclusive, preferably between 4 and 12 nucleotides inclusive. In some embodiments the D-loop has 4, 5, 6, 7, 8, 9, 10, 11, or 12 nucleotides.

c. Anticodon Arm

The non-naturally occurring tRNA$^{Sec}$ disclosed herein include an anticodon arm. The anticodon arm is typically composed of an anticodon stem of duplex RNA and an anticodon loop of non-duplex RNA. The anticodon stem refers to the two segments of the tRNA primary sequence in the anticodon arm that form duplex RNA. The anticodon stem of the non-naturally occurring tRNA$^{Sec}$ disclosed herein typically include 2 to 8, preferably 3 to 7, more preferably 4 to 6, base pairs of duplex RNA. In some embodiments, the anticodon stem is 4, 5, or 6 base pairs of duplex RNA.

The anticodon stem can be high in G-C content. For example, in some embodiments, the G-C content is 50%, 60%, 70%, 75%, 80%, 85%, 90%, 95%, or 100% of the nucleotides of the anticodon stem.

The two segments of the tRNA that form the anticodon stem typically form a RNA duplex by Waston-Crick base pairing. The two segments of the tRNA that form the anticodon stem are typically substantially complementary. Preferably, the 5' and 3' sequences of the tRNA that form the anticodon stem bind to or hybridize to each other under conditions of high stringency and specificity. In some embodiments the 5' segment of the tRNA that forms the anticodon stem is 50%, 60%, 70%, 80%, 85%, 90%, 95%, or more complementary to the 3' sequence of the tRNA that forms the anticodon stem. In some embodiments the 5' and 3' sequences of the tRNA that form the anticodon stem are 100% complementary.

The anticodon loop refers to the part of the anticodon -arm that does not form duplex RNA. The anticodon loop's main function is to present the anticodon sequence which can hybridize to the target codon in the mRNA sequence of interest. The anticodon sequence can be any three nucleotide sequence that binds by complementary base pairing to the target codon sequence in the mRNA of interest. In some embodiments, the anticodon pairs specifically with only one codon. Some anticodon sequences can pair with more than one codon (i.e., wobble base pairing). In some embodiments, the first nucleotide of the anticodon is inosine or pseudouridine, which can hydrogen bond to more than one base in the corresponding codon position.

In some embodiments, the anticodon hybridizes to a "stop" codon such as UAA, UAG, or UGA, preferably UAG (amber) or UGA (opal). Accordingly, in some embodiments the sequence of the anticodon is UUA, CUA, UCA, preferably CUA (amber) or UCA (opal) (in the 5' to 3' direction). The anticodon loop can have between 5 and 11 nucleotides inclusive, preferably about 7 nucleotides. In some embodiments the anticodon-loop has 5, 7, or 9 nucleotides. Typically, the three nucleotide anticodon sequence is flanked by an equal number of nucleotides both 5' and 3' of the anticodon sequence within the anticodon loop.

d. Variable Arm

The non-naturally occurring tRNA$^{Sec}$ disclosed herein includes a variable arm. The variable arm is typically composed of a variable stem of duplex RNA and a variable loop of non-duplex RNA. The variable stem refers to the two segments of the tRNA primary sequence in the variable arm that form duplex RNA. The variable stem of the non-naturally occurring tRNA$^{Sec}$ typically includes 2 to 8, preferably 3 to 7, more preferably 4 to 6, base pairs of duplex RNA. In some embodiments, the variable stem is 4, 5, or 6 base pairs of duplex RNA. In some embodiments the variable stem has 9, 10, 11, or more base pairs of duplex RNA.

The variable stem can be high in G-C content. For example, in some embodiments, the G-C content is 50%, 60%, 70%, 75%, 80%, 85%, 90%, 95%, or 100% of the nucleotides of the variable stem.

The two segments of the tRNA that form the variable stem typically form a RNA duplex by Waston-Crick base pairing. The two segments of the tRNA that form the anticodon stem are typically substantially complementary. Preferably, the 5' and 3' sequences of the tRNA that form the variable stem bind to or hybridize to each other under conditions of high stringency and specificity. In some embodiments the 5' segment of the tRNA that forms the variable stem is 50%, 60%, 70%, 80%, 85%, 90%, 95%, or more complementary to the 3' sequence of the tRNA that forms the variable stem. In some embodiments the 5' and 3' sequences of the tRNA that form the variable stem are 100% complementary.

The variable loop refers to the part of the variable-arm that does not form duplex RNA. The variable loop can have between 3 and 7 nucleotides inclusive, preferably between 4 and 6 nucleotides inclusive. In some embodiments the variable loop has 3, 4, 5, 6, or 7 nucleotides.

e. TΨC-Arm

The non-naturally occurring tRNA$^{Sec}$ disclosed herein includes a TΨC-arm (also referred to herein as a T-arm). The T-arm is the region on the tRNA molecule that acts as a recognition site for the ribosome, and allows a tRNA-ribosome complex to form during the process of protein biosynthesis. The T-arm is typically composed of a T stem of duplex RNA and a T loop of non-duplex RNA. The T stem refers to the two segments of the tRNA primary sequence in the T-arm that form duplex RNA. The T stem of the non-naturally occurring tRNA$^{Sec}$ typically includes 2 to 8, preferably 3 to 7, more preferably 4 to 6, base pairs of duplex RNA. In some embodiments, the T stem is 3, 4, or 5 base pairs of duplex RNA.

The T stem can be high in G-C content. For example, in some embodiments, the G-C content is 50%, 60%, 70%, 75%, 80%, 85%, 90%, 95%, or 100% of the nucleotides of the T stem.

The two segments of the tRNA that foil the T stem typically form a

RNA duplex by Waston-Crick base pairing. The two segments of the tRNA that form the T stem are typically substantially complementary. Preferably, the 5' and 3' sequences of the tRNA that form the acceptor stem bind to or hybridize to each other under conditions of high stringency and specificity. In some embodiments, 5' segment of the tRNA that fauns the T stem is equal to or greater than 50% complementary to the 3' segment of the tRNA that forms the T stem. In some embodiments the 5' segment of the tRNA that forms the T stem is 50%, 60%, 70%, 80%, 85%, 90%, 95%, or more complementary to the 3' sequence of the tRNA that forms the T stem. In some embodiments the 5' and 3' sequences of the tRNA that form the T stem are 100% complementary.

The T loop refers to the part of the T-arm that does not form duplex RNA. In some embodiments the T-loop includes thymidine, pseudouridine, residues, or combinations thereof. The T-loop can have between 3 and 15 nucleotides inclusive, preferably between 4 and 12 nucleotides inclusive. In some embodiments the D-loop has 4, 5, 6, 7, 8, 9, 10, 11, or 12 nucleotides.

f. Linker Nucleotides

The five arms of the tRNA can be linked directly, or can be separated by one or more linker or spacer nucleotides to ensure the tRNA assumes the proper secondary structure. For example, the acceptor arm and the D-arm can separated by 0, 1, 2, 3, or more nucleotides; the D-arm and the anticodon arm can be separated by 0, 1, 2, 3, or more nucleotides; the anticodon arm and the variable arm can be separated by 0, 1, 2, 3, or more nucleotides; the variable arm and the T-arm can be separated by 0, 1, 2, 3, or more nucleotides; and the T-arm and the acceptor arm can be separated by 0, 1, 2, 3, or more nucleotides.

B. mRNA and Polypeptides of Interest

As discussed in more detail below, the non-naturally occurring tRNA$^{Sec}$ disclosed herein can be used in combination with an mRNA to manufacture selenocysteine containing polypeptides and proteins. The mRNA does not require, and preferably does not include, a SECIS element. The mRNA, which encodes a polypeptide of interest, includes one or more codons that is recognized by the anticodon of the Sec-tRNA$^{Sec}$, referred to herein as an "tRNA$^{Sec}$ recognition codon," such that tRNA catalyzes the attachment of a selenocysteine amino acid to the growing polypeptide chain during translation.

For example, if the tRNA$^{Sec}$ recognition codon is a stop codon, such as UGA, the mRNA will contain at least one UGA codon where a selenocysteine will be added to the growing polypeptide chain during translation. The tRNA$^{Sec}$ recognition codon can be added to or inserted into any mRNA to add a codon encoding selenocysteine at any desired location in the amino acid sequence. The tRNA$^{Sec}$ recognition codon can be substituted for any existing codon in the mRNA sequence so that any one or more amino acids from a reference polypeptide sequence is substituted with selenocysteine during translation. For example, as discussed in more detail below, in some embodiments, one or more codons encoding cysteine in a reference sequence are substituted with a tRNA$^{Sec}$ recognition sequence so that the one or more cysteines are replaced with selenocysteine during translation.

Various types of mutagenesis can be used to modify the sequence of a nucleic acid encoding the mRNA of interest to generate the tRNA$^{Sec}$ recognition codon. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, and mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis and double-strand break repair.

In some embodiments, the coding sequence, excluding the tRNA$^{Sec}$ recognition site as discussed above, is further altered for optimal expression (also referred to herein as "codon optimized") in an expression system of interest.

Methods for modifying coding sequences to achieve optimal expression are known in the art.

C. Isolated Nucleic Acid Molecules

Non-naturally occurring tRNA$^{Sec}$ and nucleic acids encoding non-naturally occurring tRNA$^{Sec}$ are disclosed. Also disclosed are mRNAs, cDNAs and other nucleic acids encoding proteins of interest that are engineered such that a tRNA$^{Sec}$, such as the non-naturally occurring tRNA$^{Sec}$ disclosed herein, "reads" at least one codon of the mRNA during translation of the protein encoded by the mRNA. As used herein, "isolated nucleic acid" refers to a nucleic acid that is separated from other nucleic acid molecules that are present in a genome, including nucleic acids that normally flank one or both sides of the nucleic acid in the genome. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule or an RNA molecule, provided one of the nucleic acid sequences normally found immediately flanking that DNA molecule in a naturally-occurring genome is removed or absent. Thus, an isolated nucleic acid includes, without limitation, a DNA molecule or RNA molecule that exists as a separate molecule independent of other sequences (e.g., a chemically synthesized nucleic acid, or a cDNA, or RNA, or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule or RNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding the tRNA$^{Sec}$ and mRNA disclosed herein may be optimized for expression in the expression host of choice. In the case of nucleic acids encoding expressed polypeptides, codons may be substituted with alternative codons encoding the same amino acid to account for differences in codon usage between the organism from which the nucleic acid sequence is derived and the expression host. In this manner, the nucleic acids may be synthesized using expression host-preferred codons.

Nucleic acids can be in sense or antisense orientation, or can be complementary to a reference sequence, for example, a sequence encoding the disclosed tRNA$^{Sec}$ and mRNA. Nucleic acids can be DNA, RNA, nucleic acid analogs, or combinations thereof. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chem. 4:5-23. In addition, the deoxyphosphate backbone can be replaced with, for example, a phosphorothioate or phosphorodithioate backbone, a phosphoroamidite, or an alkyl phosphotriester backbone.

D. Methods for Producing Isolated Nucleic Acid Molecules

Isolated non-naturally occurring tRNA$^{Sec}$, nucleic acids encoding non-naturally occurring tRNA$^{Sec}$, and nucleic acids encoding polypeptides manufactured using the non-naturally occurring tRNA$^{Sec}$, are disclosed. Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a non-naturally occurring tRNA$^{Sec}$. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995.

When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992. Examples of nucleic acid amino acid positions relative to a reference sequence that can be modified include those described herein.

E. Vectors and Host Cells

Vectors encoding non-naturally occurring tRNA$^{Sec}$ and polypeptides manufactured using the non-naturally occurring tRNA$^{Sec}$ are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. Operably linked means the disclosed sequences are incorporated into a genetic construct so that expression control sequences effectively control expression of a sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II).

A "promoter" as used herein is a DNA regulatory region capable of initiating transcription of a gene of interest. Some promoters are "constitutive," and direct transcription in the absence of regulatory influences. Some promoters are "tissue specific," and initiate transcription exclusively or selectively in one or a few tissue types. Some promoters are "inducible," and achieve gene transcription under the influence of an inducer. Induction can occur, e.g., as the result of a physiologic response, a response to outside signals, or as the result of artificial manipulation. Some promoters respond to the presence of tetracycline; "rtTA" is a reverse tetracycline controlled transactivator. Such promoters are well known to those of skill in the art.

To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Likewise, although tRNA$^{Sec}$ sequences do not encode a protein, control sequence can be operably linked to a sequence encoding a tRNA$^{Sec}$, to control expression of the tRNA$^{Sec}$ in a host cell. Methods of recombinant expression of tRNA from vectors is known in the art, see for example, Ponchon and Dardel, *Nature Methods,* 4(7):571-6 (2007); Masson and Miller, J. H., Gene, 47:179-183 (1986); Meinnel, et al., *Nucleic Acids Res.,* 16:8095-6 (1988); Tisné, et al., *RNA,* 6:1403-1412 (2000).

F. Host Cells

Host cell including the nucleic acids disclosed herein are also provided. Prokaryotes useful as host cells include, but are not limited to, gram negative or gram positive organisms such as *E. coli* or *Bacilli*. In a prokaryotic host cell, a polypeptide may include an N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, T7 expression vectors from Invitrogen, pET vectors from Novagen and pALTER® vectors and PinPoint® vectors from Promega Corporation.

In some embodiments, the host cells are *E. coli*. The *E. coli* strain can be a selA, selB, selC, deletion strain, or combiantions thereof. For example, the *E. coli* can be a selA, selB, and selC deletion strain, or a selB and selC deletion strain. Examples of suitable *E. coli* strains include, but are not limited to, MH5 and MH6.

Yeasts useful as host cells include, but are not limited to, those from the genus *Saccharomyces, Pichia, K. Actinomycetes* and *Kluyveromyces*. Yeast vectors will often contain an origin of replication sequence, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem, 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991), in Li, et al., *Lett Appl Microbial.* 40(5):347-52 (2005), Jansen, et al., *Gene* 344:43-51 (2005) and Daly and Hearn, *J. Mol. Recognit.* 18(2):119-38 (2005). Other suitable promoters and vectors for yeast and yeast transformation protocols are well known in the art.

In some embodiments, the host cells are eukaryotic cells. For example, mammalian and insect host cell culture systems well known in the art can also be employed to express non-naturally occurring tRNA$^{Sec}$ and mRNA for producing proteins or polypeptides containing selenocysteine. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

III. Methods for Manufacturing Proteins Containing Selenocysteine

A. Expression of Selenocysteine Containing Polypeptides

Figure 1A:
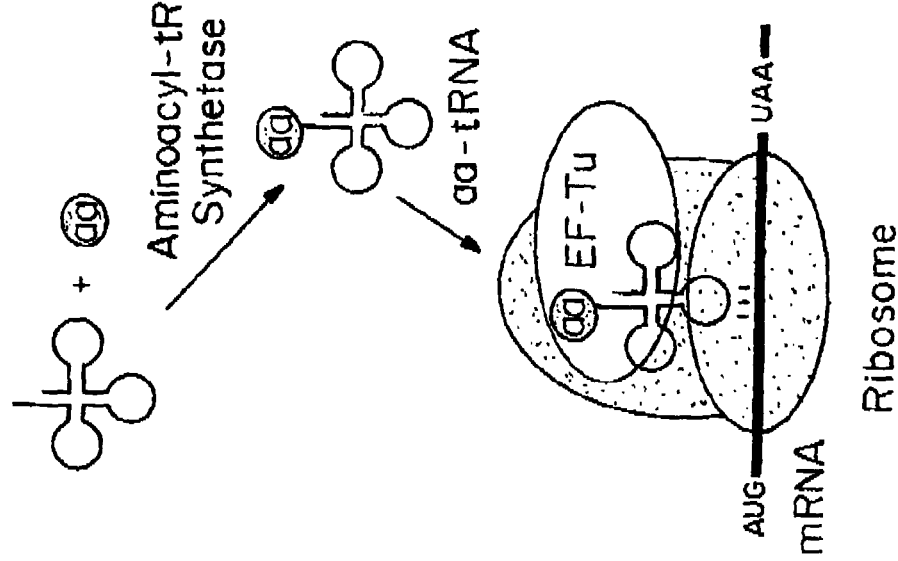

Generally, the canonical amino acids are charged onto their respective tRNA by their cognate aminoacyl-tRNA synthetase. The aminoacyl-tRNA is then delivered by EF-Tu to the ribosome (FIG. 1A). In contrast, the endogenous Sec pathway requires several biosynthetic steps. First, tRNA$^{Sec}$ is misacylated to Ser-tRNA$^{Sec}$ by SerRS. While in bacteria Ser-tRNA$^{Sec}$ is directly converted by SelA to Sec-tRNA$^{Sec}$, archaea and eukaryotes employ an additional phosphorylation step by PSTK to form Sep-tRNA$^{Sec}$, which is then converted by SepSecS to the final product Sec-tRNA$^{Sec}$ FIG. 1B. Sec-tRNA$^{Sec}$ is bound by elongation factor SelB and delivered to the ribosome. However, reassignment of the opal codon UGA to a Sec codon is only achieved if SelB also binds to the mRNA SECIS hairpin structure.

The compositions disclosed herein can be used to prepare polypeptides including one or more selenocysteine residues from mRNA that does not contain an SECIS element. The tRNA$^{Sec}$ disclosed herein is recognized by SerRS and misacylated to form the intermediate Ser-tRNA$^{Sec}$. Next the Ser-tRNA$^{Sec}$ is converted to Sec-tRNA$^{Sec}$ by SelA in prokaryotic system or hybrid systems, or PSTK and SepSecS in archaeal, eukaryotic, or hybrid systems. Finally, the Sec-tRNA$^{Sec}$ is delivered to the ribosome by EF-Tu, where the anticodon of the Sec-tRNA$^{Sec}$ recognizes the codon engineered to encode a Sec amino acid, and transfers the Sec onto the growing polypeptide chain. Accordingly, the non-naturally occurring tRNA$^{Sec}$ disclosed herein are typically recognized by SerRS, or a variant thereof, and when aminoacylated with serine the Ser-tRNA can (1) be a substrate for SelA or a variant thereof; or (2) be a substrate for PSTK and when aminoacylated with phosphorylated serine the Sep-tRNA can serve as a substrate for SepSecS or a variant thereof, and (3) when aminoacylated, the non-naturally occurring Sec-tRNA$^{Sec}$ is recognized by EF-Tu.

As discussed in more detail below, recombinant proteins including selenocysteine can be prepared using in vitro transcription/translation or in vivo expression systems. The system can be of prokaryotic, eukaryotic, or archaeal origin or combinations thereof. For example, the system can be hybrid system including selenocysteine biogenesis and translation factors from prokaryotic, eukaryotic, archaeal origin, or combinations thereof. In some embodiments, the system is an in vivo prokaryotic expression including an E. coli strain in which the endogenous genes encoding selB, selC, or selA, selB, selC are deleted or mutated to reduce or eliminate expression of endogenous SelA, SelB, SelC or combinations thereof. The selB, selC, or selA, selB, selC mutant strains can be engineered to express a non-naturally occurring tRNA$^{Sec}$, as well as a PSTK and a SepSecS. In some embodiments recombinant SelA is expressed. The PSTK or SepSecS can of eukaryotic or archaeal origin, or a variant thereof. For example, in one embodiment, the PSTK is a M. maripaludis PSTK and the SepSecS is a M. jannaschii SepSecS. In some embodiments, SelA, PSTK and SepSecS are all expressed in the expression system.

In some embodiments selenocysteine biogenesis and translation factors are mutated to improve their specificity or activity for the non-naturally occurring tRNA$^{Sec}$. In the recombinant tRNA$^{Sec}$ biosynthetic pathway disclosed herein non-naturally occurring tRNA$^{Sec}$ is first misacylated to Ser-tRNA$^{Sec}$ by SerRS, and subsequently converted to Sec-tRNA$^{Sec}$ by SelA, or PSTK and SepSecS, or combinations thereof. Accordingly, if the SelA, or PSTK and SepSecS, enzymes are not 100% efficient at converting Ser-tRNA$^{Sec}$ to Sec-tRNA$^{Sec}$, the system may incorporate Sec or Ser at the desired position. Additionally, in some embodiments, recognition of the non-naturally occurring Sec-tRNA$^{Sec}$ by EF-Tu, is less efficient than EF-Tu recognition of other naturally occurring aminoacyl-tRNAs. Mutating the EF-Tu, SerRS, SelA, PSTK, SepSecS, or combinations thereof can improve the efficiency or recognition of the enzyme for the non-naturally occurring tRNA$^{Sec}$, the non-naturally occurring Sec-tRNA$^{Sec}$, or various intermediates thereof. Accordingly, in some embodiment, the EF-Tu, SerRS, SelA, PSTK, SepSecS, or combinations thereof are variants of a naturally occurring protein.

It is understood that if the tRNA$^{Sec}$ recognition codon of the mRNA of interest is one of the three mRNA stop codons (UAG, UAA, or UGA) translation of some of the mRNA of interest will terminate at each of the tRNA$^{Sec}$ recognition codons, resulting in a heterogeneous mixture of full-length and truncated proteins. Therefore, in some embodiments, the selenocysteine containing protein is expressed in a system that has been modified or mutated to reduce or eliminate expression of one or more translation release factors. A release factor is a protein that allows for the termination of translation by recognizing the termination codon or stop codon in an mRNA sequence. Prokaryotic release factors include RF1, RF2 and RF3; and eukaryotic release factors include eRF1 and eRF3.

Deletion of one or more release factors may result in "read-through" of the intended stop codon. Accordingly, some of recombinant proteins expressed in a system with one or more release factors may include one or more additional amino acids at the C-terminal end of the protein.

The protein of interest can be purified from the truncated proteins and other contaminants using standard methods of protein purification as discussed in more detail below.

1) In Vitro Transcription/Translation

In one embodiment, the genes encoding a non-naturally occurring tRNA$^{Sec}$, mRNA encoding the protein of interest, mRNA encoding EF-Tu, SerRS, SelA, PSTK, SepSecS, or combinations thereof are synthesized in vitro prior to or along with transcription and translation of the protein of interest. The synthesis of protein from a DNA sequence in vitro takes two steps. The first is transcription of an RNA copy and the second is the translation of a protein.

In vitro protein synthesis does not depend on having a polyadenylated RNA, but if having a poly(A) tail is essential for some other purpose a vector may be used that has a stretch of about 100 A residues incorporated into the polylinker region. That way, the poly(A) tail is "built in" by the synthetic method.

Eukaryotic ribosomes read RNAs more efficiently if they have a 5' methyl guanosine cap. RNA caps can be incorporated by initiation of transcription using a capped base analogue, or adding a cap in a separate in vitro reaction post-transcriptionally.

The use of in vitro translation systems can have advantages over in vivo gene expression when the over-expressed product is toxic to the host cell, when the product is insoluble or forms inclusion bodies, or when the protein undergoes rapid proteolytic degradation by intracellular proteases. Various approaches to in vitro protein synthesis are known in the art and include translation of purified RNA, as well as "linked" and "coupled" transcription:translation. In vitro translation systems can be eukaryotic or prokaryotic cell-free systems.

Combined transcription/translation systems are available, in which both phage RNA polymerases (such as T7 or SP6)

and eukaryotic ribosomes are present. One example of a kit is the TNT® system from Promega Corporation.

Other suitable in vitro transcription/translation systems include, but are not limited to, the rabbit reticulocyte system, the E. coli S-30 transcription-translation system, and the wheat germ based translational system.

2) In Vivo Methods Transcription/Translation a. Extrachromosomal Expression

Host cells can be genetically engineered (e.g., transformed, transduced or transfected) with the vectors encoding non-naturally occurring tRNA$^{Sec}$ and a nucleic acid encoding the protein of interest, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., Proc. Natl. Acad. Sci. USA 82, 5824 (1985), infection by viral vectors, high velocity ballistic penetration by small particles with the nucleic acid either within the matrix of small beads or particles, or on the surface (Klein et al., Nature 327, 70-73 (1987)). Methods of expressing recombinant proteins in various recombinant expression systems including bacteria, yeast, insect, and mammalian cells are known in the art, see for example Current Protocols in Protein Science (Print ISSN: 1934-3655 Online ISSN: 1934-3663, Last updated January 2012).

Kits are commercially available for the purification of plasmids from bacteria, (see, e.g., GFX™ Micro Plasmid Prep Kit from GE Healthcare; Strataprep® Plasmid Miniprep Kit and StrataPrep® EF Plasmid Midiprep Kit from Stratagene; GenElute™ HP Plasmid Midiprep and Maxiprep Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Useful prokaryotic and eukaryotic systems for expressing and producing polypeptides are well known in the art include, for example, Escherichia coli strains such as BL-21, and cultured mammalian cells such as CHO cells.

In eukaryotic host cells, a number of viral-based expression systems can be utilized to express non-naturally occurring tRNA$^{Sec}$ and mRNA for producing proteins or polypeptides containing selenocysteine. Viral based expression systems are well known in the art and include, but are not limited to, baculoviral, SV40, retroviral, or vaccinia based viral vectors.

Mammalian cell lines that stably express tRNA and proteins can be produced using expression vectors with appropriate control elements and a selectable marker. For example, the eukaryotic expression vectors pCR3.1 (Invitrogen Life Technologies) and p91023(B) (see Wong et al. (1985) Science 228:810-815) are Suitable for expression of recombinant proteins in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin or by metabolic selection using the Glutamine Synthetase-NS0 system). The transfected cells can be cultured such that the polypeptide of interest is expressed, and the polypeptide can be recovered from, for example, the cell culture supernatant or from lysed cells.

b. Expression by Genomic Integration

Methods of engineering a microorganism or cell line to incorporate a nucleic acid sequence into its genome are known in the art. For example, cloning vectors expressing a transposase and containing a nucleic acid sequence of interest between inverted repeats transposable by the transposase can be used to clone the stably insert the gene of interest into a bacterial genome (Barry, Gene, 71:75-84 (1980)). Stably insertion can be obtained using elements derived from transposons including, but not limited to Tn7 (Drahos, et al., Bio/Tech. 4:439-444 (1986)), Tn9 (Joseph-Liauzun, et al., Gene, 85:83-89 (1989)), Tn10 (Way, et al., Gene, 32:369-379 (1984)), and Tn5 (Berg, In Mobile DNA. (Berg, et al., Ed.), pp. 185-210 and 879-926. Washington, D.C. (1989)). Additional methods for inserting heterologous nucleic acid sequences in E. coli and other gram-negative bacteria include use of specialized lambda phage cloning vectors that can exist stably in the lysogenic state (Silhavy, et al., Experiments with gene fusions, Cold Spring Harbor Laboratory, Cold Spring Harbor, N.Y. (1984)), homologous recombination (Raibaud, et al., Gene, 29:231-241 (1984)), and transposition (Grinter, et al., Gene, 21:133-143 (1983), and Herrero, et al., J. Bacteriology, 172(11):6557-6567 (1990)).

Methods of engineering other microorganisms or cell lines to incorporate a nucleic acid sequence into its genome are also known in the art. For example, integrative plasmids can be used to incorporate nucleic acids sequences into yeast chromosomes. See for example, Taxis and Knop, Bio/Tech., 40(1):73-78 (2006), and Hoslot and Gaillardin, Molecular Biology and Genetic Engineering of Yeasts. CRC Press, Inc. Boca Raton, Fla. (1992). Methods of incorporating nucleic acid sequence into the genomes of mammalian lines are also well known in the art using, for example, engineered retroviruses such lentiviruses.

B. Purification of Selenocysteine Containing Polypeptides

Selenocysteine containing polypeptides can be isolated using, for example, chromatographic methods such as affinity chromatography, ion exhange chromatography, hydrophobic interaction chromatography, DEAE ion exchange, gel filtration, and hydroxylapatite chromatography. In some embodiments, selenocysteine containing polypeptides can be engineered to contain an additional domain containing amino acid sequence that allows the polypeptides to be captured onto an affinity matrix. For example, an Fe-containing polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify selenocysteine containing polypeptides. Selenocysteine containing polypeptides can additionally be engineered to contain a secretory signal (if there is not a secretory signal already present) that causes the protein to be secreted by the cells in which it is produced. The secreted proteins can then conveniently be isolated from the cell media.

In some embodiments, selenocysteine containing polypeptides are isolated using activated thiol SEPHAROSE®, for example, Activated Thiol SEPHAROSE® 4B. As discussed above, in the recombinant tRNA$^{Sec}$ biosynthetic pathway disclosed herein non-naturally occurring tRNA$^{Sec}$ is first misacylated to a non-naturally occurring Ser-tRNA$^{Sec}$ by SerRS, and subsequently converted to Sec-tRNA$^{Sec}$ by SelA, or PS TK and SepSecS, or combinations thereof. Accordingly, if the SelA, or PSTK and SepSecS, enzymes are not 100% efficient at converting Ser-tRNA$^{Sec}$ to Sec-tRNA$^{Sec}$, the system may incorporate Sec or Ser at the desired position, leading to a heterogeneous mixture of proteins. Activated thiol SEPHAROSE® can be incorporated into the protein purification process to purify Sec containing proteins from the Ser containing contaminants.

IV. Methods of Using Selenocysteine Containing Polypeptide

The compositions and methods disclosed herein can be used to manufacture polypeptides and proteins with one or more selenocysteine residues. In some embodiments, the mRNA encodes a polypeptide that is a naturally occurring selenocysteine containing polypeptide. In some embodiments, the mRNA encodes a polypeptide that is not a naturally occurring selenocysteine containing polypeptide. A nucleic acid sequence can include a codon that is recognized by the anticodon of a tRNA$^{Sec}$ disclosed herein, for example a nucleic acid encoding a naturally occurring selenocysteine containing protein, or can be modified to include a codon recognized by the anticodon of a tRNA$^{Sec}$. The nucleic acid sequence encoding the polypeptide can also be codon optimized for expression in the desired recombinant expression system. The nucleic acid can be expressed from a vector or incorporated into the genome of the desired expression system.

A. Recombinant Selenocysteine Containing Peptides—Naturally Occurring

The disclosed compositions and methods can be used for recombinant expression of naturally occurring selenocysteine containing peptides, or variants thereof. Selenoproteins exist in all major forms of life, including, eukaryotes, bacteria and archaea. Accordingly, in some embodiments, the mRNA of interest is an mRNA encoding a selenocysteine containing peptide from an eukaryote, a bacteria, or an archaea. The human genome encodes at least 25 naturally occurring selenocysteine containing peptides (Kryukov, et al, *Science*, 300:1439-1443 (2003)). Therefore, in some embodiments the mRNA encodes a iodothyronine deiodinase such as DIO1, DIO2, DIO3; a glutathione peroxidase such as GPX1, GPX2, GPX3, GPX4, or GPX6; a selenoprotein such as SelH, SelI, SelK, SelM, SelN, SelO, SelP, SelR, SelS, SelT, SelV, SelW, or Sel15; selenophosphate synthetase 2 (SPS2); or a thioredoxin reductase such as TXNRD1, TXNRD2, or TXNRD3.

Conditions to be Treated

In some embodiments, recombinant selenocysteine containing polypeptides prepared according to the claimed methods are administered to a subject in an effective amount to treat a disease, or one or more symptoms thereof. As discussed in Riaz and Mehmood, *JPMI*, 26(02):120-133 (2012) and Tapiero, et al., *Biomedicine & Pharmacotherapy* 57:134-144 (2003), many health effects of low selenium are thought to be due to lack of one or more specific selenocysteine containing proteins. For example, reduction or loss of one or more selenocysteine containing protein in a subject can be associated with increased oxidative stress in the subject. Accordingly, a recombinant selenocysteine containing protein can be administered to subject in an effective amount to increase antioxidant activity, or reduce oxidative stress in the subject. In some embodiments, the recombinant selenocysteine containing protein can be used to treat or prevent an age-related disorder, asthma, diabetes, an infectious disease, a cardiovascular disorder, a cancer, male infertility, pre-eclampsia, a gastrointestinal disorder, thyroid metabolism, or another diseases or condition associated with reduced levels or activity of selenocysteine containing proteins.

B. Recombinant Selenocysteine Containing Peptides—Non-Naturally Occurring

The disclosed compositions and methods can also be used for producing by recombinant expression a selenocysteine containing polypeptide variant of any polypeptide that does not naturally contain selenocysteine.

1. Insertion of Selenocysteine

One or more selenocysteines can be added to the beginning, end, and/or inserted into a polypeptide that does not typically have a selenocysteine. Adding one or more selenocysteines can change the biochemical and functional properties of the protein, for example, change the redox potential of the protein, increase the half-life of the protein, increase the stability or resistance to degradation, increase the activity of the protein (such as enzymatic activity), alter the pharmacokinetics of the protein, alter the binding affinity (such as the binding affinity of an antibody to antigen or ligand to receptor), change the folding properties of the protein, induce new epitopes onto the protein, or tag the protein for purification.

In some embodiments, the one or more selenocysteines changes the biochemical properties of the protein so it can be easily purified after recombinant expression. In some embodiments, selenocysteine can be added to a protein and used as a purification tag. For example, activated thiol SEPHAROSE®, or an equivalent thereof, can be incorporated into the protein purification process to purify Sec containing proteins from contaminants.

2. Substitution with Selenocysteine

In some embodiments, selenocysteine is substitute for one or more naturally occurring cysteines.

Reversible oxidation of thiols to disulfides or sulfenic acid residues controls biological functions in at least three general ways, by chemically altering active site cysteines, by altering macromolecular interactions, and by regulating activity through modification of allosteric Cys (reviewed in Jones, *Am. J. Physiol.*, 295(4):C849-868 (2008)). Half of all enzyme activities are sensitive to either oxidation, reaction with electrophiles, or interaction with metal ions. Enzymes with active-site Cys include caspases, kinases, phosphatases, and proteases. Cys is also a component of active sites of iron-sulfur clusters of electron transfer proteins and a element of zinc fingers in transcription factors and zinc-binding domains of metallothioneins. Cys residues are also conserved in structural proteins such as actin and docking proteins such as 14-3-3. Oxidation of Cys residues in αIIbβ3 integrin controls platelet activation. Cys-rich regions are present in plasma membrane receptors and ion channels, including the NMDA receptors, EGF receptor, and others. Thus reversible oxidation of active site thiols can provide a common and central "on-off" mechanism for control of cell functions.

β-Actin contains a conserved Cys, which results in reversible binding of proteins, S-GS-ylation, and crosslinking of actin filaments upon oxidation. Oxidation functions in glucocorticoid receptor translocation into nuclei, and oxidation controls export of yeast AP-1 (Yap-1) from nuclei. Disulfide crosslinks control fluidity of mucus. Such changes in protein structure and interaction due to reversible oxidation can provide a central mechanism for specificity in redox signaling. In addition to containing active site and/or structural thiols, many proteins contain Cys which regulate activity by an allosteric mechanism. This type of regulation can provide a "rheostat" rather than an "on-off" switch, thereby providing a means to throttle processes by GS-ylation or S-nitrosylation.

Many naturally occurring selenoproteins with known functions are oxidoreductases which contain catalytic redox-active Sec (Jacob C, et al., *Angew. Chem. Int. Ed. Engl.,* 42:4742-4758 (2003)). Variants of the naturally occurring selenoprotein in which the Sec residues are replaced with Cys residues are typically 100-1,000 times less active (Johansson L, et al, *Biochim. Biophys. Acta.,* 1726:1-13 (2005)). Furthermore, analogs of naturally occurring proteins where one or more Cys residues are replaced with Sec can generate analogs that retain the folding of the native peptides, are more potent, and have the same or greater biological activity (Raffa, *Life Sci.,* 87(15-16):451-6 (2010)).

Therefore, in some embodiments, the disclosed compositions and methods are used to manufacture recombinant variants or analogs where one or more naturally occurring Cys residues, for example Cys residues in the active site of an enzyme, are replaced with Sec residues. The methods and compositions can be used to generate analogs that retain a folding of the protein similar or the same as the native peptides, but are more potent while having the same or greater biological activity. Substituting one or more naturally occurring Cys residues with a Sec can increase the activity of the protein by 2, 5, 10, 100, 250, 500, 1,000 or more-fold over the activity of the protein that does not contain the Sec residue(s). Accordingly, the analogs can be used in therapeutic or research applications at a lower dosage, less frequently, with reduced toxicity, or combinations thereof relative to the naturally occurring protein.

In some embodiments, the disclosed compositions and methods can be used to prepare recombinant polypeptides where one or more cysteines that contributes to the formation of a disulfide bond in the protein is replaced with selenocysteine. Therefore, recombinant proteins having one or more Sec-Sec (diselenide) or Cys-Sec (selenocysteine-cysteine) bonds are disclosed.

A disulfide bond is a covalent bond, usually derived by the coupling of two thiol groups. Disulfide bonds in proteins are formed between the thiol groups of cysteine residues. A disulfide bond can stabilize the folded form of a protein in several ways. For example a disulfide bond can hold two portions of the protein together, favoring a folded topology and contributing to the formation and stability of secondary and tertiary structures. A disulfide bond can also form the center of a hydrophobic core in a folded protein, i.e., local hydrophobic residues may condense around the disulfide bond and onto each other through hydrophobic interactions. In some cases the hydrophobic core is an enzyme's active site, and the disulfide bond is necessary for enzymatic efficiency or activity.

A diselenide bond, which is formed between two selenocysteine residues, or a selenocysteine-cysteine bond between a selenocysteine and cysteine can impart similar structural and functional characteristics to the protein as a disulfide bond. Diselenide and selenocysteine-cysteine bonds are infrequent in nature, but have been reported to be in the active site of some enzymes, for example the selenocysteine protein SelL (Shchedrina, et al., *PNAS,* 104(35): 13919-13924 (2007)). Diselenide bonds have very low redox potential, but in some cases can be reduced by thioredoxin.

Therefore, in some embodiments, the disclosed compositions and methods are used to manufacture recombinant variants where one or more naturally occurring disulfide bonds are replaced with a diselenide or a selenocysteine-cysteine bond.

Replacing disulfide bonds with diselenide or selenocysteine-cysteine bonds can be used to reduce the redox potential of the bond, increase the half-life of the protein, increase the activity of the protein, alter the pharmacokinetics of the protein, for example, increase or decrease the association or dissociation constant, alter the folding and unfolding properties of the protein, or combinations thereof. For example, substituting one or more naturally occurring Cys residues with a Sec can increase the activity of the protein by 2, 5, 10, 100, 250, 500, 1,000 or more-fold over the activity of the protein that does not contain the Sec residue(s). Accordingly, the analogs can be used in therapeutic or research applications at a lower dosage, less frequently, with reduced toxicity, or combinations thereof relative to the naturally occurring protein.

Exemplary proteins where a naturally occurring Cys can be replaced with Sec according to the compositions and methods disclosed herein include, but are not limited to, caspases, kinases, phosphatases, proteases, transcription factors, metallothioneins, structural proteins such as actin and docking proteins such as 14-3-3, integrins such as αIIbβ3, plasma membrane receptors, ion channels, including the NMDA receptors, EGF receptor, and others.

The disclosed compositions and methods can be particularly useful for preparing recombinant antibodies, antigen binding fragments thereof, fusion proteins including a least one antibody domain (i.e., Ig fusion proteins) with altered properties, and receptor such as T cell receptors or receptor fragments including the binding domains. Antibodies contain inter-chain disulfide bonds which link the heavy and light chains, disulfide bonds that link two heavy chains, and disulfide bonds that link the two hinge regions. Antibodies also have disulfide bonds within the chains themselves (referred to as intra-chain disulfide bonds). The disclosed compositions and methods can be used to prepare recombinant antibodies where one or more disulfide bonds are replaced with diselenide bonds. The one or more of the inter-chain disulfide bonds which link the heavy and light chains, the disulfide bonds that link two heavy chains, the disulfide bonds that link the two hinge regions, the intra-chain disulfide bonds, or combinations thereof can be replaced with diselenide bonds.

Disulfide bonds in antibodies are important for assembly, stability and dimerization of the antibody. For example, disulfide bonds play a critical role in the stabilization of the immunoglobulin β-sandwich. Under reducing conditions, such as those characteristic of recombinant protein expression systems, disulfide bonds do not normally form and as a result most antibodies expressed in that compartment are misfolded or inactive (Seo, et al., *Protein Sci.,* 18(2): 259-267 (2009)). Furthermore, stability and homogeneity of therapeutic antibodies are important for safety and efficacy of therapeutic antibodies (McAuley, et al, *Protein Sci.,* 17(1): 95-106 (2008)). Undesired biochemical, structural, and conformational forms, such as those generated when disulfide bonds are reduced, can lead to loss of efficacy and risk of adverse side effects.

Replacing one or more of the disulfide bonds of an antibody with diselenide or selenocysteine-cysteine bonds according to the disclosed compositions and methods can improve the yield, purity, or combinations thereof, of recombinantly produced antibodies. Replacing one or more of the disulfide bonds of an antibody with diselenide or selenocysteine-cysteine bonds according to the disclosed compositions and methods can also improve stability, increase efficacy, increase half-life, reduce toxicity, alter the pharmacokinetics of the antibody, for example, increase or decrease the association or dissociation constant, or combinations thereof of antibodies, such as therapeutic antibodies.

The antibodies can be xenogeneic, allogeneic, syngeneic, or modified forms thereof, such as humanized, single chain or chimeric antibodies. Antibodies may also be anti-idiotypic antibodies specific for a idiotype of the desired antigen. The term "antibody" is also meant to include both intact molecules as well as fragments thereof that include the antigen-binding site and are capable of binding to a desired epitope. These include Fab and F(ab')$_2$ fragments which lack the Fc fragment of an intact antibody, and therefore clear more rapidly from the circulation, and may have less non-specific tissue binding than an intact antibody (Wahl et al., *J. Nuc. Med.* 24:316-325 (1983)). Also included are Fv fragments (Hochman, J. et al., *Biochemistry,* 12:1130-1135 (1973); Sharon, J. et al., *Biochemistry,* 15:1591-1594 (1976)). These various fragments can be produced using conventional techniques such as protease cleavage or chemical cleavage (see, e.g., Rousseaux et al., *Meth. Enzymol.,* 121:663-69 (1986)).

Antibody "formats" and methods of making recombinant antibodies are known in the art and reviewed in Laffly and Sodoyer, *Hum Antibodies,* 14(1-2):33-35 (2005). Methods of expressing and purifying antibodies from a recombinant expression system are known in the art, see for example, Knappik and Brundiers, "Recombinant Antibody Expression and Purification," *The Protein Protocols Handbook,* Third Edition Edited by: J. M. Walker© Humana Press, a Part of Springer Science+Business Media, LLC (2009).

Therapeutic antibodies that could benefit from replacement of one or more disulfide bonds with a diselenide or selenocysteine-cysteine bond are known in the art and include, but are not limited to, those discussed in Reichert, *Mabs,* 3(1): 76-99 (2011), for example, AIN-457, bapineuzumab, brentuximab vedotin, briakinumab, dalotuzumab, epratuzumab, farletuzumab, girentuximab (WX-G250), napturnomab estafenatox, necitumumab, obinutuzumab, otelixizumab, pagibaximab, pertuzumab, ramucirumab, REGN88, reslizurnab, solanezumab, T1h, teplizumab, trastuzumab emtansine, tremelimumab, vedolizumab, zalutumumab and zanolimumab.

Other therapeutic antibodies that could benefit from replacement of one or more disulfide bonds with a diselenide bond include antibodies approved for use, in clinical trials, or in development for clinical use which include, but are not limited to, rituximab (Rituxan®, IDEC/GenentechlRoche) (see for example U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT/US2003/040426, entitled "Immunoglobulin Variants and Uses Thereof"), trastuzumab (Herceptin®, Genentech) (see for example U.S. Pat. No. 5,677,171), a humanized anti-Her2/neu antibody approved to treat breast cancer; pertuzumab (rhuMab-2C4, Omnitarge), currently being developed by Genentech; an anti-Her2 antibody described in U.S. Pat. No. 4,753,894; cetuximab (Erbitux®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Ser. No. 10/172,317), currently being developed by Genmab; 425, EMD55900, EMD62000, and EMD72000 (Merck KGaA) (U.S. Pat. No. 5,558,864; Murthy et al. 1987, Arch Biochem Biophys. 252(2):549-60; Rodeck et al., 1987, J Cell Biochem. 35(4):315-20; Kettleborough et al., 1991, Protein Eng. 4(7):773-83); 1CR62 (Institute of Cancer Research) (PCT WO 95/20045; Modjtahedi et al., 1993, J. Cell Biophys. 1993, 22(l-3):129-46; Modjtahedi et al., 1993, Br J Cancer. 1993, 67(2):247-53; Modjtahedi et al, 1996, Br J Cancer, 73(2):228-35; Modjtahedi et al, 2003, Int J Cancer, 105(2):273-80); TheraCIM hR3 (YM Biosciences, Canada and Centro de Immunologia Molecular, Cuba (U.S. Pat. No. 5,891,996; U.S. Pat. No. 6,506,883; Mateo et al, 1997, Immunotechnology, 3(1):71-81); mAb-806 (Ludwig Institue for Cancer Research, Memorial Sloan-Kettering) (Jungbluth et al. 2003, Proc Natl Acad Sci USA. 100(2):639-44); KSB-102 (KS Biomedix); MRI-1 (IVAX, National Cancer Institute) (PCT WO 0162931A2); and SC100 (Scancell) (PCT WO 01/88138); alemtuzumab (Campath®, Millenium), a humanized mAb currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Arnevive®), anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFalpha antibody developed by Centocor, adalimumab (Humira®), an anti-TNFalpha antibody developed by Abbott, Humicade®, an anti-TNFalpha antibody developed by Celltech, golimumab (CNTO-148), a fully human TNF antibody developed by Centocor, etanercept (Enbrel®), an p75 TNF receptor Fc fusion developed by Immunex/Amgen, lenercept, an p55TNF receptor Fc fusion previously developed by Roche, ABX-CBL, an anti-CD 147 antibody being developed by Abgenix, ABX-IL8, an anti-IL8 antibody being developed by Abgenix, ABX-MAI, an anti-MUC18 antibody being developed by Abgenix, Pemtumomab (R1549,90Y-muH-MFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegrene (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-.beta.2 antibody being developed by Cambridge Antibody Technology, ABT 874 (J695), an anti-IL-12 p40 antibody being developed by Abbott, CAT-192, an anti-TGF.beta.1 antibody being developed by Cambridge Antibody Technology and Genzyme, CAT-213, an anti-Eotaxinl antibody being developed by Cambridge Antibody Technology, LyntphoStat-B® an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc. Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech. Xolair® (Omalizurnab), an anti-IgE antibody being developed by Genentech, Raptiva® (Efalizurnab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GeoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDFC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (labetuzurnab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-I), and anti-Her2 antibody being developed by Medarex and Immuno-Designed Molecules, HuMaxe-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J. CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAFO, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, Xolair® (Omalizumab) a humanized anti-IgE antibody developed by Genentech and Novartis, and MLN01, an anti-Beta2 integrin antibody being developed by Xoma. In another embodiment, the therapeutics include KRN330 (Kirin); huA 33 antibody (A33, Ludwig Institute for Cancer Research); CNTO 95 (alpha V integrins, Centocor); MEDI-522 (alpha V133 integrin, Medimmune); volociximab (αVβ1 integrin, Biogen/PDL); Human mAb 216 (B cell glycosolated epitope, NCI); BiTE MT103 (bispecific CD19x CD3, Medimmune); 4G7x H22 (Bispecific BcellxFcgam-maR1, Meclarex/Merek KGa); rM28 (Bispecific CD28 x MAPG, U.S. Pat. No. EP1444268); MDX447 (EMD 82633) (Bispecific CD64 x EGFR, Medarex); Catumaxomab (remo-vah) (Bispecific EpCAM x anti-CD3, Trion/Fres); Ertumax-omab (bispecific HER2ICD3, Fresenius Biotech); oregov-omab (OvaRex) (CA-125, ViRexx); Rencarex® (WX G250) (carbonic anhydrase IX, Wilex); CNTO 888 (CCL2, Centocor); TRC105 (CD105 (endoglin), Tracon); BMS-663513 (CD137 agonist, Brystol Myers Squibb); MDX-1342 (CD 19, Medarex); Siplizumab (MEDI-507) (CD2, Medimmune); Ofaturnumab (Humax-CD20) (CD20, Genmab); Rituximab (Rituxan) (CD20, Genentech); THIOMAB (Genentech); veltuzumab (hA20) (CD20, Immunomedics); Epratuzumab (CD22, Amgen); lumiliximab (IDEC 152) (CD23, Biogen); muromonab-CD3 (CD3, Ortho); HuM291 (CD3 fc receptor, PDL Biopharma); HeFi-1, CD30, NCI); MDX-060 (CD30, Medarex); MDX-1401 (CD30, Medarex); SGN-30 (CD30, Seattle Genentics); SGN-33 (Lintuzumab) (CD33, Seattle Genentics); Zanolimumab (HuMax-CD4) (CD4, Genmab); HCD 122 (CD40, Novartis); SGN-40 (CD40, Seattle Genentics); CampathIh (Alemtuzumab) (CD52, Genzyme); MDX-1411 (CD70, Medarex); hLL1 (EPB-I) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Brystol Myers Squibb); Tremelimumab (Ticilimumab, CP-675,2) (CTLA4, Pfizer); 1-IGS-ETR1 (Mapatumumab) (DR4TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DR5TRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 (EGFRvIII, AVANT Immunotherapeuties); adecatumumab (MT201) (Eptam, Merck); edrecolomab (Panorex, 17-1A) (Epcam Glaxo/Centocor); MORAb-003 (folate receptor a, Morphotech); KW-2871 (ganglioside GD3, Kyowa); MORAb-009 (GP-9, Morphotech); CDX-1307 (MDX-1307) (hCGb, Celldex); Trastuzumab (Herceptin) (HER2, Celldex); Pertuzumab (rhuMAb 2C4) (HER2 (DI), Genentech); apolizumab (HLA-DR beta chain, PDL Pharma); AMG-479 (IGF-1R, Amgen); anti-IGF-1R R1507 (IGF1-R, Roche); CP 751871 (IGF 1-R, Pfizer); IMC-A12 (IGF1-R, Imclone); B1111022 Biogen); Mils-beta-1 (IL-2Rb (CD122), Hoffman LaRoche); CNTO 328 (IL6, Centocor); Anti-KIR (1-7F9) (Killer cell Ig-like Receptor (KIR), Novo); Hu3S193 (Lewis (y), Wyeth, Ludwig Institute of Cancer Research); hCBE-11 (LTβR, Biogen); HuHMFG1 (MUC1, Antisoma/NCI); RAV 12 (N-linked carbohydrate epitope, Raven); CAL (parathyroid hormone-related protein (PTH-rP), University of California); CT-011 (PD1, CtireTech); MDX-1106 (ono-4538) (PDL Nileclarox/Ono); MAb CT-011 (PD1, Curetech); IMC-3G3 (PDGFRa, Imclone); bavituximab (phosphatidylserine, Peregrine); hu7591 (PSMA, Cornell Research Foundation); mu.1591 (PSMA, Cornell Research Foundation); GC1008 (TGFb (pan) inhibitor (IgG4), Genzyme); Infliximab (Remicade) (TNFα, Centocor); A27.15 (transferrin receptor, Salk Institute, INSERN WO 2005/111082); E2.3 (transferrin receptor, Salk Institute); Bevacizumab (Avastin) (VEGF, Genentech); HuMV833 (VEGF, Tsukuba Research Lab-WO/2000/

034337, University of Texas); IMC-18F1 (VEGFR1, Imclone); IMC-1121 (VEGFR2, Imclone).

In another embodiment, the recombinant protein is a fusion protein having a least one Cys, preferably at least one Cys-Cys bond. In some embodiments, the fusion protein is a fusion protein containing an antibody domain, for example an Ig fusion protein. A fusion protein typically includes two or more domains, where a first domain including a peptide of interest is fused, directly or indirectly to a second polypeptide. In some embodiments, the second domain includes one or more domains of an Ig heavy chain constant region, preferably having an amino acid sequence corresponding to the hinge, $C_{H2}$ and $C_{H3}$ regions of a human immunoglobulin Cγ1 chain. Construction of immunoglobulin fusion proteins is discussed in *Current Protocols in Immunology*, (ed. Diane Hollenbaugh, Alejandro Aruffo) UNIT 10.19A, Published May 1, 2002, by John Wiley and Sons, Inc.

3. Selenocysteine-Containing Polypeptide Conjugates

In some embodiments, the addition of one or more selenocysteines can be used to facilitate linkage of second therapeutic, prophylactic or diagnostic agent to the selenocysteine containing polypeptide. Methods of utilizing cysteines as reactive sites for attachment of a second agent, for example, via a disulfide bridge, are known in the art. See for example, Ritter, *Pharmaceutical Technology*, 42-47 (2012); Miao, et al., *Bioconjug. Chem.*, 19(1):15-19 (2008); and Dosio, et al., *Toxins (Basel)*, 3(7):848-83 (2011). Accordingly, one or more selenocysteines can be added to a recombinant polypeptide, or substitute for an existing amino acid such as cysteine, to create or replace a reactive site for conjugation of the second agent. The recombinant polypeptide and the second agent can be conjugated via a linker. In a preferred embodiment, the recombinant polypeptide engineered to a contain one or more selenocysteines is an antibody, for example a therapeutic antibody.

In some embodiments, the second agent is a toxin, diagnostic imaging agent, purification ligand or other engineered element that modifies the stability, activity, pharmacokinetics, or other properties of the protein. The second agent can be a small molecule.

In a preferred embodiment, the second agent is a therapeutic agent. For example, the second agent can be a chemotherapeutic drug. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

In some preferred embodiments, recombinant antibody including one or more selenocysteine polypeptides manufactured according to the disclosed methods is conjugated with second therapeutic agent such as a chemotherapeutic drug.

Conditions to be Treated

As discussed above, substituting one or more naturally occurring Cys residues with a Sec can increase activity, lower dosage, reduce toxicity, improve stability, increase efficacy, increase half-life or combinations thereof of a selenocysteine containing protein relative to its cysteine containing counterpart. Accordingly, therapeutic proteins containing one or more selenocysteine residues can be prepared according to the compositions and methods disclosed herein and administered to a subject in need thereof in an effective amount to reduce or alleviate one or more symptoms of a disease or disorder. Therapeutic proteins such as enzymes and antibodies which contain one or more cysteine residues or disulfide bonds can be replaced with Sec to increase activity, lower dosage, reduce toxicity, improve stability, increase efficacy, increase half-life, or attach a second agent or combinations thereof are discussed above and known in the art, and can be administered to subject to treat diseases or disorders including, but not limited to, infectious diseases, cancers, metabolic disorders autoimmune disorders, inflammatory disorders, and age-related disorders.

C. Administration

The recombinant selenocysteine containing polypeptides disclosed herein can be part of a pharmaceutical composition. The compositions can be administered in a physiologically acceptable carrier to a host. Preferred methods of administration include systemic or direct administration to a cell. The compositions can be administered to a cell or patient, as is generally known in the art for protein therapy applications.

The compositions can be combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween®, Pluronics or PEG.

The compositions can be administered parenterally. As used herein, "parenteral administration" is characterized by administering a pharmaceutical composition through a physical breach of a subject's tissue. Parenteral administration includes administering by injection, through a surgical incision, or through a tissue-penetrating non-surgical wound, and the like. In particular, parenteral administration includes subcutaneous, intraperitoneal, intravenous, intraarterial, intramuscular, intrasternal injection, and kidney dialytic infusion techniques.

Parenteral formulations can include the active ingredient combined with a pharmaceutically acceptable carrier, such as sterile water or sterile isotonic saline. Such formulations may be prepared, packaged, or sold in a form suitable for bolus administration or for continuous administration.

Injectable formulations may be prepared, packaged, or sold in unit dosage fouii, such as in ampules or in multi-dose containers containing a preservative. Parenteral administration formulations include suspensions, solutions, emulsions in oily or aqueous vehicles, pastes, reconstitutable dry (i.e. powder or granular) formulations, and implantable sustained-release or biodegradable formulations. Such formulations may also include one or more additional ingredients including suspending, stabilizing, or dispersing agents. Parenteral formulations may be prepared, packaged, or sold in the form of a sterile injectable aqueous or oily suspension or solution. Parenteral formulations may also include dispersing agents, wetting agents, or suspending agents described herein.

Methods for preparing these types of formulations are known. Sterile injectable formulations may be prepared using non-toxic parenterally-acceptable diluents or solvents, such as water, 1,3-butane diol, Ringer's solution, isotonic sodium chloride solution, and fixed oils such as synthetic monoglycerides or diglycerides. Other parentally-administrable formulations include microcrystalline forms, liposomal preparations, and biodegradable polymer systems. Compositions for sustained release or implantation may include pharmaceutically acceptable polymeric or hydrophobic materials such as emulsions, ion exchange resins, sparingly soluble polymers, and sparingly soluble salts.

Pharmaceutical compositions may be prepared, packaged, or sold in a buccal formulation. Such formulations may be in the form of tablets, powders, aerosols, atomized solutions, suspensions, or lozenges made using known methods, and may contain from about 0.1% to about 20% (w/w) active ingredient with the balance of the formulation containing an orally dissolvable or degradable composition and/or one or more additional ingredients as described herein. Preferably, powdered or aerosolized formulations have an average particle or droplet size ranging from about 0.1 nanometers to about 200 nanometers when dispersed.

As used herein, "additional ingredients" include one or more of the following: excipients, surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which may be included in the pharmaceutical compositions are known. Suitable additional ingredients are described in Remington's Pharmaceutical Sciences, Mack Publishing Co., Genaro, ed., Easton, Pa. (1985).

Dosages and desired concentrations of the pharmaceutical compositions disclosed herein may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

EXAMPLES

Example 1

Construction of Exemplary Non-Naturally Occurring tRNA$^{Sec}$

PSTK recognizes certain key bases (called identity elements) in the Sep-tRNA$^{Sec}$ substrate. These have been investigated by tRNA mutagenesis and subsequent transplantation of the tRNA$^{Sec}$ identity elements into a tRNA$^{Ser}$ body. The major M. maripaludis tRNA$^{Sec}$ identity elements G2-C71 and C3-G70 were transplanted into M. maripaludis tRNA$^{Ser}$ UGA.

Mutation of the tRNA$^{Ser}$ negative determinant A5-U68 to the C5-G68 base pair present in tRNA$^{Sec}$ resulted in a tRNA$^{Ser}$ variant that phosphorylated with a relative efficiency of 68% as compared to wild-type tRNA$^{Sec}$.

Another mutant tRNA with an 8 bp acceptor stem (FIG. 4A) could be converted to Sep-tRNA$^{Sec}$ with 31% relative efficiency.

Thus, different variants of M. maripaludis tRNA$^{Ser}$ and tRNA$^{Sec}$ are properly recognized by PSTK.

Figure 4:
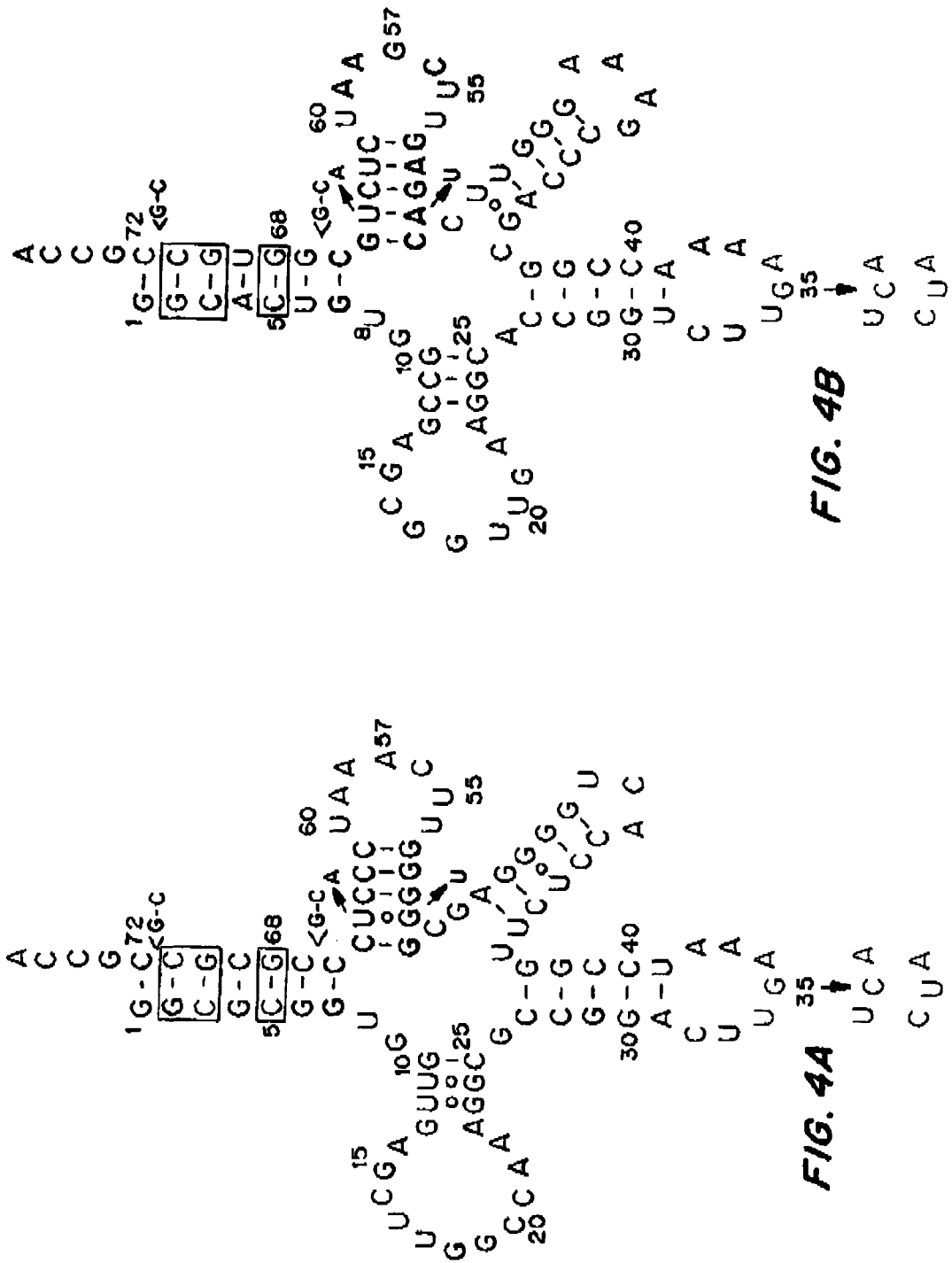
FIGS. 4A and 4B are depictions of the primary and secondary structures of a non-naturally occurring tRNA$^{UTu}$ with a body derived from *M. maripaludis* (FIG. 4A, tRNA$^{Utu}_{UCA}$, SEQ ID NO:57; tRNA$^{UTu}_{op}$, SEQ ID NO:33; tRNA$^{Utu}_{am}$, SEQ ID NO:34) and a non-naturally occurring tRNA$^{UTu}$ with a body derived from *E. coli* (FIG. 4B, tRNA$^{Utu}_{UCA}$, SEQ ID NO:58, tRNA$^{UTu}_{op}$, SEQ ID NO:9; tRNA$^{Utu}_{am}$, SEQ ID NO:10). Transplanted PSTK identity elements are boxed. "<" identifies potential locations of additional base pairs in the acceptor stem. "Arrow" identifies the location of other possible mutations. Specifically, the < depict one possible insertion of a G-C base pair between the 1$^{st}$ and 2$^{nd}$ base pair and a second possible insertion of a G-C pair insertion between the 6$^{th}$ and 7$^{th}$ base pair of the acceptor stem. The arrows depict a possible change in the 50:64 base pair (A-U) to a U-A pair, and substitution of the serine anticodon (UGA) with opal (UCA) or amber (CUA) anticodon.

Since E. coli is a system for Sec incorporation, tRNA$^{UTu}$ candidates derived from the E. coli tRNA$^{Ser}$ body were also designed (FIGS. 3 and 4). E. coli tRNA$^{Ser}$ serves as a major scaffold for tRNA$^{UTu}$, with the exception of the acceptor stem that originates from E. coli tRNA$^{Sec}$ (FIG. 3, center panel, boxed sequence elements). Major EF-Tu recognition elements were retained from tRNA$^{Ser}$ as well (FIG. 3, center panel, circled sequence elements). The amber anti-codon CUA constitutes tRNA$^{UTu}_{am}$ whereas the opal anti-codon UCA constitutes tRNA$^{UTu}_{op}$.

The experiments described below utilize the tRNA$^{UTu}_{am}$ or the tRNA$^{UTu}_{op}$, depicted in FIG. 3, center panel (SEQ ID NO:7 and SEQ ID NO:6 respectively), as indicated.

Example 2

Ser-tRNA$^{UTu}_{am}$ Forms Sec-tRNA$^{UTu}_{am}$

In vitro Ser-tRNA$^{UTu}_{am}$ conversion was confirmed by TLC separation of [$^{32}$P] Amp, [$^{32}$P] Ser-Amp and [$^{32}$P] Sec-Amp recovered by nuclease P1 treatment from [$\alpha^{32}$P] ATP radiolabeled tRNA$^{UTu}_{am}$, tRNA$^{UTu}_{am}$ after serylation and Ser-tRNA$^{UTu}_{am}$ after incubation in an in vitro Sec formation assay. The TLC was developed for 90 min under acidic conditions using 100 mM ammonium acetate and 5% acetic acid.

Example 3 tRNA$^{UTu}$ Forms the Active Selenoenzyme Formate Dehydrogenase H

Formate Dehydrogenase H (FDH$_H$) is a selenocysteine containing E. coli enzyme of known structure (Boyington, et al., Science, 275:1305-08 (1997)). A sequence encoding wildtype FDH$_H$ (FDH$_{Hop}$) or an FDH$_H$ (FDH$_{Ham}$) engineered to replace the opal codon with an amber codon was expressed in E. coli strain MH5 (BW25113 selA selB fdhF).

Figure 5:
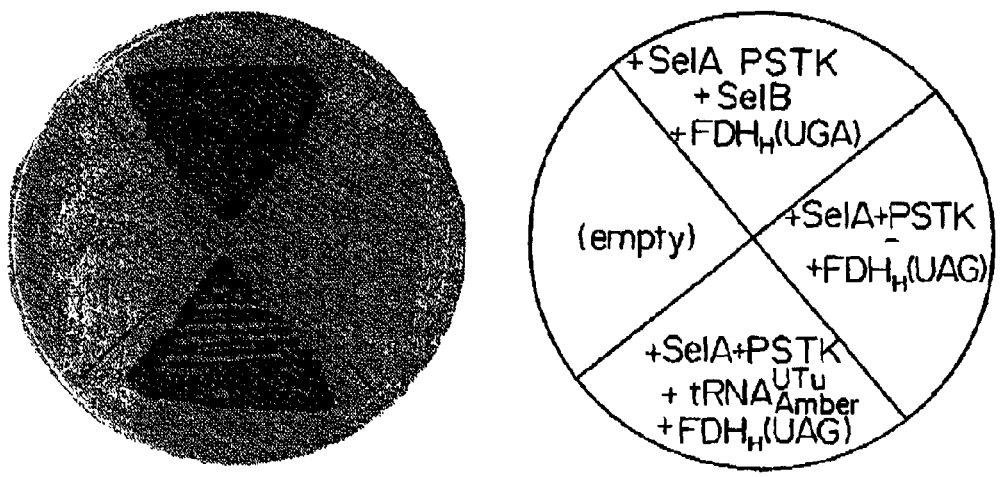
FIG. 5 is a photograph showing FDH$_H$ activity in *E. coli* MH5 (selA, selB, fdhF mutant) strain transformed with (clockwise from top) (1) SelA+PSTK+SelB+FDH$_H$(UGA); (2) SelA+PSTK+FDH$_H$(UAG); (3) SelA+PSTK+tRNA$^{Utu}$(amber)+FDH$_H$(UAG); (4) empty plasmid.

As shown in FIG. 5, tRNA$^{UTu}$ mediates functional Sec suppression in FDH$_H$ E. coli strain MH5 which was complemented with E. coli SelA, M. jannaschii PSTK, and either tRNA$^{UTu}_{op}$ and FDH$_{H\ op}$ (1) or tRNA$^{UTu}_{am}$ and FDH$_{H\ am}$ (4) and grown anaerobically on LB selective medium supplemented with 0.01 mM IPTG at 30° C. for 24 h. Controls used the same experimental setup with either tRNA$^{UTu}_{op}$ (2) or tRNA$^{UTu}_{am}$ (3) omitted and tested the combinations of FDH$_{H\ op}$ and FDH$_{H\ am}$ with genomically encoded *E. coli* tRNA$^{Sec}$ and plasmid encoded selB instead. Cells were overlaid with a top agar containing sodium formate and benzyl viologen. FDH$_H$ activity was then assessed by occurrence of a purple coloration upon reduction of benzyl viologen.

Example 4

$^{75}$Se Incorporates into *E. Coli* Selenoprotein FDH$_H$

Cells were grown in the presence of [$^{75}$Se]-selenite in LB medium supplemented with 100 μM IPTG for protein overexpression.

6× His-tagged FDH$_H$ fusion protein was purified and detected by SDS-Page and autoradiography of the gel, with FDH$_H$ corresponding to the protein band at a relative molecular weight of approximately 80,000 Da.

Example 5

Sec Complements Thymidylate Synthase A Active Site Residue Cys146

Thymidylate Synthase (ThyA) is an *E. coli* enzyme with a Cys in the active site. When the Cys is replaced with a Ser, the protein loses its enzymatic activity.

Figure 6:
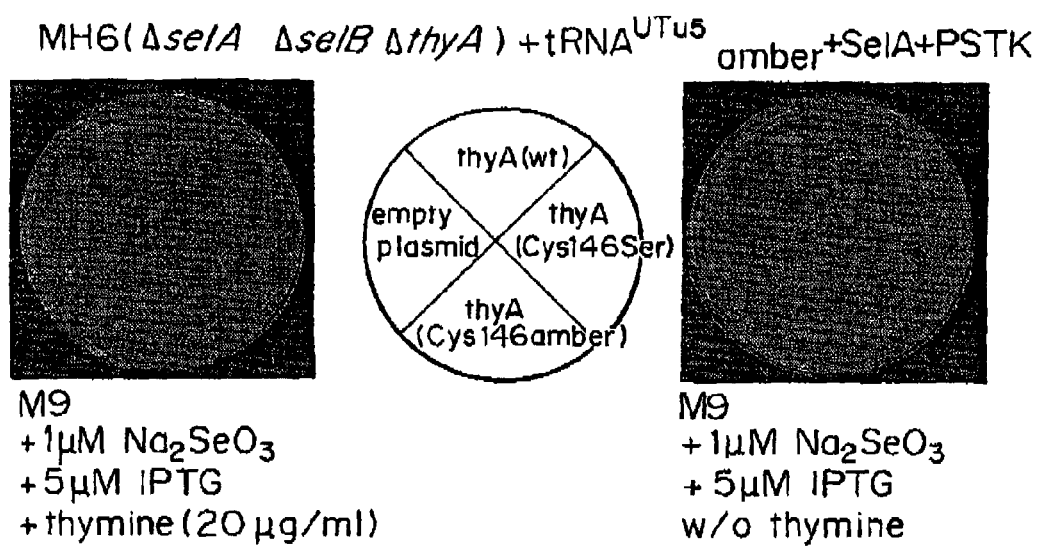
FIG. 6 is a photograph showing thymidylate synthase activity in *E. coli* MH6 (selA, selB, thyA mutant) strain transformed with (clockwise from top) (1) tRNA$^{UTu}$(amber)+SelA+PSTK+thyA (wildtype); (2) tRNA$^{UTu}$(amber)+SelA+PSTK+thyA (Cys146Ser); (3) tRNA$^{UTu}$(amber)+SelA+PSTK+thyA (Cys146amber); (4) empty plasmid; grown in M9+1 μM Na$_2$SeO$_3$+5 μM IPTG+thymine (20 μg/ml) (left panel) or M9+1 μM Na$_2$SeO$_3$+5 μM IPTG+w/o thymine (right panel).

As shown in FIG. 6, *E. coli* MH6 (lacking ThyA) was complemented with expression constructs encoding either ThyA$_{WTCys}$ (Cys146), ThyA$_{Ser}$ (Cys146Ser) or ThyA$_{am}$ (Cys146Sec) alongside with tRNA$^{UTu}_{am}$ and SelA.

All clones showed growth on LB agar plates while only ThyA$_{am}$ (Cys146Sec) was able to reconstitute the wild type phenotype (ThyA$_{WTCys}$) on M9 minimal medium in the absence of thymine.

Example 6

Characterization of Grx1 and GPx1 Mutants

Glutaredoxin-1 (Grx1) is an enzyme with a Cys in the active site, which is inactive when replaced with a Ser. Constructs were created for expression of Grx1$_{C11am/C14S}$Sec (where the Cys 11 codon is replaced with an amber codon that is recognized by a tRNA$^{UTu}_{amber}$), a Grx1$_{C11S/C14S}$ (where the Cys 11 codon is replaced with a serine codon) and Grx1$_{C14S}$ (and wherein Cys 11 codon encodes Cys).

Figure 7A:
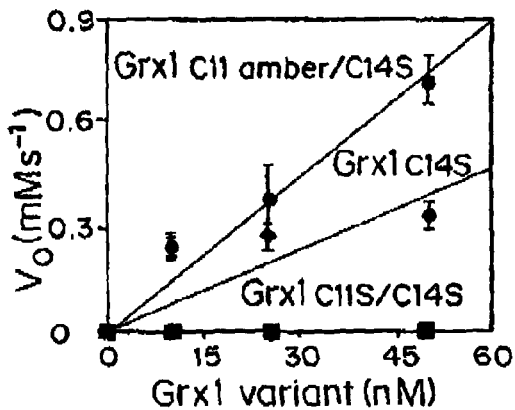
FIG. 7A is a line graph showing the disulfide oxidoreductase activity (V$_0$(mMs$^{-1}$)) of Grx1$_{C11am/C14S}$Sec, Grx1$_{C11S/C14S}$ and Grx1$_{C14S}$ at increasing concentrations (nM).

FIG. 7A shows Sec dependent glutathione disulfide oxidoreductase activity. Pure Grx1$_{C11am/C14S}$Sec, Grx1$_{C11S/C14S}$ and Grx1$_{C14S}$ were tested for disulfide oxidoreductase activity. The reduction of a mixed disulfide between β-hydroxyethyldisulfide (HED) and glutathione by Grx1 variants is coupled to NADPH consumption by glutathione reductase. Glutathione reductase reconstitutes the reduced Grx1. The reaction was followed at 340 nm at 25° C. as a function of Grx1 concentration.

Figure 7B:
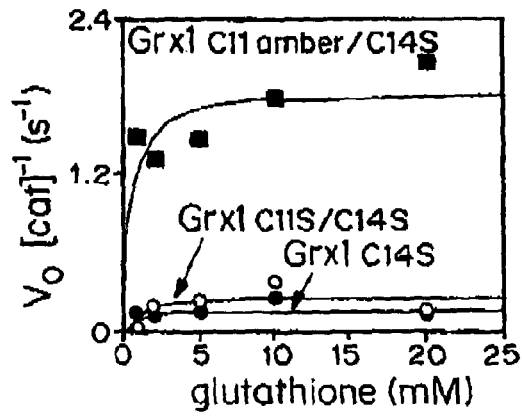
FIG. 7B is a line graph showing the peroxidase activity (V$_0$[cat]$^{-1}$ (s$^{-1}$)) of Grx1$_{C11am/C14S}$Sec, Grx1$_{C11S/C14S}$ and Grx1$_{C14S}$ as a function of reduced glutathione concentration at 25° C. (mM).

Pure Grx1$_{C11am/C14S}$Sec, Grx1$_{C11S/C14S}$ and Grx1$_{C14S}$ were also tested for peroxidase activity (FIG. 7B). The reduction of tBuOOH to the corresponding alcohol and water is coupled to the consumption of NADPH by glutathione reductase to reconstitute reduced Grx1. Peroxidase activity was determined at 340 nm as a function of reduced glutathione concentration at 25° C. Accordingly, peroxidase activity was determined by monitoring NADPH consumption at 340 nm as a function of the concentration of reduced glutathione at 25° C.

Figure 7C:
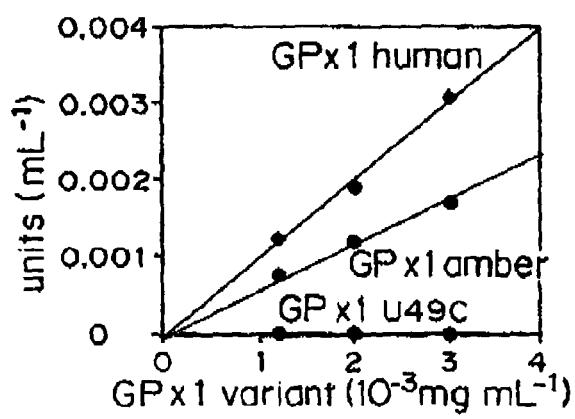
FIG. 7C is a line graph showing peroxidase activity (units (mL$^{-1}$)) of Sec containing GPx1$_{am}$ and Cys containing GPx1$_{Cys}$ that were overexpressed in *E. coli* and compared to commercially available GPx$_{hum}$ from human erythrocytes as a function of GPx1 (10$^{-3}$ mg mL$^{-1}$).

Peroxidase activity of Sec containing GPx1$_{am}$ and Cys containing GPx1$_{Cys}$ that were overexpressed in *E. coli* was compared to commercially available GPx$_{hum}$ from human erythrocytes (FIG. 7C). The activity was determined by using the glutathione peroxidase cellular activity assay kit.

Experiments shown in FIGS. 7A and 7C were performed in triplicates and error bars indicate the standard error of the mean.

Accordingly, substitution of Cys11 with Sec results in a protein with enzymatic activity, and in some assays, enhanced activity, while substitution of the Cys11 with serine results in a non-functional protein.

Figure 8:
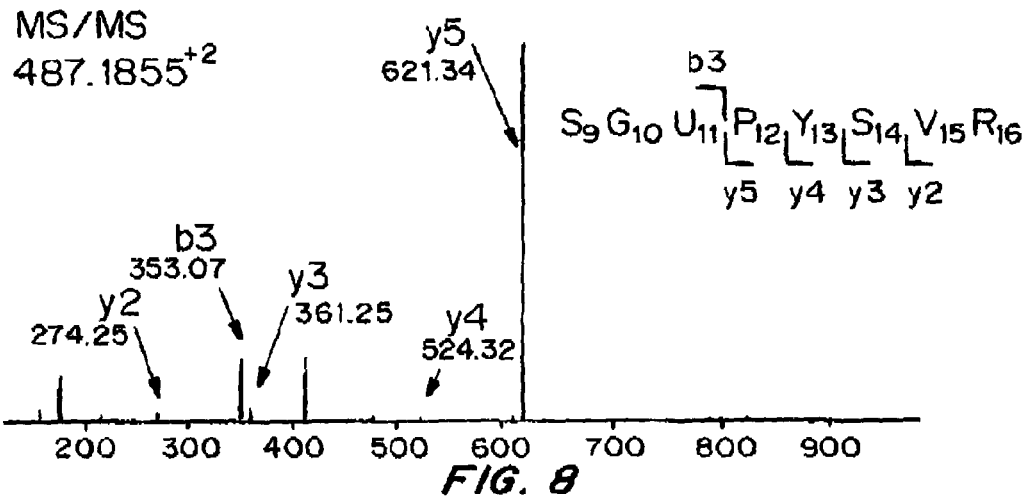
FIG. 8 is a spectrogram showing the presence of selenocysteine at amino acid position 11 in Grx1$_{C11am/C14S}$Sec by mass spectroscopy. Shown is the MS/MS spectrum of the trypsin-digested Sec-containing fragment S$_9$G$_{10}$U$_{11}$P$_{12}$Y$_{13}$S$_{14}$V$_{15}$R$_{16}$. Fragments observed in the second mass spectrometric analysis of this peptide are labeled with b3, y2, y3, y4 and y5. The Sec residue of the peptide in the MS/MS experiment was first treated with DTT, and then alkylated with iodoacetamide for oxidative protection of the selenol. The unit m/z describes the mass-to-charge ratio.

Sec incorporation was confirmed by mass spectroscopy (FIG. 8). The presence of selenocysteine at amino acid position 11 in Grx1$_{C11am/C14S}$Sec was confirmed by mass spectroscopy. Shown is the MS/MS spectrum of the trypsin-digested Sec-containing fragment S$_9$G$_{10}$U$_{11}$P$_{12}$Y$_{13}$S$_{14}$V$_{15}$R$_{16}$. Fragments observed in the second mass spectrometric analysis of this peptide are labeled with b3, y2, y3, y4 and y5. The Sec residue of the peptide in the MS/MS experiment was first treated with DTT, and then alkylated with iodoacetamide for oxidative protection of the selenol. The unit tn/z describes the mass-to-charge ratio.

Figure 9A:
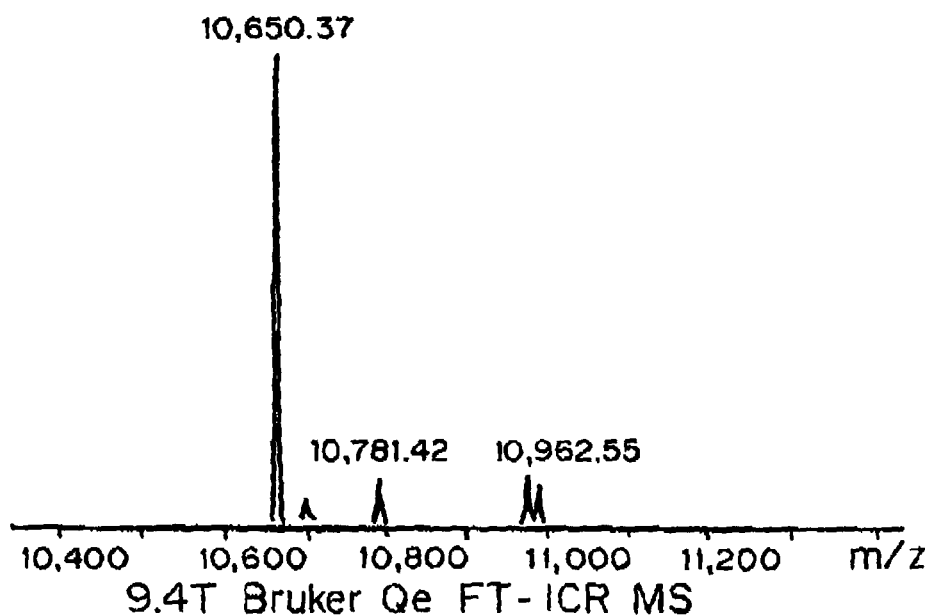
FIGS. 9A and 9B are spectrograms showing the results of Fourier transform ion cyclotron resonance (FT-ICR) mass spectrometry of Grx1$_{C11S/C14S}$ (calculated: 10,650 Da, found 10,651 Da) and Grx1$_{C11am/C14S}$ (calculated: 11,019 Da, found 11,019 Da).
Figure 9B:
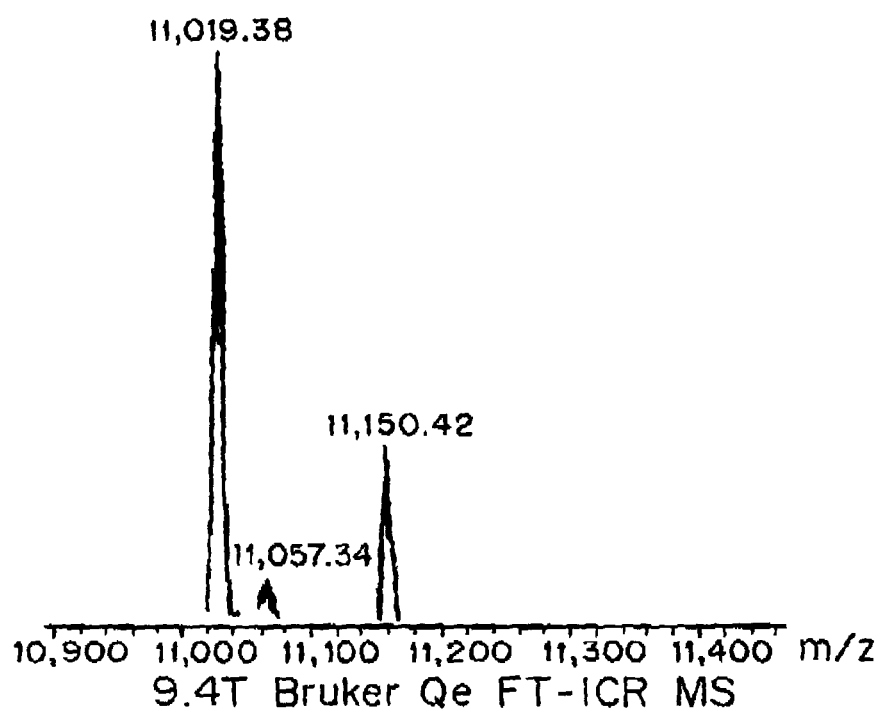
Figure 10:
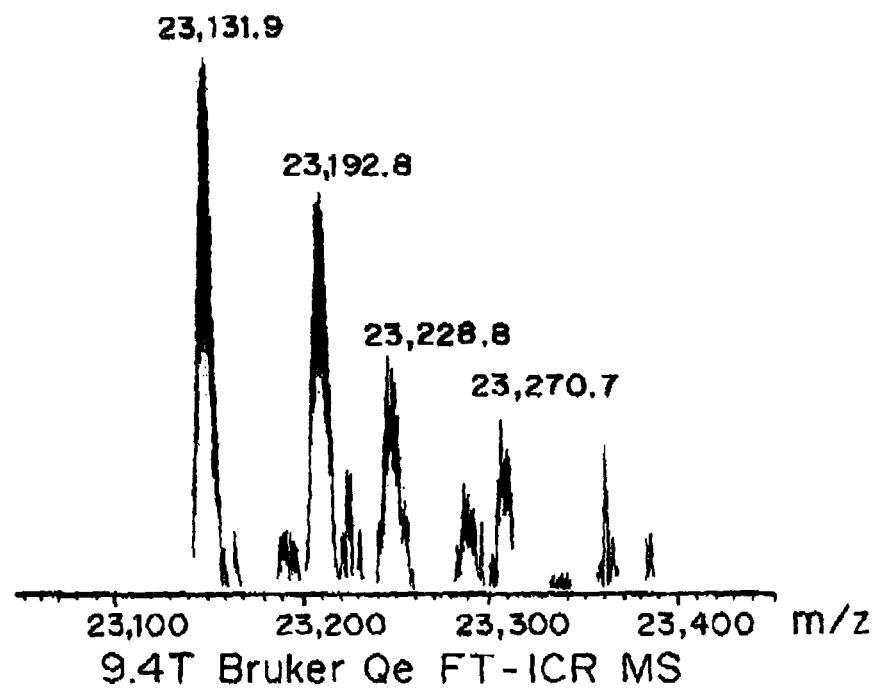
FIG. 10 is a spectrogram showing the results of Fourier transform ion cyclotron resonance (FT-ICR) mass spectrometry of GPx1am.

FIG. 9 is a spectrogram showing the results of Fourier transform ion cyclotron resonance (FT-ICR) mass spectrometry of Grx1$_{C11S/C14S}$ calculated: 10,650 Da, found 10,651 Da.

Sec incorporation was determined spectroscopically by assaying purified Grx1$_{C11amC14S}$ with DTNB (Ellman's reagent). Grx1$_{C11C/C14S}$ and Grx1$_{C11S/C14S}$ served as positive and negative controls respectively.

tRNA$^{UTu}_{amber}$ mediated Sec suppression in response to the Amber codon resulted in a mixture of Sec and Ser containing Grx1$_{C11am/C14S}$ species. From this mixture the Grx1$_{C11am/C14S}$Sec species was specifically recovered by an affinity chromatographic purification using Activated Thiol Sepharose™ 4B which selectively binds to selenol (thiol) moieties of Sec (Cys) but not to hydroxyl groups of Ser residues.

An overall of 2 mg of the Sec and Ser containing Grx1$_{C11am/C14S}$ mixture were desalted and loaded on an Activated Thiol Sepharose™ 4B gravity flow chromatography column and incubated with the resin (2 ml bed volume) for 30 mM. The column was then washed with lysis buffer (50 mM sodium phosphate, 100 mM NaCl, 1 mM EDTA, pH 7.0) to remove unbound Grx1$_{C11am/C14S}$Ser protein fraction. Subsequently, immobilized Grx1$_{C11am/C14S}$Sec proteins were eluted in the presence of 50 mM reduced glutathione in phosphate buffer. Overall 1.05 mg Grx1$_{C11am/C14S}$Sec was recovered from the Activated Thiol Sepharose™ 4B. This represents 52% of the overall Grx1 protein initially subjected to the Activated Thiol Sepharose™ 4B affinity chromatography. Homogeneity of the recovered Grx1$_{C11am/C14S}$Sec was accessed by mass spectrometry.

Grx1$_{C11amC14S}$ was recovered after affinity chromatography on Activated Thiol SEPHAROSE®. The peaks corresponded to the masses of a Grx1$_{C11amC14S}$ glutathione adduct (11,019.38), a glutathione plus K$^+$ adduct (11,057.34) and a glutathione plus Met adduct (11,150.42). The unit m/z describes the mass-to-charge ratio.

Figure 11A:
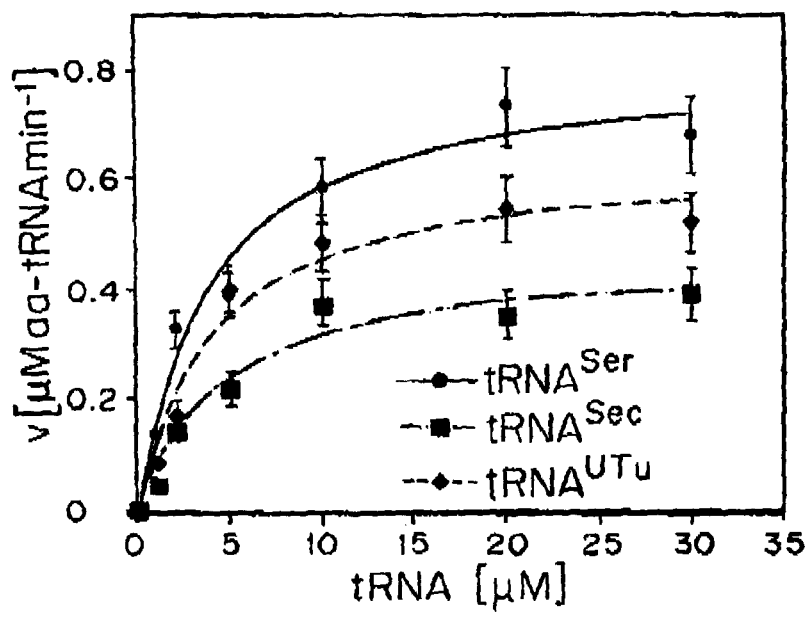
FIG. 11A is a line graph showing varying concentrations (1-30 μM) of tRNA$^{Ser}$ (-●-), tRNA$^{Sec}$ (-■-), and tRNA$^{Utu}$ (-♦-) in an assay for measuring kinetic parameter of each tRNA as a substrate for SerRS (v[μM aa-tRNAmin$^{-1}$]). Kinetic parameters were determined by Michaelis & Menten plots of the initial aminoacylation velocity versus substrate concentration.
Figure 11B:
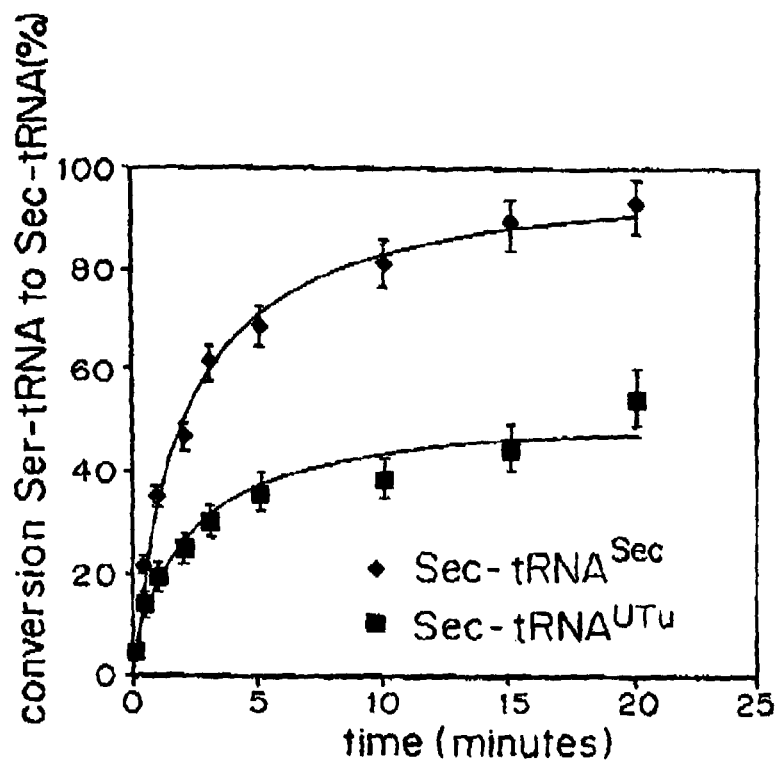
FIG. 11B is a line graph showing in vitro conversion of tRNA$^{Sec}$ (-♦-) and tRNA$^{UTu}$ (-■-) (Ser-tRNA to Sec-tRNA %) by SelA as a function of time (min).

FIGS. 11A and 11B shows SerRS kinetics for tRNA$^{Sec}$, tRNA$^{Ser}$ and tRNA$^{UTu}_{amber}$. Varying concentrations (1-30 μM) of tRNA$^{Ser}$, tRNA$^{Sec}$ and tRNA$^{UTu}_{amber}$ were incubated in the presence 30 μM L-[14C] serine, 500 nM *E. coli*

SerRS, 5 mM ATP at 37° C. Samples were taken in the linear range of the aminoacylation reaction and analyzed by scintillation counting. Kinetic parameters were determined by Michaelis-Menten plots of the initial aminoacylation velocity versus substrate concentration. Each, tRNA$^{Sec}$, tRNA$^{Ser}$ and tRNA$^{UTu}{}_{amber}$ showed similar kinetic parameters for aminoacylation with serine by SerRS. KM values were determined in the low μM-range around 5 μM and Kcat and Kcat/KM at approximately 0.015 s$^{-1}$ and 0.0025 s$^{-1}$μM$^{-1}$, respectively (FIG. 11A). Ser-tRNA$^{UTu}{}_{amber}$ is a substrate for SelA in vitro. While Ser-tRNA$^{Sec}$ is nearly completely converted to See-tRNA$^{Sec}$ by SelA, 50% conversion to Sec-tRNA$^{UTu}{}_{amber}$ is observed over a course of 20 minutes (FIG. 11B)

Figure 12:
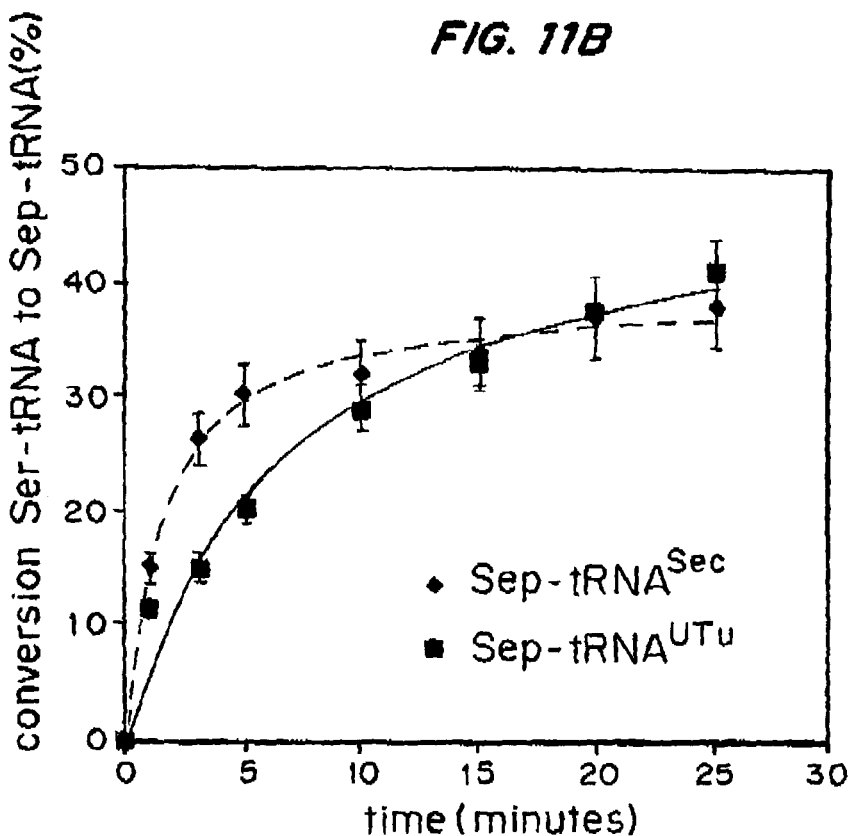
FIG. 12 is a line graph showing in vitro conversion of tRNA$^{Sec}$ (-♦-) and tRNA$^{UTu}$ (-■-) (Ser-tRNA to Sep-tRNA %) by PSTK as a function of time (min).

FIG. 12 shows in vitro conversion of tRNA$^{Sec}$ and tRNA$^{UTu}{}_{amber}$ by SelA. 5 μM SelD, 1 mM Na$_2$SeO$_3$ and 5 mM ATP were pre-incubated at pH 7.2 under anaerobic conditions at 37° C. for 30 min and then supplemented by 1 μM SelA and 10 μM of [α$^{32}$-P] radiolabeled Ser-tRNA$^{Sec}$ and Ser-tRNA$^{UTu}$ for up to 20 min. 1.5 μL aliquots taken at different time points were digested with Nuclease P1 and spotted onto cellulose thin layer chromatography plates After development the plates were analyzed by autoradiography. While Ser-tRNA$^{Sec}$ is nearly completely converted only approximately 50% of Sec-tRNA$^{UTu}$ is formed by SelA over a course of 20 min.

TABLE 1

Kinetic Parameters of tRNA$^{Sec}$ and tRNA$^{UTu}$

| tRNA | $K_M$ [μM] | $K_{cat}$ [s$^{-1}$] | $K_{cat}/K_M$ |
| --- | --- | --- | --- |
| E. coli tRNA$^{Sec}$ | 4.1 ± 1.0 | 0.02 | 0.005 |
| E. coli tRNA$^{Ser}$ | 5.7 ± 1.4 | 0.01 | 0.002 |
| tRNA$^{UTu}{}_{am}$ | 5.1 ± 1.1 | 0.012 | 0.0023 |

Figure 13A:
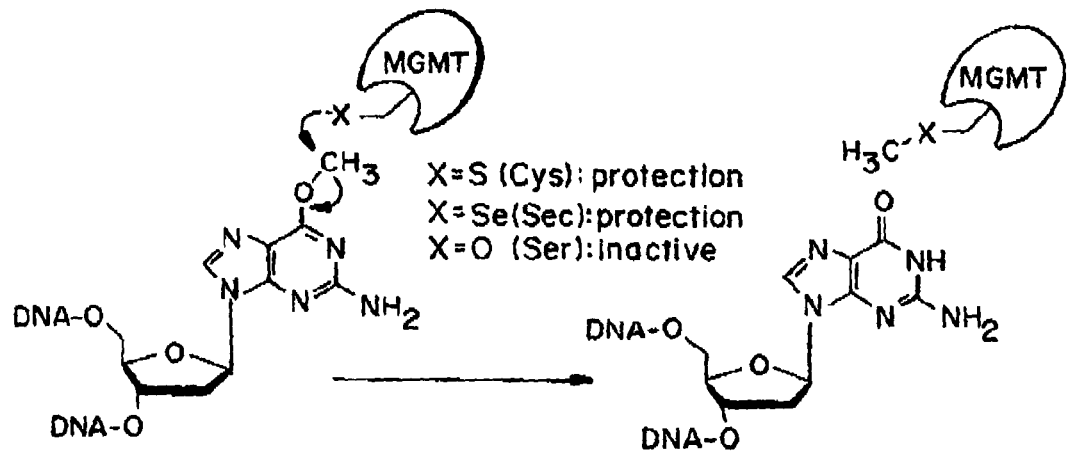
FIG. 13A is a structure diagram showing the activity of various O-6-methylguanine-DNA methyltransferase (MGMT) constructs on O6-methylguanine.
Figure 13B:
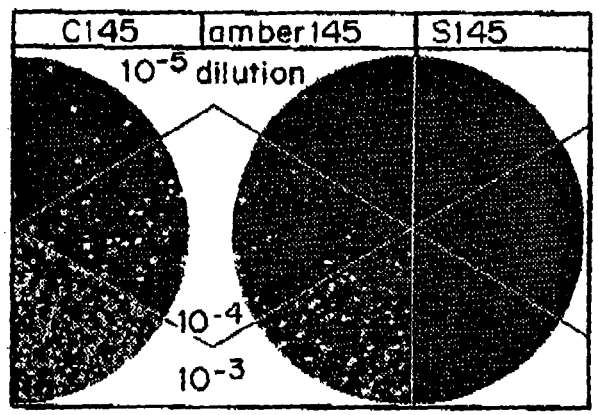
FIG. 13B is an image showing the activity (in number of living colonies) of *E. coli* Δada Δotg-1 cells expressing either MGMT C145, amber145 (Sec/Ser) or S145 mutant proteins, and tRNA$^{UTu}$ amber, pulsed 3× with N-Methyl-N-nitroso-N'-nitroguanidine.

FIG. 13 shows in vitro conversion of tRNA$^{Sec}$ and tRNA$^{UTu}{}_{amber}$ by PSTK. 10 μM of [α32-P] radiolabeled Ser-tRNA$^{Sec}$ and Ser-tRNA$^{UTu}$ were incubated at pH 7.2 in the presence of 5 μM *Methanococcus maripaludis* PSTK and 5 mM ATP under anaerobic conditions at 37° C. for up to 25 min. 1.5 μL aliquots taken at different time points were digested with Nuclease P1 and spotted onto cellulose thin layer chromatography plates. After development the plates were analyzed by autoradiography. Approximately 40% of both, Ser-tRNA$^{Sec}$ and Ser-tRNA$^{UTu}$ are converted to phosphoseryl-(Sep-)tRNA by PSTK over a course of 25 min.

Example 7

Sec Complements MGMT Active Site Residue Cys145

O-6-methylguanine-DNA methyltransferase (MGMT) is an enzyme that can protect the alkyltransferase-deficient *E. coli* Δada, Δogt-1 strain from the DNA methylating agent N-methyl-N'-nitro-N-nitrosoguanidine (Christians, et al., *PNAS*, 93:6124-6128 (1996)). MGMT is capable of transferring the methyl group from DNA with O6-methylguanine to the wild-type Cys145 and designed Sec145, but not to Ser145 at the active site in a single turn over reaction. *E. coli* Dada Dotg-1 cells expressing either (MGMT) Cys145, amber145 (Sec/Ser) or Ser145 mutant proteins transformed with tRNA$^{UTu}{}_{amber}$ were pulsed 3× with N-Methyl-N-nitroso-N'-nitroguanidine. Dilutions of the cell cultures were plated to indicate cellular protection through active MGMT as shown by growth.

FIG. 13 shows amber145 rescues MGMT enzyme activity while Ser145 is inactive, relative to a Cys145 control.

Example 8

Genetic Optimization Increases tRNA$^{UTu}$ Mediated Sec Incorporation tRNA$^{UTu}$ mediated Sec incorporation into Grx1$_{C11amC14S}$ was gradually increased by genetic optimization of the expression system. Initially Grx1 was expressed under the control of an IPTG inducible T7 promoter. The change from genomically encoded SelA to inducible recombinant SelA increased the Sec incorporation ratio from 23% to 37%.

Figure 14:
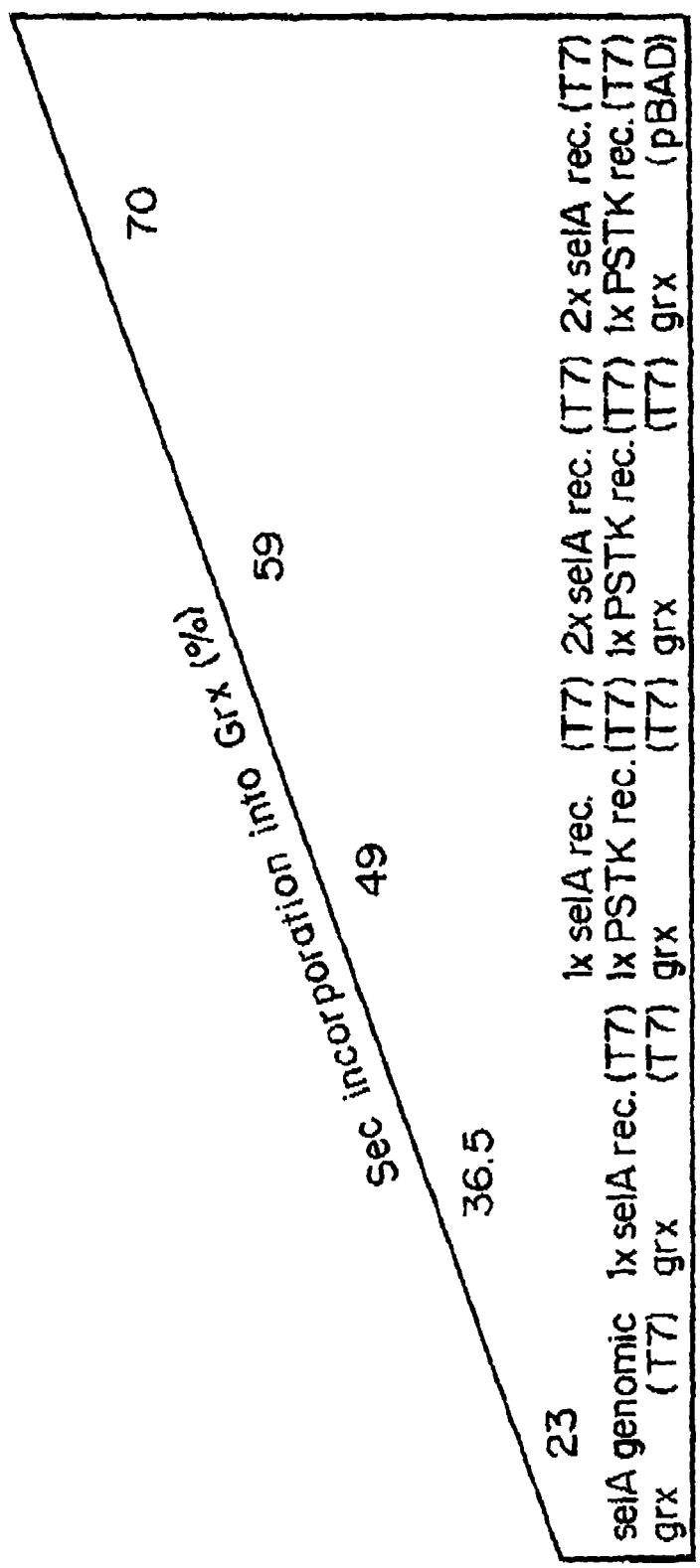
FIG. 14 is a diagram showing genomic factors in *E. coli* that increase Sec incorporation into the recombinantly expressed selenocysteine containing protein Grx (%).

A further increase to 49% was obtained by adding T7 controlled *Methanococcus janaschii* PSTK that was codon optimized for the *E. coli* expression host. By adding a second selA copy Sec insertion increased to 59% while up to 70% incorporation were obtained after the Grxl reporter was expressed independently from SelA and PSTK under the control of an arabinose inducible PBAD promoter (FIG. 14).

We claim:

1. A non-naturally occurring tRNA$^{Sec}$ comprising a nucleic acid sequence according to SEQ ID NO: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, or 58.

2. An isolated nucleic acid comprising a nucleic acid sequence encoding a non-naturally occurring tRNA$^{Sec}$, wherein the non-naturally occurring tRNA$^{Sec}$ is recognized by SerRS and by EF-Tu, or variants thereof, and when aminoacylated with serine the Ser-tRNA (1) is a substrate for SelA or a variant thereof; or (2) is a substrate for PSTK and when aminoacylated with phosphorylated serine the Sep-tRNA serves as a substrate for SepSecS or a variant thereof,
wherein the non-naturally occurring tRNA comprises a nucleic acid sequence according to SEQ ID NO: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, or 58.

3. The isolated nucleic acid of claim 2 further comprising a heterologous expression control sequence.

4. An expression vector comprising the isolated nucleic acid of claim 3.

5. A host cell comprising the isolated nucleic acid of claim 2.

6. The host cell of claim 5 wherein the host cell is a prokaryote, archaeon, or eukaryote.

7. The host cell of claim 6 wherein the prokaryotic cell is *E. coli*.

8. The host cell of claim 7 wherein the endogenous *E. coli* genes encoding selA, selB, and selC, or combinations thereof have been deleted or mutated to reduce or prevent expression of SelA, SelB, or SelC protein.

9. The host cell of claim 5 wherein the host cell expresses one or more of the proteins selected from the group consisting of SerRS, EF-Tu, SelA, or PSTK and SepSecS.

10. The host cell of claim 5 wherein the host cell expresses SerRS, EF-Tu, and SelA.

11. The host cell of claim 5 wherein the host cell expresses SerRS, EF-Tu, PSTK and SepSecS.

12. The host cell of claim 11 wherein the PSTK is a *M. maripaludis* PSTK or a variant thereof.

13. The host cell of claim 11 wherein the SepSecS is a *M. jannaschii* SepSecS or a variant thereof.

14. The non-naturally occurring tRNASec of claim 1, wherein when aminoacylated with selenocysteine the non-naturally occurring tRNASec inserts a selenocysteine into a nascent peptide chain during translation without the requirement of a SECIS in the mRNA encoding the peptide, in the absence of SelB, or a combination thereof.

15. The isolated nucleic acid of claim 2, wherein when aminoacylated with selenocysteine the non-naturally occurring tRNA$^{Sec}$ inserts, a selenocysteine into a nascent peptide chain during translation without the requirement of a SECIS in the mRNA encoding the peptide, in the absence of SelB, or a combination thereof.

16. The non-naturally occurring tRNA$^{Sec}$ of claim 1, wherein the tRNA$^{Sec}$ comprises a nucleic acid sequence according to SEQ ID NO:6, 7, or 8.

17. The isolated nucleic acid of claim 2 wherein the non-naturally occurring tRNA$^{Sec}$ comprises a nucleic acid sequence according to SEQ ID NO:6, 7, or 8.

18. The host cell of claim 5 wherein the non-naturally occurring tRNA$^{Sec}$ comprises a nucleic acid sequence according to SEQ ID NO:6, 7, or 8.

19. The host cell of claim 5 wherein the nucleic acid is integrated into the host cell's genome.

* * * * *